(12) United States Patent
Kutyavin

(10) Patent No.: US 9,121,056 B2
(45) Date of Patent: Sep. 1, 2015

(54) USE OF PRODUCTS OF PCR AMPLIFICATION CARRYING ELEMENTS OF SECONDARY STRUCTURE TO IMPROVE PCR-BASED NUCLEIC ACID DETECTION

(76) Inventor: Igor Kutyavin, Woodinville, WA (US)

( * ) Notice: Subject to any disclaimer, the term of this patent is extended or adjusted under 35 U.S.C. 154(b) by 1054 days.

(21) Appl. No.: 12/298,900

(22) PCT Filed: Apr. 30, 2007

(86) PCT No.: PCT/US2007/067836
§ 371 (c)(1),
(2), (4) Date: Mar. 31, 2009

(87) PCT Pub. No.: WO2007/127999
PCT Pub. Date: Nov. 8, 2007

(65) Prior Publication Data
US 2010/0143898 A1 Jun. 10, 2010

Related U.S. Application Data

(60) Provisional application No. 60/795,705, filed on Apr. 28, 2006.

(51) Int. Cl.
*C12Q 1/68* (2006.01)
(52) U.S. Cl.
CPC .............. *C12Q 1/6853* (2013.01); *C12Q 1/686* (2013.01)
(58) Field of Classification Search
None
See application file for complete search history.

(56) References Cited

U.S. PATENT DOCUMENTS

| | | | |
|---|---|---|---|
| 4,458,066 A | 7/1984 | Caruthers et al. | |
| 4,683,195 A | 7/1987 | Mullis et al. | |
| 4,683,202 A | 7/1987 | Mullis | |
| 5,168,038 A | 12/1992 | Tecott et al. | |
| 5,210,015 A | 5/1993 | Gelfand et al. | |
| 5,234,809 A | 8/1993 | Boom et al. | |
| 5,270,184 A | 12/1993 | Walker et al. | |
| 5,418,149 A | 5/1995 | Gelfand et al. | |
| 5,422,253 A | 6/1995 | Dahlberg et al. | |
| 5,691,142 A | 11/1997 | Dahlberg et al. | |
| 5,719,028 A | 2/1998 | Dahlberg et al. | |
| 5,723,591 A | 3/1998 | Livak et al. | |
| 5,824,517 A | 10/1998 | Cleuziat et al. | |
| 5,837,450 A | 11/1998 | Dahlberg et al. | |
| 5,843,669 A | 12/1998 | Kaiser et al. | |
| 5,846,717 A | 12/1998 | Brow et al. | |
| 5,854,033 A | 12/1998 | Lizardi | |
| 5,888,780 A | 3/1999 | Dahlberg et al. | |
| 5,925,517 A | 7/1999 | Tyagi et al. | |
| 5,985,557 A | 11/1999 | Prudent et al. | |
| 5,994,069 A | 11/1999 | Hall et al. | |
| 6,001,567 A | 12/1999 | Brow et al. | |
| 6,063,603 A | 5/2000 | Davey et al. | |
| 6,090,543 A | 7/2000 | Prudent et al. | |
| 6,214,587 B1 | 4/2001 | Dattagupta et al. | |
| 6,251,639 B1 | 6/2001 | Kurn | |
| 6,348,314 B1 | 2/2002 | Prudent et al. | |
| 6,350,580 B1 | 2/2002 | Sorge | |
| 6,410,278 B1 | 6/2002 | Notomi et al. | |
| 6,448,010 B1 | 9/2002 | Zhao | |
| 6,528,254 B1 | 3/2003 | Sorge | |
| 6,548,250 B1 | 4/2003 | Sorge | |
| 6,589,743 B2 | 7/2003 | Sorge | |
| 6,875,572 B2 | 4/2005 | Prudent et al. | |
| 6,893,819 B1 | 5/2005 | Sorge | |
| 6,913,881 B1 | 7/2005 | Aizenstein et al. | |
| 7,118,860 B2 | 10/2006 | Sorge et al. | |
| 7,183,052 B2 | 2/2007 | Sorge | |
| 7,252,940 B2 | 8/2007 | Kutyavin et al. | |
| 2003/0044796 A1* | 3/2003 | Neri et al. | 435/6 |
| 2005/0026166 A1* | 2/2005 | Bi | 435/6 |

FOREIGN PATENT DOCUMENTS

WO    WO 2007/127999    11/2007

OTHER PUBLICATIONS

Sharma et al. Molecular and Cellular Probes (1999) 13: 291-302.*
Ailenberg et al. BioTechniques (2000) 29: 1018, 1020, 1022-1024.*
Kao et al., "Cleavage Specificity of *Saccharomyces cerevisiae* Flap Enconuclease 1 Suggests a Double-Flap Structure as the Cellular Substrate," The Journal of Biological Chemistry, 2002, pp. 14379-14389, vol. 277.
Liu et al., "*Saccharomyces cerevisiae* Flap Endonuclease 1 Use Flap Equilibration to Maintain Triplet Repeat Stability," Molecular and Cellular Biology, 2004, pp. 4049-4064, vol. 24.
Myers et al., "Reverse Transcription and DNA Amplification by a *Therms thermophilus* DNA Polymerase," Biochemistry, 1991, pp. 7661-7666, vol. 30.
Solinas et al., "Intramolecular TaqMan probes for genetic analysis," Chemical Communications, 2002, pp. 2272-2273, vol. 19.

(Continued)

*Primary Examiner* — Angela M Bertagna
(74) *Attorney, Agent, or Firm* — Barry L. Davison; Davis Wright Tremaine LLP

(57) ABSTRACT

Particular aspects comprise amplifying target nucleic acid using PCR and an oligonucleotide primer pair wherein at least one of the primers is designed to incorporate a 5'-specialty sequence to provide for an amplification product that intramolecularly folds into a secondary structure; and detecting the amplification product by a method comprising: providing an oligonucleotide cleavage component, hybridizing the oligonucleotide cleavage component with the amplification product to form a three-strand cleavage structure wherein two strands of the three-strand cleavage structure are provided by the secondary structure of the amplification product, cleaving 3'- or 5'-strands of the three-strand cleavage structure using a duplex-specific nuclease activity resulting in a cleavage product, and detecting the cleavage product indicative of the presence of the target nucleic acid. In certain aspects both primers incorporate a 5'-specialty sequence and detecting comprises cleaving 3'- or 5'-strands of a three-strand cleavage structure using duplex-specific nuclease to provide a cleavage product.

37 Claims, 19 Drawing Sheets

(56) References Cited

OTHER PUBLICATIONS

Wang et al., "Human Bloom Protein Stimulates Flap Endonuclease 1 Activity by Resolving DNA Secondary Structure," The Journal of Biological Chemistry, 2005, pp. 5391-5399, vol. 280.

U.S. Appl. No. 60/795,705, filed Apr. 28, 2006, Kutyavin.

Afonina et al., "Efficient priming of PCR with short oligonucleotides conjugated to a minor groove binder," Nucleic Acids Research, 1997, pp. 2657-2660, vol. 25.

Afonina et al., "Minor Groove Binder-Conjugated DNA Probes for Quantitative DNA Detection by Hybridization-Triggered Fluorescence," BioTechniques, 2002, pp. 940-949, vol. 32.

Afonina et al., "Single Nucleotide Polymorphism Detection with MGB Eclipse™ Assays," Journal of Clinical Ligand Assays, 2002, pp. 268-275, vol. 25.

An et al., "Characterization of a Thermostable UvrD Helicase and Its Participation in Helicase-dependant Amplification," The Journal of Biological Chemistry, 2005, pp. 28952-28958, vol. 280.

Beaucage et al., "Deoxynucleoside Phosphoramidites—A New Class of Key Intermediates for Deoxypolynucleotide Synthesis," Tetrahedron Letters, 1981, pp. 1859-1862, vol. 22.

Becker-Andre, "Absolute mRNA quantification using the polymerase chain reaction (PCR). A novel approach by a PCR aided transcript titration assay (PATTY)," Nucleic Acids Research, 1989, pp. 9437-9446, vol. 17.

Bedinger et al., "Sequence-specific Pausing during in Vitro DNA Replication on Double-stranded DNA Templates," The Journal of Biological Chemistry, 1989, pp. 16880-16886, vol. 264.

Belyavsky et al., "PCR-based cDNA library construction: general cDNA libraries at the level of a few cells," Nucleic Acids Research, 1989, pp. 2919-2932, vol. 17.

Bierne et al., "When replication forks stop," Molecular Microbiology, 1994, pp. 17-23, vol. 13.

Bonnet et al., "Thermodynamic basis of the enhanced specificity of structured DNA probes," The Proceedings of the National Academy of Sciences, 1999, pp. 6171-6176, vol. 96.

Breslauer et al., "Predicting DNA duplex stability from the base sequence," The Proceedings of the National Academy of Sciences, 1986, pp. 3746-3750, vol. 83.

Brown et al., "Chemical Synthesis and Cloning of a Tyrosine tRNA Gene," Methods in Enzymology, 1979, pp. 109-151, vol. 68.

Brownie et al., "The elimination of primer-dimer accumulation in PCR," Nucleic Acids Research, 1997, pp. 3235-3241, vol. 25.

Burgner et al., "Improved Allelic Differentiation Using Sequence-Specific Oligonucleotide Hybridization Incorporating an Additional Base-Analogue Mismatch," Nucleosides, Nucleotides & Nucleic Acids, 2004, pp. 755-765, vol. 23.

Cardullo et al., "Detection of nucleic acid hybridization by nonradiative fluorescence resonance energy transfer," The Proceedings of the National Academy of Sciences, 1988, pp. 8790-8794, vol. 85.

Clegg et al., "Fluorescence resonance energy transfer," Current Opinion in Biotechnology, 1995, pp. 103-110, vol. 6.

Clegg et al., "Fluorescence Resonance Energy Transfer and Nucleic Acids," Methods in Enzymology, 1992, pp. 353-388, vol. 211.

Clementi et al., "Quantitative PCR and RT-PCR in Virology," PCR Methods and Applications, 1993, pp. 191-196, vol. 2.

Didenko et al., "DNA Probes Using Fluorescence Resonance Energy Transfer (FRET): Designs and Applications," Biotechniques, 2001, pp. 1106-1121, vol. 31.

Di Giusto et al., "Strong positional preference in the interaction of LNA oligonucleotides with DNA polymerase and proofreading exonuclease activities: implications for genotyping assays," Nucleic Acids Research, 2004, p. e32, vol. 32 (8 pages).

Diviacco et al., "A novel procedure for quantitative polymerase chain reaction by coamplification of competitive templates," Gene, 1992, pp. 313-320, vol. 122.

Doty et al., Strand Separation and Specific Recombination in Deoxyribonucleic Acids: Physical Chemical Studies, The Proceedings of the National Academy of Science, 1960, pp. 461-476, vol. 46.

Fedurco et al., "BTA, a novel reagent for DNA attachment on glass and efficient generation of solid-phase amplified DNA colonies," Nucleic Acids Research, 2006, p. e22, vol. 34 (13 pages).

Fong et al., "Rapid Solid-Phase Immunoassay for Detection of Methicillin-Resistant *Staphylococcus aureus* Using Cycling Probe Technology," Journal of Clinical Microbiology, 2000, pp. 2525-2529, vol. 38.

Freeman et al., "Quantitative RT-PCR: Pitfalls and Potential," BioTechniques, 1999, pp. 112-125, vol. 26.

Gu et al., "Multiplexed, Real-Time PCR for Quantitative Detection of Human Adenovirus," Journal of Clinical Microbiology, 2003, pp. 4636-4641, vol. 41.

Gundry et al., "Rapid F508del and F508C Assay Using Fluorescent Hybridization Probes," Genetic Testing, 1999, pp. 365-370, vol. 3.

Haas et al., "Purification and Characterization of *Thermotoga maritima* Endonuclease IV, a Thermostable Apurinic/Apyrimidinic Endonuclease and 3'-Repair Diesterase," Journal of Bacteriology, 1999, pp. 2834-2839, vol. 181.

Hacia et al., "Enhanced high density oligonucleotide array-based sequence analysis using modified nucleoside triphosphates," Nucleic Acids Research, 1998, pp. 4975-4982, vol. 26.

Hafner et al., "Isothermal Amplification and Multimerization of DNA by Bst DNA Polymerase," BioTechniques, 2001, pp. 852-867, vol. 30.

Harvey et al., "Characterization and applications of CataCleave probe in real-time detection assays," Analytical Biochemistry, 2004, pp. 246-255, vol. 333.

Higuchi et al., "Kinetic PCR Analysis: Real-time Monitoring of DNA Amplification Reactions," Bio/Technology, 1993, pp. 1026-1030, vol. 11.

Higuchi et al., "Simultaneous Amplification and Detection of Specific DNA Sequences," Bio/Technology, 1992, pp. 413-417, vol. 10.

Ichihara et al., "Construction of new T vectors for direct cloning of PCR products," Gene, 1993, pp. 153-154, vol. 130.

Ishiguro et al., "Homogenous Quantitative Assay of Hepatitis C Virus RNA by Polymerase Chain Reaction in the Presence of a Fluorescent Intercalater," Analytical Biochemistry, 1995, pp. 207-213, vol. 229.

Johnson et al., "Locked nucleic acid (LNA) single nucleotide polymorphism (SNP) genotype analysis and validation using real-time PCR," Nucleic Acids Research, 2004, p. e55, vol. 32 (9 pages).

Kojima et al., "PCR amplification from single DNA molecules on magnetic beads in emulsion: application for high-throughput screening of transcription factor targets," Nucleic Acids Research, 2005, p. e150, vol. 33 (9 pages).

Kutyavin et al., "3'-Minor groove binder-DNA probes increase sequence specificity at PCT extension temperatures," Nucleic Acids Research, 2000, pp. 655-661, vol. 28.

Kutyavin et al., "Oligonucleotides with conjugated dihydropyrroloindole tripeptides: base composition and backbone effects on hybridization," Nucleic Acids Research, 1997, pp. 3718-3723, vol. 25.

Kutyavin et al., "A novel endonuclease IV post-PCR genotyping system," Nucleic Acids Research, 2006, p. e128, vol. 34 (9 pages).

Laduca et al., "Site-Specific Pausing of Deoxyribonucleic Acid Synthesis Catalyzed by Four Forms of *Escherichia coli* DNA Polymerase III," Biochemistry, 1983, pp. 5177-5188, vol. 22.

Latorra et al., "Design considerations and effects of LNA in PCR primers," Molecular and Cellular Probes, 2003, pp. 253-259, vol. 17.

Latorra et al., "Enhanced Allele-Specific PCR Discrimination in SNP Genotyping Using 3' Locked Nucleic Acid (LNA) Primers," Human Mutation, 2003, pp. 79-85, vol. 22.

Lebedev et al., "Oligonucleotides containing 2-aminoadenine and 5-methylcytosine are more effective as primers for PCR amplification than their nonmodified counterparts," Genetic Analysis: Biomolecular Engineering, 1996, pp. 15-21, vol. 13.

Levin et al., "Homogenous *Escherichia coli* Endonuclease IV," The Journal of Biological Chemistry, 1988, pp. 8066-8071, vol. 263.

Lewin et al., "Use of Real-Time PCR and Molecular Beacons to Detect Virus Replication in Human Immunodeficiency Virus Type 1-Infected Individuals on Prolonged Effective Antiretroviral Therapy," Journal of Virology, 1999, pp. 6099-6103, vol. 73.

Lie et al., "Advances in quantitative PCR technology: 5' nuclease assays," Current Opinion in Biotechnology, 1998, pp. 43-48, vol. 9.

(56) References Cited

OTHER PUBLICATIONS

Livak et al., "Oligonucleotides with Fluorescent Dyes at Opposite Ends Provide a Quenched Probe System Useful for Detecting PCR Product and Nucleic Acid Hybridization," PCR Methods and Applications, 1995, pp. 357-362, vol. 4.
Ljungquist et al., "A New Endonuclease from *Escherichia coli* Acting at Apurinic Sites in DNA," The Journal of Biological Chemistry, 1977, pp. 2808-2814, vol. 252.
Lutfalla et al., "Performing Quantitative Reverse-Transcribed Polymerase Chain Reaction Experiments," Methods in Enzymology, 2006, pp. 388-400, vol. 410.
Lyamichev et al., "Structure-Specific Endonucleolytic Cleavage of Nucleic Acids by Eubacterial DNA Polymerases," Science, 1993, pp. 778-783, vol. 260.
MacKay et al., "Real-Time PCR Fluorescent Chemistries," Methods in Molecular Biology, 2007, pp. 237-262, vol. 353.
MacKay et al., "Real-Time PCR in virology," Nucleic Acids Research, 2002, pp. 1292-1305, vol. 30.
Marmur et al., "Strand Separation and Specific Recombination in Dyoxyribonucleic Acids: Biological Studies," The Proceedings of the National Academy of Sciences, 1960, pp. 453-461, vol. 46.
Marras et al., "Efficiencies of fluorescence resonance energy transfer and contact-mediated quenching in oligonucleotide probes," Nucleic Acids Research, 2002, p. e122, vol. 30 (8 pages).
Mercier et al., Solid Phase DNA Amplification: A Browian Dynamics Study of Crowding Effects, Biophysical Journal, 2005, pp. 32-42, vol. 89.
Mercier et al., "Solid Phase DNA Amplification: A Simple Monte Carlo Lattice Model," Biophysical Journal, 2003, pp. 2075-2086, vol. 85.
Miller et al., "A simple salting out procedure for extracting DNA from human nucleated cells," Nucleic Acids Research, 1988, p. 1215, vol. 16.
Mitterer et al., "Microarray-Based Detection of Bacteria by On-Chip PCR," Methods in Molecular Biology, pp. 37-51, vol. 345, published 2006.
Modrusan et al., "CPT-EIA assays for the detection of vancomycin resistant vanA and vanB genes in enterococci," Diagnostic Microbiology and Infectious Disease, 2000, pp. 45-50, vol. 37.
Morrison et al., "Quantification of Low-Copy Transcripts by Continuous SYBR® Green I Monitoring during Amplification," BioTechniques, 1998, pp. 954-962, vol. 24.
Myers et al., "Reverse Transcription and DNA Amplification by a *Thermus thermophilus* DNA Polymerase," Biochemistry, 1991, pp. 7661-7666, vol. 30.
Narang et al, "Improved Phosphotriester Method for the Synthesis of Gene Fragments," Methods in Enzymology, 1979, pp. 90-98, vol. 68.
Nazarenko et al., "Effect of primary and secondary structure of oligodeoxyribonucleotides on the fluorescent properties of conjugated dyes," Nucleic Acids Research, 2002, pp. 2089-2095, vol. 30.
Nazarenko et al., "Multiplex quantitative PCR using self-quenched primers labeled with a single fluorophore," Nucleic Acids Research, 2002, p. e37, vol. 30 (7 pages).
Nguyen et al., "Quantitative assessment of the use of modified nucleoside triphosphates in expression profiling: differential effects on signal intensities and impacts on expression ratios," BMC Biotechnology, 2002, p. 14, vol. 2 (15 pages).
Niesters, "Quantitation of Viral Load Using Real-Time Amplification Techniques," Methods, 2001, pp. 419-429, vol. 25.
Notomi et al., "Loop-mediated isothermal amplification of DNA," Nucleic Acids Research, 2000, p. e63, vol. 28 (7 pages).
Oehlenschläger et al., "Detection of HIV-1 RNA by nucleic acid sequence-based amplification combined with fluorescence correlation spectroscopy," The Proceedings of the National Academy of Sciences, 1996, pp. 12811-12816, vol. 93.
Ortiz et al., "PNA molecular beacons for rapid detection of PCR amplicons," Molecular and Cellular Probes, 1998, pp. 219-226, vol. 12.
Piatek et al., "Molecular beacon sequence analysis for detecting drug resistance in *Mycobacterium tuberculosis*," Nature Biotechnology, 1998, pp. 359-363, vol. 16.

Puglisi et al., "Absorbance Melting Curves of RNA," Methods in Enzymology, 1989, pp. 304-325, vol. 180.
Robelek et al., "Multiplexed Hybridization Detection of Quantum Dot-Conjugated DNA Sequences Using Surface Plasmon Enhanced Fluorescence Microscopy and Spectrometry," Analytical Chemistry, 2004, pp. 6160-6165, vol. 76.
Santalucia, "A unified view of polymer, dumbbell, and oligonucleotide DNA nearest-neighbor thermodynamics," The Proceedings of the National Academy of Sciences, 1998, pp. 1460-1465, vol. 95.
Schneeberger et al., "Quantitative Detection of Reverse Transcriptase-PCR Products by Means of a Novel and Sensitive DNA Stain," PCR Methods and Applications, 1995, pp. 234-238, vol. 4.
Schweitzer et al., "Combining nucleic acid amplification and detection," Current Opinion in Biotechnology, 2001, pp. 21-27, vol. 12.
Selvin, "Fluorescence Resonance Energy Transfer," Methods in Enzymology, 1995, pp. 300-334, vol. 246.
Simeonov et al., "Single nucleotide polymorphism genotyping using short, fluorescently labeled locked nucleic acid (LNA) probes and fluorescence polarization detection," Nucleic Acids Research, 2002, p. e91, vol. 30 (5 pages).
Simpson et al., "A Method for Specific Cloning and Sequencing of Human HPRT cDNA for Mutation Analysis," Biochemical and Biophysical Research Communications, 1988, pp. 487-492, vol. 151.
Solinas et al., "Duplex Scorpion primers in SNP analysis and FRET applications," Nucleic Acids Research, 2001, p. e96, vol. 29 (9 pages).
Strauss et al., "Substrate Binding by Human Apurinic/Apyrimidinic Endonuclease Indicates a Briggs-Haldane Mechanism," The Journal of Biological Chemistry, 1997, pp. 1302-1307, vol. 272.
Stryer et al., "Energy Transfer: A Spectroscopic Ruler," The Proceedings of the National Academy of Sciences, 1967, pp. 719-726, vol. 58.
Sugimoto et al., "Improved thermodynamic parameters and helix initiation factor to predict stability of DNA duplexes," Nucleic Acids Research, 1996, pp. 4501-4505, vol. 24.
Thelwell et al., "Mode of action and application of Scorpion primers to mutation detection," Nucleic Acids Research, 2000, pp. 3752-3761, vol. 28.
Tseng et al., "An Homogenous Fluorescence Polymerase Chain Reaction Assay to Identify Salmonella," Analytical Biochemistry, 1997, pp. 207-212, vol. 245.
Tyagi et al., "Molecular Beacons: Probes that Fluoresce upon Hybridization," Nature Biotechnology, 1996, pp. 303-308, vol. 14.
Tyagi et al, "Wavelength-shifting molecular beacons," Nature Biotechnology, 2000, pp. 1191-1196, vol. 18.
Van Ness et al., "A versatile solid support system for oligodeoxynucleotide probe-based hybridization assays," Nucleic Acids Research, 1991, pp. 3345-3350, vol. 19.
Vincent et al., "Helicase-dependant isothermal DNA amplification," EMBO Reports, 2004, pp. 795-800, vol. 5.
Walker et al., "DNA detection by strand displacement amplification and fluorescence polarization with signal enhancement using DNA binding protein," Nucleic Acids Research, 1996, pp. 348-353, vol. 24.
Walsh et al., "Chelex® 100 as a Medium for Simple Extraction of DNA for PCR-Based Typing from Forensic Material," 1991, BioTechniques, pp. 506-513, vol. 10.
Walter et al., "Coaxial stacking of helixes enhances binding of oligoribonucleotides and improves predictions of DNA folding," The Proceedings of the National Academy of Sciences, 1994, pp. 9218-9222, vol. 91.
Whitcombe et al., "Detection of PCR products using self-probing amplicons and fluorescence," Nature Biotechnology, 1999, pp. 804-807, vol. 17.
Vi et al., "Molecular Zipper: a fluorescent probe for real-time isothermal DNA amplification," Nucleic Acids Research, 2006, p. e81, vol. 34 (5 pages).
Zuker et al., "'Well-determined' regions in RNA secondary structure prediction: analysis of small subunit ribosomal RNA," Nucleic Acids Research, 1995, pp. 2791-2798, vol. 23.

* cited by examiner

USE OF PRODUCTS OF PCR AMPLIFICATION CARRYING ELEMENTS OF SECONDARY STRUCTURE TO IMPROVE PCR-BASED NUCLEIC ACID DETECTION

CROSS-REFERENCE TO RELATED APPLICATIONS

This application claims the benefit of priority to U.S. Provisional Patent Application Ser. Nos. 60/795,705, filed 28 Apr. 2006, which is incorporated herein by reference in its entirety.

FIELD OF THE INVENTION

Aspects of the invention relate generally to improved nucleic acid detection methods, and particularly to improved amplification-based nucleic acid detection methods comprising the novel use of nucleic acid secondary structure.

SEQUENCE LISTING

A Sequence Listing comprising SEQ ID NOS:1-22 incorporated by reference herein in its entirety as part of this application.

BACKGROUND

I. PCR-Based DNA Detection Technologies

Nucleic acid detection assays and sensitivity. Known DNA and/or RNA detection techniques are based on the principle of complementarity. For example, an oligonucleotide sequence is selected based on its ability to form a complementary duplex with a desired or predetermined nucleic acid target sequence, and the complementary duplex is detected, indicating the presence of the targeted nucleic acid in the reaction mixture. Such hybridization based detection assays should, at least in principal, detect the nucleic acid of interest regardless of its concentration in the test sample. However, the sensitivity of such direct detection hybridization assays is limited, and although some highly sensitive technologies for direct nucleic acid detection are currently under development, amplification of targeted nucleic acids is an important component of typical DNA detection systems. Numerous amplification technologies are known in the art, the most notorious examples including: *Strand Displacement Amplification* (SDA) (Walker G. T. et al, U.S. Pat. No. 5,270,184; Dattagupta N. et al, U.S. Pat. No. 6,214,587; Walker G. T. et al (1996) *Nucleic Acids Res.*, 24, 384-353); *Rolling Circle Amplification* (RCA) (Lizardi P., U.S. Pat. No. 5,854,033); *Linear target Isothermal Multimerization and Amplification* (LIMA) (Hafner G. J. et al (2001) *BioTechniques*, 30, 852-867); *Loop-Mediated Amplification* (LMA) (Notomi T. and Hase T., U.S. Pat. No. 6,410,278; Notomi T. et al (2000) *Nucleic Acids Res.*, 28, e63); *Isothermal Amplification using chimeric or composite RNA/DNA primers* (Cleuziat P. and Mandrand B., U.S. Pat. No. 5,824,517; Kurn N. (2001) U.S. Pat. No. 6,251,639); *Nucleic Acid Sequence-Based Amplification* (NASBA) (Oehlenschlager F. et al (1996) *Proc. Natl. Acad. Sci. USA*, 93, 12811-12816; Davey C. and Malek L. T., U.S. Pat. No. 6,063,603); and other methods. By far, the most common element among these technologies is the use of oligonucleotide primers that form complementary hybridization complexes with desired/predetermined target sequences of the test nucleic acids, initiating synthesis of DNA copies and providing for target nucleic acid amplification.

Demands for quantitative measurements of nucleic acids of interest, for example, of limiting viral or bacterial loads in test samples, prompted development of real time assays in which the amplification products are detected as the amplification reaction progresses. This significantly decreases the number of subsequent handling steps required for the detection of amplified material and also helps to resolve amplification cross-contamination issue. Fluorescence can be detected at a nanomolar level well within the sensitivity and productivity of many known nucleic acid amplification technologies. Development of real time fluorescence-based detection assays has been reported for many nucleic acid amplification schemes, for example, a fluorescent probe called a Molecular Zipper was effectively combined with Rolling Circle amplification (Yi J. et al (2006) Nucleic Acids Res., 34: e81) and several fluorescence-based detection approaches were combined with NASBA amplification (Niesters H. G. (2001) Methods, 25: 419-429).

Polymerase chain reaction (PCR) methodology has revolutionized the detection of nucleic acids, where at least in theory, as little as a single copy of DNA or RNA can be amplified and detected. A typical PCR-based detection assay consists of at least two primers and a fluorescent probe. Fluorescence can be detected at the nanomolar level, which is well within the range of PCR sensitivity and productivity. PCR primers are typically designed to bind to opposite DNA strands; that is, the primers bind in an orientation such that extension of one creates a template for the other primer. The PCR reaction runs in cycles in which DNA fragments synthesized in the previous cycle are 'strand-separated' in a denaturation step (typically at 95° C.), followed by rapid cooling to start an 'annealing-extension' stage (typically carried out at 55-65° C.). In annealing stage, the primers bind again to the amplified strands and get extended by a thermophilic DNA polymerase. Under optimal PCR conditions, the concentration of the amplified DNA fragment doubles at each PCR cycle reaching a detectable level after ~20-40 cycles depending on the initial target amount/load.

Application of fluorescence based methods led to development of many real time detection techniques (Clementi M. et al (1993) PCR Methods Appl. 2:191-196; Clegg R. M. (1992) Methods Enzymol., 211: 353-388; Freeman W. M. et al (1999) Biotechniques, 26: 112-122, 124-125; Didenko V. V. (2001) BioTechniques, 31: 1106-1121; Mackay I. M. et al (2002) Nucleic Acids Res., 30: 1292-1305; Mackay J., Landt O. (2007) Methods Mol. Biol., 353: 237-262; Higuchi R. et al (1992) Biotechnology, 10: 413-417; Higuchi R. et al (1993) Biotechnology, 11: 1026-1030; Lewin S. R. et al (1999) J. Virol., 73: 6099-6103; etc.). This significantly simplified nucleic acid detection eliminating the variability traditionally associated with quantitative PCR. A simple approach to detect DNA in PCR is based on use of fluorescent agents like ethidium bromide, YO-PRO-1, SYBR Green and other dyes which change their fluorescence properties upon the interaction with double stranded nucleic acids providing detectable signal (Ishiguro T. et al (1995) Anal. Biochem., 229: 207-213; Tseng S. Y. et al (1997) Anal. Biochem., 245: 207-212; Morrison T. B. et al (1998) Biotechniques, 24: 954-958; Schneeberger C. et al (1995) PCR Methods Appl., 4: 234-238; and Mackay J., Landt O. (2007) Methods Mol. Biol., 353: 237-262). The principal drawback to this method of DNA detection is that both specific and nonspecific products generate signal and this may lead to false positive results limiting applicability of the approach, in particular, in clinical diagnostics. Real-time systems were improved by probe-based PCR product detection. Fluorescent probes are oligonucleotides which typically labeled with two fluorescent dyes. The probes are designed to bind exclusively to a target amplicon usually between the primer binding sites providing the desired assay specificity. This also enables multiplex PCR wherein multiple target nucleic acids are simultaneously amplified and detected. The probe-based detection of PCR amplicon commonly employs Förster Resonance Energy Transfer (FRET) effects.

FRET-based detection. FRET is a distance-dependent interaction occurring between two dye molecules in which excitation is transferred from a donor to an acceptor fluorophore through dipole-dipole interactions without the emission of a photon. As a result, the donor molecule fluorescence is quenched, and the acceptor molecule becomes excited. The efficiency of FRET depends on spectral properties, relative orientation and distance between the donor and acceptor chromophores (Förster T. (1965) Delocalized excitation and excitation transfer. In Sinanoglu, O. (ed.), Modern Quantum Chemistry, Istanbul Lectures, part III. Academic Press, New York: 93-137). In the case of random dipole orientation and with a good overlap between the emission spectrum of the donor and the absorption spectrum of the acceptor, the efficiency of FRET is dependent on the inverse sixth power of the intermolecular separation (Clegg R. M. (1992) Methods Enzymol., 211: 353-388; Clegg R. M. (1995) Curr. Opin. Biotech., 6: 103-110; Selvin P. R. (1995) Methods Enzymol., 246: 300-334), making FRET useful over distances comparable to the dimensions of biological macromolecules (Stryer L. and Haugland R. P. (1967) Proc. Natl. Acad. Sci. USA, 58:719-726). FRET is widely used in biomedical research and particularly in probe designs for nucleic acid detection (Didenko V. V. (2001) BioTechniques, 31, 1106-1121).

The acceptor chromophore may be a non-fluorescent dye chosen to quench fluorescence of the reporting fluorophore (Eftink M. R. (1991) In Lakowicz J. R. (ed.), Topics in Fluorescence Spectroscopy. Plenum Press, New York, V.2: 53-126). Formation of sequence-specific hybrids between the target nucleic acid and the probes leads to a changes in fluorescent properties of the probe providing for detection of the nucleic acid target. The real-time FRET based assays are particularly well suited for clinical diagnostics, because unlike the case of intercalating dyes and fluorescent agents (e.g. ethidium bromide, SYBR Green) discussed above, the detection is sequence-specific, virtually eliminating false positive results.

'Hybridization-triggered' FRET probes. Many detection strategies and designs exploiting the FRET effect are known in the art. One strategy is a hybridization-triggered FRET probe approach, based on distance change between the donor and acceptor dyes as result of a sequence specific complex formation between a target nucleic acid and a fluorescent oligonucleotide probe. For example, the 'Adjacent Hybridization Probe' method utilizes two oligonucleotide probes hybridizing to adjacent target DNA sequences as described in e.g. Eftink M. R. (1991) In Lakowicz J. R. (ed.), Topics in Fluorescence Spectroscopy. Plenum Press, New York, V.2 53-126; Heller M. J. and Morrison L. E. (1985) In Kingsbury, D. T. and Falkow, S. (eds.), Rapid Detection and Identification of Infectious Agents. Academic Press, New York, 245-256; Cardullo R. A. et al (1988) Proc. Natl. Acad. Sci. USA, 85:8790-8794. Each of the probes is labeled by one of FRET-pair dyes at an appropriate probe end such that when both probes are hybridized to a target DNA, the donor and acceptor fluorophores are brought in spatial proximity of each other providing for a detectable FRET interaction.

'Self-Quenching Fluorescence' probes. An alternative approach is the use of 'Self-Quenching Fluorescence' probes described in Livak K. J. et al, U.S. Pat. No. 5,723,591. These probes include fluorescent reporter and quencher moieties conjugated to opposite ends of the same probe. Due to random oligonucleotide coiling, the quencher moiety is sufficiently close to the reporter dye to quench its fluorescence. However, once the probe is hybridized to a complementary polynucleotide target, the quencher and reporter moieties are separated, thus enabling the reporter dye to fluoresce. The Self-Quenching Fluorescence probes approach has been limited because of an inefficient FRET effect in the unhybridized probe that leads to an elevated fluorescence background. The background problem can be resolved by synthesizing the oligonucleotide with a flexible PNA backbone (e.g. Ortiz E. et al (1998) Mol. Cell. Probes, 12, 219-226).

'Molecular beacon' probes. Efficient FRET is achieved in 'Molecular Beacons', which are hairpin-shaped oligonucleotide probes in which the FRET dyes are brought in close proximity by intramolecular stem formation (e.g. Tyagi S, and Kramer F. R. (1996) Nat. Biotechnol., 14: 303-308; Bonnet G. et al (1999) Proc. Natl. Acad. Sci. USA, 96:6171-6176; Tyagi S. et al (2000) Nat. Biotechnol., 18:1191-1196; Marras S. A. E. et al (2002) Nucleic Acids Res., 30 e122). Hybridization of a Molecular Beacon probe to a complementary polynucleotide target opens the hairpin probe structure and separates the quencher and reporter moieties enabling the reporter dye to fluoresce. Molecular Beacons are known for their remarkably low fluorescence background, and these probes are well adapted for use in real-time PCR as described in, e.g. Piatek A. S. et al (1998) Nat. Biotechnol., 16:359-363; Lewin S. R. et al (1999) J. Virol., 73 6099-6103. Molecular Beacons have also improved polymorphism discriminating capabilities.

'Scorpion' primers. Covalent linking of a 'molecular beacon' probe to one of the PCR primers is a unique property of 'Scorpion' primers, e.g. Whitcombe D. et al (1999) Nature Biotech., 17:804-807; Thelwell N. et al (2000) Nucleic Acids Res., 28:3752-3761. In Scorpions the 5'-end of a PCR primer is conjugated to the 3'-end of a molecular beacon through a long, flexible linker. The linker is not a template for DNA polymerase, thus precluding extension over the beacon sequence. The genomic part of the molecular beacon is designed to bind to a targeted extension product of the primer to which the probe is covalently linked. Unlike Molecular Beacons, the DNA detection stage in Scorpions comprises an intra-molecular reaction. This property helps to overcome a known problem of the Beacon technology associated with slow kinetics of hybridization.

Eclipse probes. Eclipse probes are yet another example of hybridization-based FRET probes that have low fluorescence background (Afonina I. A. et al (2002) BioTechniques, 32 940-949). The Eclipse probe design includes a minor groove binding (MGB) moiety at the 5'-end in addition to two FRET dyes one of which is a non-fluorescent or dark quencher. Due to the strong, DNA-duplex stabilizing effect of the MGB-moiety (Kutyavin I. V. et al (1997) Nucleic Acids Res., 25:3718-3723), the probes can be designed to be as short as 12-20-mers and yet maintain the hybridization properties required for real-time PCR detection. Placing the MGB-tail at 5'-end of the probes completely blocks 5'-nuclease cleavage and the fluorescent signal is generated solely due to the hybridization-triggered dye separation. Fluorescence background is low and Eclipse probes readily discriminate SNPs.

'Self-Quenched Fluorogenic primers' or 'LUX' primers. The mechanism of FRET disruption by the distancing of FRET dyes poses certain limits. For example, it is difficult to completely abolish the FRET effect, and probes have to be at least 20-24-mers. In short 8-12 by probe-target duplexes, "residual" quenching can reach as high as 20-50% (Cardullo R. A. et al (1988) Proc. Natl. Acad. Sci. USA, 85:8790-8794). Furthermore, the reporter dye can be partially quenched by neighboring bases, in particular, by guanines regardless of the limited spectral overlap. This effect is well known and has been used in a DNA detection technology known by the name of 'Self-Quenched Fluorogenic primers' or 'Light Upon eXtension' (LUX primers), e.g. Nazarenko I. et al (2002) Nucleic Acids Res., 30: e37; Nazarenko I. et al (2002) Nucleic Acids Res., 30: 2089-2195. The technology performs best with "green" dyes like fluorescein (FAM). However, LUX primers are not sequence-specific. Any product of a LUX primer extension, including primer-dimers, will generate a fluorescent signal.

Cleavable dual labeled FRET probes; TaqMan™. The best strategy to abolish FRET is based on cleavage of the oligonucleotide probes upon their binding to target nucleic acids. TaqMan™ technology was developed as a real-time nucleic acid detection method and utilizes the 5'-3' exonuclease activity of *Thermus aquaticus* (Taq) polymerase, e.g. Lie Y. S. and Petropoulos C. J. (1998) Curr. Opin. Biotech., 9:43-48. A dual labeled FRET probe is designed to anneal to a target sequence located between two PCR primer binding sites. During strand elongation, Taq polymerase cleaves the probe that is hybridized down stream from a primer site releasing the reporter dye from the quencher and thus permanently and irreversibly disrupting FRET, e.g. Livak K. J. et al (1995) PCR Methods and Applications, 4:357-362. Since the probe cleavage is irreversible, the signal generated at a given PCR cycle is a sum of signals generated at that particular cycle plus all previous ones. However, elevated fluorescence background of the "classical" TaqMan™ probes tends to overshadow this advantage. Conjugation with an MGB-moiety at the 3'-end leads to significant improvement of this parameter (Kutyavin I. V. et al (2000) Nucleic Acids Res., 28:655-661). Relatively short 12-18-mer MGB-TaqMan™ probes have improved SNP discriminating properties. However, TaqMan™ technology is still tightly bound to PCR performance whereas Cycling Probe Technologies (CPT) are relatively independent.

Cycling Probe Technologies (CPT). Cycling Probe Technologies (CPT) are also preferred detection systems for practicing methods of the invention. These reactions are based on continuous cleavage of oligonucleotide probes which bind to a target nucleic acid in a sequence-specific fashion. An appropriate endonuclease recognizes the complex and cleaves the probe while leaving the target strand intact recycling it for the next round of cleavage. If the hybridized probe is cleaved internally, the cleavage products form weaker hybrids than the original probe and these probe fragments dissociate from the target strand leaving it available for additional rounds of the cleavage reaction. Target recycling means that more than one probe can be cleaved per target molecule. Unlike all other technologies referred above, including TaqMan™, in CPT reactions the signal is a function of two main variables, target concentration and time. When the target concentration is fixed, the signal grows linearly in time. Reflecting the reaction progress, cleavage slows down and eventually stops when essentially all CPT probes get cleaved. Several system designs have been reported. The first approach is based on use of chimeric DNA-RNA probes that are cleaved by RNAse H upon the binding to target DNA, as described in Fong W. et al (2000) *J. Clin. Microbiol.*, 38: 2525-2529; Modruzan Z. et al (2000) *Diagn. Microbiol. Infect. Dis.*, 37:45-50. These DNA probes are designed to have at least 4-5 ribonucleotides in the middle of the oligonucleotide chain. RNAse H cleaves only the RNA portion of the hybridized probe and the target polynucleotide is recycled to hybridize to another uncleaved probe molecule. Under appropriate conditions, this leads to a cycling of the probe cleavage reaction. Recent discovery and isolation of thermo-stable analogs of RNAse H have allowed combining this DNA detection technology with PCR as demonstrated in e.g. Harvey J. J. et al (2004) *Anal. Biochem.*, 333: 246-255. The respective FRET probes may be obtained from Takara Bio.

The second CPT approach is based on the substrate specificity of Endonuclease IV from *E. coli*, an AP endonuclease that initiates repair of abasic sites and other related lesions in DNA. A FRET probe and enhancer can collectively form a substrate for the AP endonuclease that simulates a partially degraded abasic site. The enzyme recognizes this artificial substrate and "clips" the 3'-tail of the probe thereby releasing the reporter dye and disrupting FRET. This reaction can be performed in a cycling mode where a high yield of cleaved probe is achieved at nanomolar or even sub-nanomolar target DNA concentrations as described in Kutyavin I. V. et al (2004) US Patent Application #20040101893.

Third, and perhaps, the most advanced cycling probe technology on the market is the INVADER™ detection assay. It utilizes the flap or 5'-endonuclease activity of certain polymerases to cleave two partially overlapping oligonucleotides upon their binding to target DNA. The INVADER™ assay typically consists of two consecutive cycling cleavage reactions. The enzyme used to provide the cleavage reaction is CLEAVASE, a DNA polymerase with substantially reduced or completely eliminated synthetic capabilities, e.g. Dahlberg J. E. et al (1997) U.S. Pat. No. 5,691,142; Dahlberg J. E. et al (1998) U.S. Pat. No. 5,837,450; Brow M. A. D. et al (1998) U.S. Pat. No. 5,846,717; Prudent J. R. et al (1999) U.S. Pat. No. 5,985,557; Hall J. G. et al (1999) U.S. Pat. No. 5,994,069; Brow M. A. D. et al (1999) U.S. Pat. No. 6,001,567; Prudent J. R. et al (2000) U.S. Pat. No. 6,090,543; Prudent J. R. et al (2002) U.S. Pat. No. 6,348,314; Prudent J. R. et al (2005) U.S. Pat. No. 6,875,572; Aizenstein B. D. et al (2005) U.S. Pat. No. 6,913,881; Schweitzer B. and Kingsmore S. (2001) *Curr. Opin. Biotech.*, 12: 21-27. The detection system is a very efficient signal amplification assay which may not require any prior target DNA amplification. However, prior amplification of nucleic acids is a preferred approach in applying the INVADER assay. The primary concern is background fluorescence that increases linearly with time. It is generated by non-specific cleavage of the cassette probe. Furthermore the assay requires substantial target DNA load, e.g. Schweitzer B. and Kingsmore S. (2001) *Curr. Opin. Biotech.*, 12:21-27, when the amplification is not applied. Combinations of CPT with nucleic acid amplification techniques provide critical advantages as described for the oligonucleotide probes with secondary structures in Sorge J. A. (2001) U.S. Pat. No. 6,589,743.

Sorge J. A. also reported methods of nucleic acid detection wherein a cleavage structure comprising duplex and single-stranded nucleic acid is formed by incubating a sample comprising a target nucleic acid sequence with a probe having a secondary structure that changes upon binding to the target nucleic acid sequence, and cleaving said cleavage structure with a nuclease to release a nucleic acid fragment to generate a signal. In certain embodiments, the hybridized probes are cleaved during PCR. Unlike the TaqMan™ assays, it has also been proposed to provide DNA polymerase and 5'-nuclease (FEN) activities which are necessary to perform the methods using different enzymes. Sorge J. A. also describes an approach of sequential cleavage reaction, similar to the 'Invader' assay, to enhance the signal detection reaction. The technology is collectively disclosed in many published patents, e.g. Sorge J. A. U.S. Pat. No. 6,350,580, U.S. Pat. No.

6,528,254, U.S. Pat. No. 6,548,250, U.S. Pat. No. 6,893,819, U.S. Pat. No. 7,118,860 and U.S. Pat. No. 7,183,052.

The cited and above-described nucleic acid detection technologies represent an exemplary fraction of innovations and methods in this field of art. There are many other techniques that are based on use of oligonucleotide probes and, in particular, FRET probes. All of the technologies that are based on hybridization of an oligonucleotide probe with a target nucleic acid would benefit from use the present invention. Detailed guidance in performing a particular detection reaction including the rules for oligonucleotide primer and probe designs, preferred composition of the reaction mixtures, reaction conditions, characteristics of the assays and its applicability and limitations, and other important information to carry out the detection reactions can be found in cited above manuscripts and patents which are incorporated herein by reference.

Regardless of the significant progress made to date, methods of nucleic acids detection are still not optimal. Therefore, there is a pronounced need in the art for versatile, effective but simple and inexpensive approaches providing fast and robust amplification and detection of target nucleic acids.

BRIEF DESCRIPTION OF DRAWINGS

FIG. 14A shows the design of oligonucleotide components used in the assays. Reverse primers #2-6 (SEQ ID NOS:3-7, respectively) contained FRET-labeled specialty sequences of variable length but the same primer template sequence as shown for the reverse primer (SEQ ID NO:3). "FAM" is a 6-carboxy fluorescein whereas "Q" is BHQ1 quencher (Glen Research). The specialty sequences were coupled to the 5'-end of the common primer template sequence through a long and flexible polyethylene glycol C18 linker (Glen Research). A synthetic 96-mer oligonucleotide (SEQ ID NO:1), shown in part at the top of FIG. 14A, was used as a target nucleic acid. The sequence of the primers or their binding sites is underlined within the target sequence.

FIG. 14B shows curves of fluorescence monitoring during the PCR cycles. The curves of every specialty primer tested in PCR are identified by a length of the specialty sequence.

FIG. 14C is a logarithmic representation of the same data shown in FIG. 14B. This is particularly useful in determining of the threshold values (Ct) for real time curves which are identified herein as interception points between the curves and axis X (PCR cycles). Appropriate stock solutions of the reaction components were mixed to provide the following concentrations in PCR (25 µl): forward (Primer #1) (SEQ ID NO:2) and one of the reverse specialty Primers #2-6 (SEQ ID NOS: 3-7, respectively)—200 nM each; target oligonucleotide—10,000 copies per reaction; dNTPs—200 µM each; JumpStart DNA polymerase (Sigma)—0.04 U/µl in 50 mM KC1, 2 mM MgC12, 20 mM Tris-HC1 (pH 8.0). PCR was performed on SmartCycler (Cepheid Corporation) using a time/temperature profile (95° 2') →(95° 10"→60° 45")$_{55}$. The reaction fluorescence was measured at the annealing/extension cycle stage (60° 45") and plotted versus PCR cycles providing real time curves shown in FIG. 14B. Background fluorescence was subtracted using the instrument software.

FIG. 15A shows the design of oligonucleotide components used in the assays. Forward primers #9-13 (SEQ) ID NOS:8-12)incorporated 5'-specialty sequences of a variable length. The oligonucleotide primer #1 (SEQ ID NO:2) is a conventional PCR primer (no 5'-specialty tail). Use of the forward primers #9-13 in combination with the reverse primer #7 (SEQ ID NO:3) in PCR leads to formation of amplicons which fold into secondary structures as shown in FIG. 7. The 5'-specialty tail sequences of the primers #9-13 (SEQ ID NOS:8-12) were designed to provide respectively 6, 7, 8, 10 and 14-mer secondary structure duplexes, which collectively with a FRET-probe #8 (SEQ ID NO:13) form optimal cleavage structures for 5'-nuclease. The specialty sequences which participate in these duplex formations are underlined in the primers #9-13 (SEQ ID NOS:8-12). The 5'-terminal adenosine is not complementary to the target DNA providing a single nucleotide flap as shown in FIG. 7. "FAM" is a 6-carboxy fluorescein whereas "Q" is BHQ1 quencher (Glen Research). A synthetic 96-mer oligonucleotide (SEQ ID NO:1) was used as a target nucleic acid. The sequences of the primers or their binding sites as well as a binding site of the specialty sequences are underlined within the target sequence. The FRET-probe sequence is shown in bold font. Every forward primer shown in this Figure was individually tested in a real time PCR assay in a reaction mixture with the FRET-probe #8 (SEQ ID NO:13) and the reverse primer #7 (SEQ ID NO:3).

FIG. 15B shows the results of the fluorescence monitoring in the reactions of FIG. 15A. The curves are identified by a length of the specialty sequence fragment (underlined in primers #9-13) (SEQ ID NOS:8-12) which participates in the duplex formation (folded amplicons). Combination of the primers #1 (SEQ ID NO:2) and 7 (SEQ ID NO:3) with the FRET-probe #8 (SEQ ID NO:13) (No 5'-tail) represents a conventional (TaqMan) assay design.

FIG. 15C is a logarithmic representation of the same data shown in FIG. 15B provided here to determine the threshold values (Ct) as described in the context of FIG. 14. Appropriate stock solutions of the reaction components were mixed to provide the following concentrations in PCR (25 µl): one of the forward (primers #1 (SEQ ID NO:2) or 9-13 (SEQ ID NOS:8-12) and the reverse primer #7 (SEQ ID NO:3)—100 nM each; FRET-probe #8 (SEQ ID NO:13)—400 nM; target oligonucleotide—10,000 copies per reaction; dNTPs—200 µM each; JumpStart DNA polymerase (Sigma)—0.04 U/µl in 50 mM KCl, 2 mM MgC12, 20 mM Tris-HCl (pH8.0). PCR was performed on SmartCycler (Cepheid Corporation) using a time/temperature profile (95° 2') →(95° 10"→64° 45") $_{55}$. The reaction fluorescence was measured at the annealing/extension cycle stage (64° 45''') and plotted versus PCR cycles providing real time curves shown in FIG. 15B. Background fluorescence was subtracted using the instrument software.

FIG. 16A shows the design of oligonucleotide components used in these experiments. A synthetic 96-mer oligonucleotide (SEQ ID NO:1), shown in part at the top of FIG. 16A, was used as a target nucleic acid The specialty sequences which participate in the amplicon secondary structure formation are underlined in primers #11, 12, 14 and 15 (SEQ ID NOS:10, 11, 16, 17). The forward primers #14 and 15 (SEQ ID NOS:16, 17) are different from the primers #11 and 12 (SEQ ID NOS:10, 11), respectively by absence of a 5'-terminal adenosine. Primers #11 and 12 were designed to provide amplicons folding into secondary structures with a 3'-single nucleotide flap as shown in FIG. 7. These amplicons hybridized to a FRET-probe #8 (SEQ ID NO:13) to form optimal three-strand structures for cleavage by 5'-nuclease. Use of the oligonucleotide primers #14 and 15 provides the amplicon secondary structures with no flaps as shown in FIG. 12. Formation of suboptimal structures, e.g. structure B in FIG. 1, was anticipated for these 5'-specialty primers #14, 15. The forward primers were individually studied in PCR in a reaction mixture with the FRET-probe #8 (SEQ ID NO:13) and the reverse primer #7 (SEQ ID NO:3).

FIG. 16B shows the results of the fluorescence monitoring in the reactions of 16A. The curves are identified by a length of the specialty sequence fragment (8-mer or 10-mer) which participates in the duplex formation of the folded amplicons (underlined) and presence (+flap) or absence (−flap) of a single base flap.

FIG. 16C is a logarithmic representation of the same data shown in FIG. 16B provided here to determine the threshold values (Ct) as described in the FIG. 14 legend. Appropriate stock solutions of the reaction components were mixed to provide the following concentrations in PCR (25 μl): a forward primer (#11, 12, 14 or 15) and the reverse primer #7—100 nM each; FRET-probe #8—200 nM; target oligonucleotide—10,000 copies per reaction; dNTPs—200 μM each; JumpStart DNA polymerase (Sigma)—0.04 U/μl in 50 mM KCl, 2 mM MgCl2, 20 mM Tris-HCl (pH 8.0). PCR was performed on SmartCycler (Cepheid Corporation) using a time/temperature profile (95°2')→(95°10"→60°45")$_{55}$. The reaction fluorescence was measured at the annealing/extension cycle stage (60°45") and plotted versus PCR cycles providing real time curves shown in FIG. 16B. Background fluorescence was subtracted using the instrument software.

```
                                        (SEQ ID NO: 18)
5'-CTCTCGGCCCGCATTCCTGAAGCTGACAGCA-3'   Primer #16

(SEQ ID NO: 19)
5'-CCATCTCGGCGCATTCCTGAAGCTGACAGCA-3'   Primer #17

(SEQ ID NO: 20)
5'-CACATCTCGGCGCATTCCTGAAGCTGACAGCA-3'  Primer #18

(SEQ ID NO: 21)
5'-CGACATCTCGGGCATTCCTGAAGCTGACAGCA-3'  Primer #19

(SEQ ID NO: 22)
5'-CAGACATCTCGGGCATTCCTGAAGCTGACAGCA-3' Primer #20
```

The underlined sequences in primers #16-20 are specialty sequences that participate in amplicon secondary structure formation. 5'-Terminal cytosine is not complementary to the target DNA. The fluorescent curves shown in FIG. 17A correspond to the following combinations of primers:

| | |
|---|---|
| 19-mer: | Primers #2 + 16 |
| 15-mer: | Primers #3 + 17 |
| 13-mer: | Primers #4 + 18 |
| 11-mer: | Primers #5 + 19 |
| 9-mer: | Primers #6 + 20 |

Appropriate stock solutions of the reaction components were mixed to provide the following concentrations in PCR (25 μl): a forward primer (primers #16-20) and a reverse primer (primers #2-6)—200 nM each; target oligonucleotide—10,000 copies per reaction; dNTPs—200 μM each; JumpStart DNA polymerase (Sigma)—0.04 U/μl in 50 mM KCl, 2 mM MgCl2, 20 mM Tris-HCl (pH 8.0). PCR was performed on SmartCycler (Cepheid Corporation) using a time/temperature profile (95°2')→(95°10"→60°45")$_{55}$. The reaction fluorescence was measured at the annealing/extension cycle stage (60°45") and plotted versus PCR cycles providing real time curves shown in FIG. 17A. Background fluorescence was subtracted using the instrument software.

Figure 14:
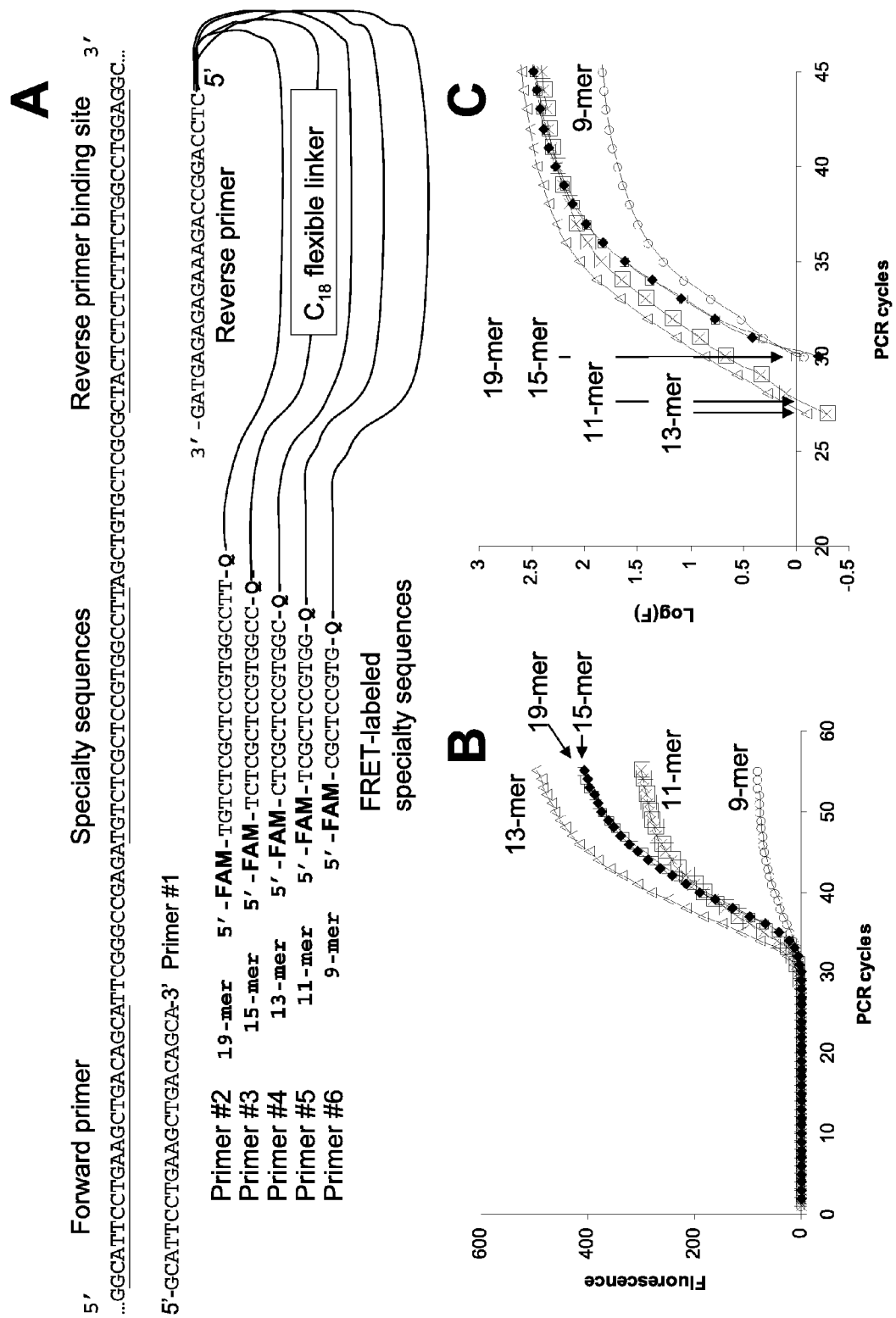
FIG. 14 shows experimental data from performing real time FRET assays according to a method of the invention as described in the context of FIG. 5.

FIG. 17B is a logarithmic representation of the same data shown in FIG. 17A provided here to determine the threshold values (Ct) as described in the FIG. 14 legend.

Figure 8:
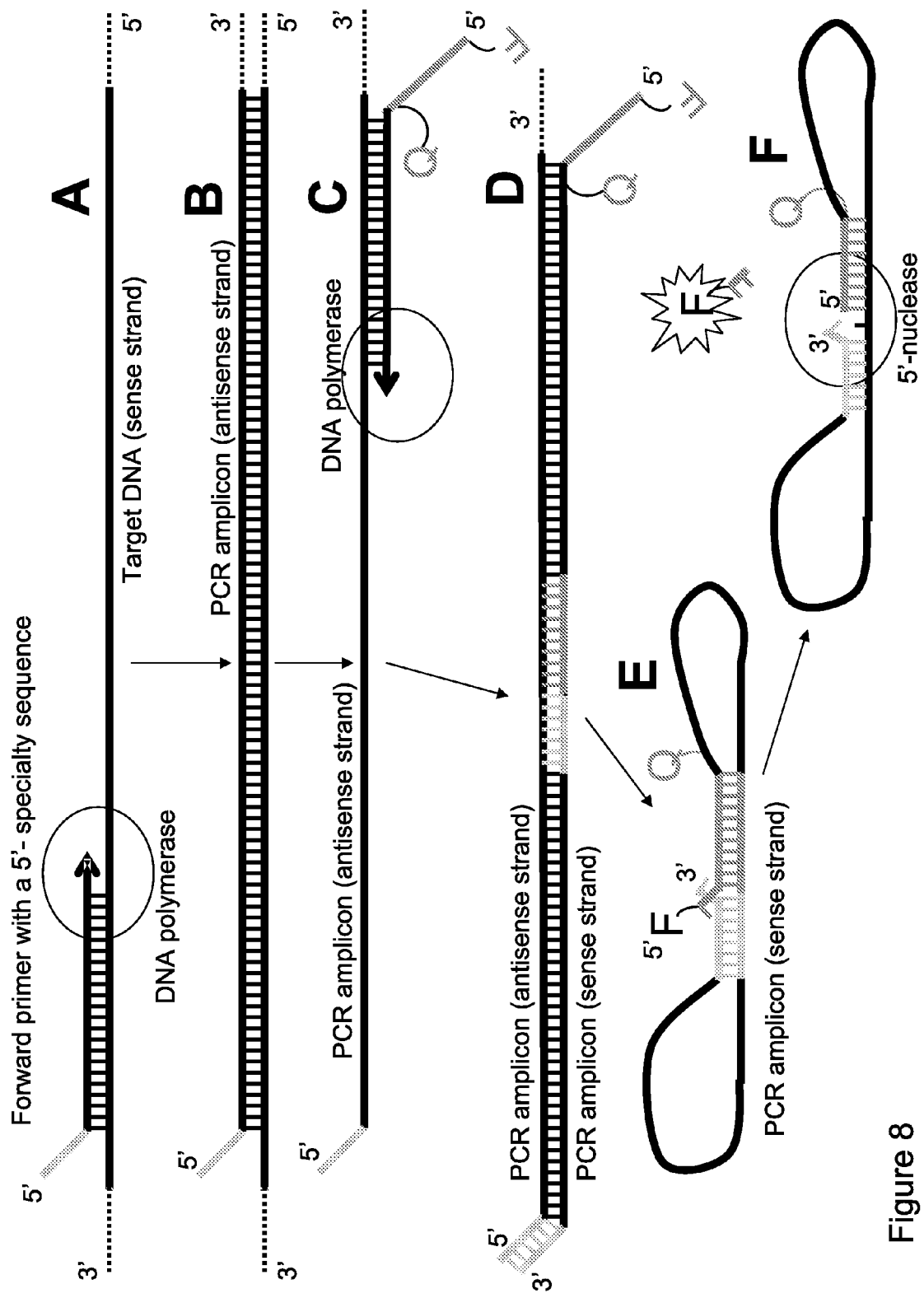
FIGS. 8A-8F shows yet another method embodiment, wherein formation of a three-strand cleavage structure does not require use of an oligonucleotide cleavage component (e.g., cleavage enhancer) and wherein all three strands of the cleavage structure are provided by a PCR amplicon. The method is based on use of two oligonucleotide primers, both of which incorporate 5'-specialty sequences. Hybridization of these primers with the respective strands of target nucleic acids and their extension by DNA polymerase in consequent stages A-D leads to an amplicon (sense strand) which folds into a secondary structure shown in stage E. This secondary structure represents an optimal cleavage structure for a 5'-nuclease which provides the cleavage of the 5'-strand disrupting the FRET. This method is a combination of the approaches shown in FIGS. 6 and 7. In this particular case, the FRET primer does not incorporate a non-extendable linker and its 5'-specialty sequence is designed to provide a single nucleotide 5'-flap (stage E). Such a design is preferred because of the potential problem described in the context of FIG. 12.
Figure 17:
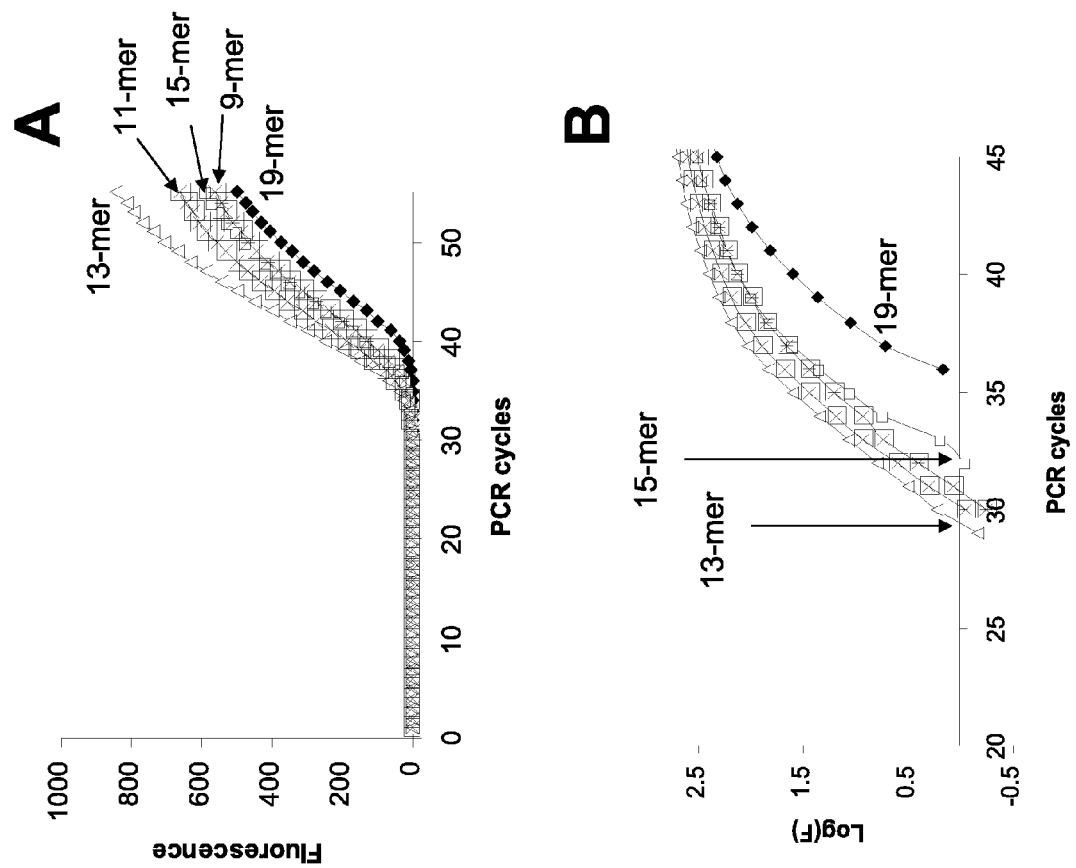
FIG. 17 shown results of real time fluorescence assays that were performed according to a method of the invention described in the context of FIG. 8. In these assays, forward and reverse oligonucleotide primers incorporated 5'-specialty sequences to provide PCR amplicons which fold into three-strand cleavage structures. Structures of the reverse FRET-labeled primers #2-6 used in these experiments are shown in FIG. 14. Sequences of the forward oligonucleotide primers are shown below.
Figure 18:
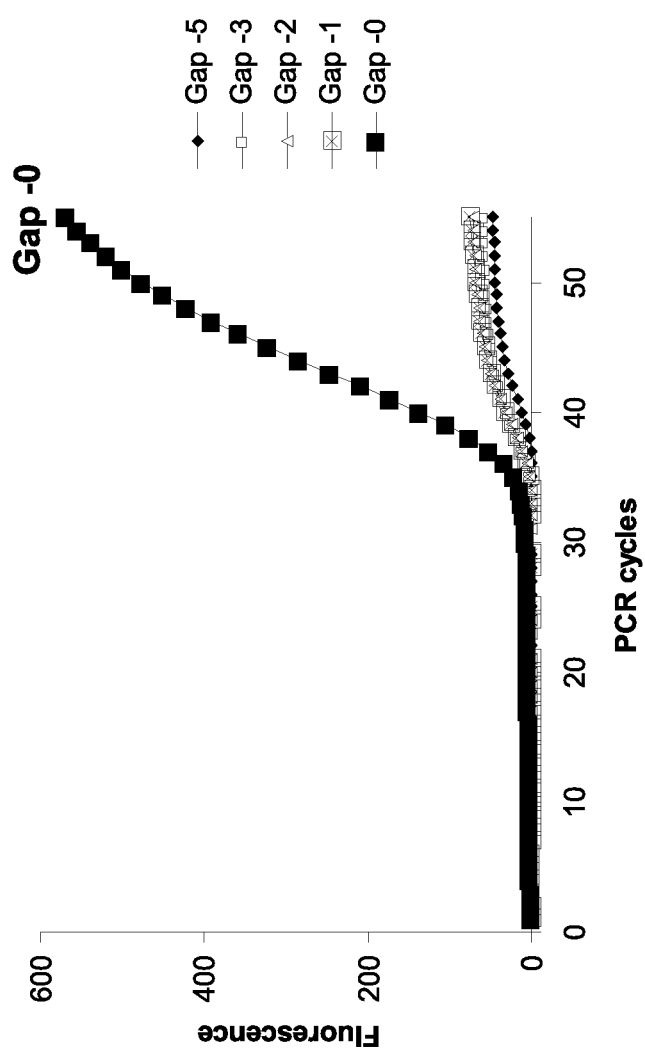

FIG. 18 shows experimental results demonstrating a preference in oligonucleotide primer design according to the method of the invention described in the context of FIG. 8. A FRET-labeled reverse primer #6 (9-mer, structure is shown in FIG. 14) was tested in real time assays individually with forward primers #16-20 (sequences given in the context of FIG. 17). Combining the primers #6 and #20 in PCR leads to an amplicon which folds into a three-strand structure (curve "Gap −0" in this FIG. 18) that is an optimal cleavage structure for 5'-nuclease (structure D, FIG. 1) whereas the combinations with other primers #16, 17, 18 and 19 provide amplicons with suboptimal cleavage structures having respectively 5, 3, 2 and 1 nucleotide gap in the target strand between the secondary structure duplexes. The fluorescence curves for these combinations are identified accordingly in the figure as "Gap −5," "Gap −3," "Gap −2" and "Gap −1". The PCR conditions, oligonucleotide component and reagent concentrations and time/temperature profile used were the same as described in Example 4 and in the context of FIG. 17.

Figure 19:
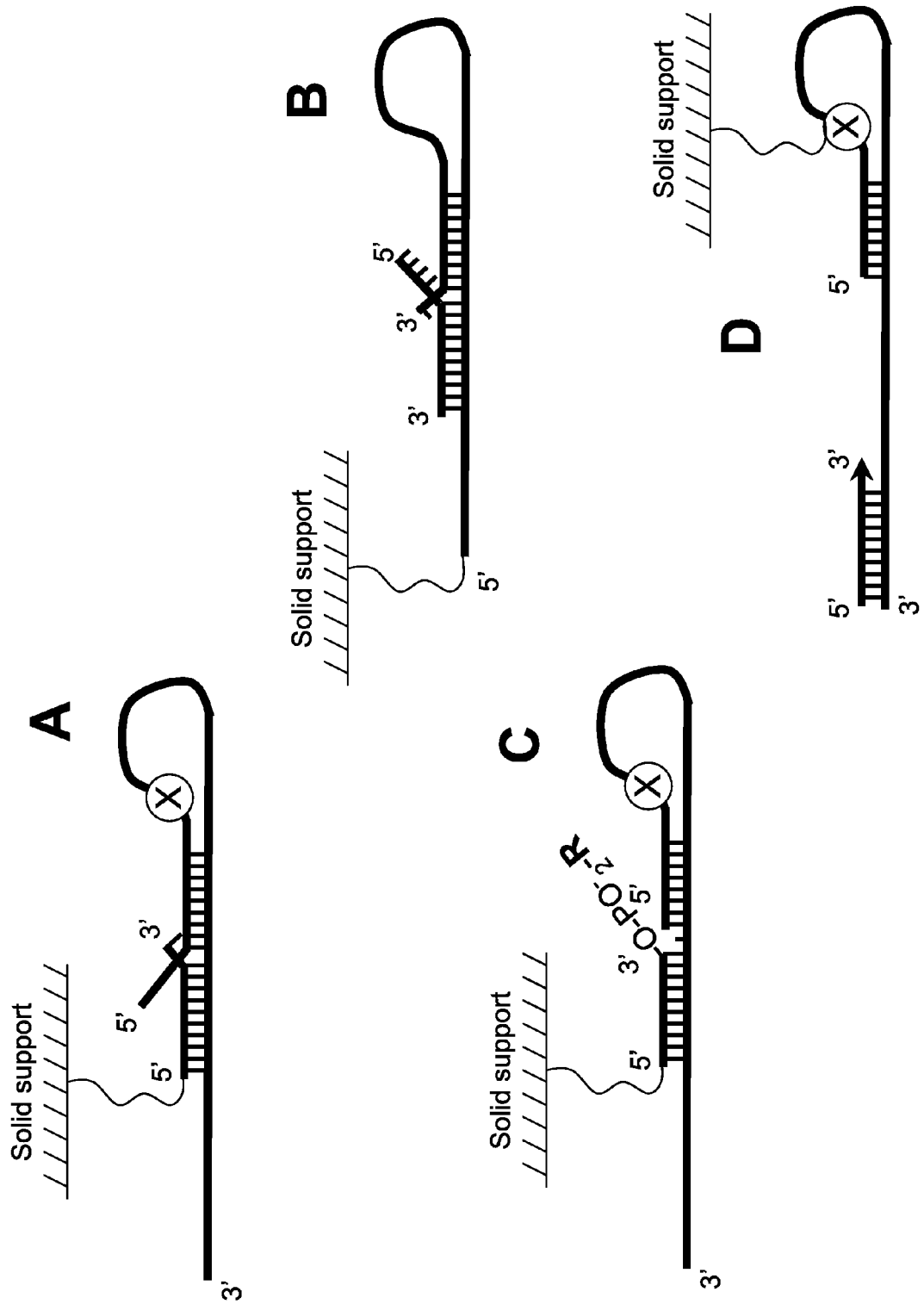

FIG. 19 diagrammatically shows certain examples of immobilization of oligonucleotide components or amplicons of the invention during PCR or detection reactions. Panel A is wherein a cleavage enhancer in 5'-nuclease assay is coupled to a solid support. Panel B illustrates the method shown in FIG. 7 wherein a reverse (conventional) oligonucleotide primer is coupled by its 5'-end to a solid support. Panel C shows an immobilized probe in a 3'-nuclease method of the invention which is discussed in FIG. 11. Panel D demonstrates immobilization of a specialty oligonucleotide primer in the method of FIG. 5.

SUMMARY OF ASPECTS OF THE INVENTION

Aspects of the present invention provide novel methods for the detection of nucleic acids, comprising nucleic acid amplification using nucleic acid secondary structure.

Particular aspects provide a method for the detection of a target nucleic acid in a sample, comprising: amplifying, in a reaction mixture, a target nucleic acid using PCR in the presence of a pair of oligonucleotide primers wherein at least one of the oligonucleotide primers is designed to incorporate a 5'-specialty sequence to provide an amplification product that intramolecularly folds into a secondary structure; and detecting the amplification product that folds into a secondary structure by a method comprising: providing an oligonucleotide cleavage component, hybridizing said oligonucleotide cleavage component with the amplification product to form a three-strand cleavage structure wherein two strands of the three-strand cleavage structure are provided by the secondary structure of the amplification product, cleaving 3'- or 5'-strands of the three-strand cleavage structure using a duplex-specific nuclease activity resulting in a cleavage product, and detecting the cleavage product, wherein the presence of the cleavage product is indicative of the presence of the target nucleic acid in said sample.

Additional aspects provide a method for the detection of a target nucleic acid in a sample, comprising: amplifying, in a reaction mixture, a target nucleic acid using PCR in presence of a pair of oligonucleotide primers wherein both oligonucleotide primers are designed to incorporate a 5'-specialty sequence to provide amplification products that intramolecular fold into three-strand cleavage structures; and detecting at least one of the amplification products by a method comprising: cleaving 3'- or 5'-strands of the three-strand cleavage structure using a duplex-specific nuclease activity resulting in a cleavage product, and detecting the cleavage product, wherein the presence of the cleavage product is indicative of the presence of the target nucleic acid in the sample.

In particular embodiments of the above described methods, the target nucleic acid is or comprises DNA. In additional aspects, the target nucleic acid is or comprises RNA, and amplifying of the target nucleic acid includes a stage wherein at least one DNA copy of the RNA is synthesized using a reverse transcriptase activity. In certain embodiments, the reverse transcriptase activity is provided by DNA polymerase used in PCR.

In certain aspects, amplifying the target nucleic acid is performed first followed by the step of detecting the amplification product. In other aspects, amplifying the target nucleic acid and detecting the amplification product are performed in real time.

In certain embodiments, the oligonucleotide cleavage component provides the 3'-strand and the amplification product which folds into a secondary structure provides the 5'-strand of the three-strand cleavage structure. In particular embodiment, the oligonucleotide cleavage component provides the 5'-strand and the amplification product which folds into a secondary structure provides the 3'-strand of the three-strand cleavage structure.

In particular embodiments, the oligonucleotide cleavage component is cleaved. In additional embodiments, the amplification product is cleaved. In certain embodiments, the three-strand cleavage structure is cleaved.

Particular embodiments of the invention comprise amplification of more than one target nucleic acid in the same reaction mixture using, for each target sequence, a pair of oligonucleotide primers wherein at least one, or both of the oligonucleotide primers is designed to incorporate a 5'-specialty sequence to provide an amplification product that intramolecularly folds into a secondary structure, wherein one or more of said target nucleic acids are amplified and detected.

In certain aspects, amplifying and detecting of the target nucleic acids are performed to measure the amount of the target nucleic acids in the sample. In other aspects, amplifying and detecting of the target nucleic acids are performed to determine polymorphic variations of the target nucleic acids in the sample.

In particular embodiments, the duplex-specific cleavage is provided by 5'-nuclease activity. In certain embodiment, the three-strand cleavage structure is an optimal cleavage structure for 5'-nuclease activity. In particular aspects, the 5'-nuclease activity is provided by a DNA polymerase used in amplifying said target nucleic acid. In certain embodiments, the DNA polymerase comprises Taq polymerase.

In some aspects, the 5'-nuclease activity is provided by an enzyme that does not express a DNA polymerase activity. In certain embodiments, the enzyme that does not express a DNA polymerase activity is FEN. In certain embodiments, the enzyme that does not express a DNA polymerase activity is or comprises cleavase.

In some aspects, the duplex-specific cleavage is provided by a 3'-nuclease activity. In certain embodiments, the 3'-nuclease activity is provided by an Endonuclease IV or equivalent activity. In particular embodiments, the three-strand cleavage structure is an optimal cleavage structure for Endonuclease IV.

In particular aspects, the oligonucleotide cleavage component and the oligonucleotide primer which that does not incorporate the 5'-specialty sequence are the same molecule.

In particular embodiments, the oligonucleotide cleavage component is created during extension of an oligonucleotide primer hybridized to said amplification product that intramolecularly folds into a secondary structure, and wherein cleavage of the three-strand cleavage structure in provided by a 5'-nuclease activity. In certain aspects, the cleavage is performed in a cycling mode.

In certain embodiments, the oligonucleotide primers that are designed to incorporate a 5'-specialty sequence are fully extendable in PCR. In particular aspects, one of the oligonucleotide primers that are designed to incorporate a 5'-specialty sequence is partially extendable in PCR provided that said 5'-specialty sequence is coupled to the 5'-end of the primer through a none-extendable linker.

In certain aspects, at least one of the oligonucleotide components is immobilized on a solid support during amplification and/or detection stages.

In certain embodiments, the cleavage product comprises or is a flap oligonucleotide. In particular aspects, the flap oligonucleotide serves as an oligonucleotide cleavage component in a different cleavage reaction in the reaction mixture providing a 3'-strand to a different three-strand cleavage structure that is cleaved by a 5'-nuclease resulting in a different cleavage product, and detecting the different cleavage product, wherein the presence of the different cleavage product is indicative of the presence of the flap oligonucleotide and the target nucleic acid in the sample. In certain aspects, the different cleavage product contains a label and the label is used in detecting of the different cleavage products. In certain aspects, the label comprises a fluorescent label.

DETAILED DESCRIPTION OF THE INVENTION

Aspects of the present invention provide novel methods for the detection of nucleic acids, comprising nucleic acid amplification using nucleic acid secondary structure as disclosed herein (e.g., including those of exemplary FIGS. 1-18).

Definitions

As used herein, terms and symbols of biochemistry, nucleic acid chemistry, molecular biology and molecular genetics follow those of standard treaties and texts in the field, for example, Sambrook et al, Molecular Cloning: A Laboratory Manual, $2^{nd}$ Edition (Cold Spring Harbor Laboratory, 1989); Kornberg and Baker, DNA Replication, Second Edition (W.H. Freeman, New York, 1992); Gaits, ed., Oligonucleotide Synthesis: A Practical Approach (IRL Press, Oxford, 1984); Lehninger, Biochemistry, Second Edition (Worth Publishers, New York, 1975); Eckstein, ed., Oligonucleotides and Analogs: A Practical Approach (Oxford University Press, New York, 1991); and the like. Additionally, to facilitate understanding of the invention, a number of terms are defined herein.

The term, "sample" as used herein refers to any substance containing or presumed to contain a nucleic acid of interest, and thus includes a sample of nucleic acid, cells, organisms, tissue, fluids (e.g., spinal fluid or lymph fluids), and sample including but not limited to plasma, serum, urine, tears, stool, respiratory and genitourinary tracts, saliva, fragments of different organs, tissue, blood cells, samples of in vitro cell cultures, isolates natural from natural sources such as drinking water, microbial specimens, and objects or specimens that have been suspected to contain nucleic acid molecules.

The terms, "target nucleic acid" or "nucleic acid of interest" refers to a nucleic acid or a fragment of nucleic that is to be amplified and detected using one or more methods of the present invention. Two or more target nucleic acids can be, for example, fragments of the same nucleic acid molecule or of different nucleic acid molecules. As used herein, target nucleic acids are different if they do not match in nucleotide sequence by at least one nucleotide. In this aspect, aspects of the invention may be used to detect polymorphic variations wherein, for example, two nucleic acids of interest have a significant degree of identity in the sequence but differ by few nucleotides (e.g. insertions, deletions) or by a single nucleotide (SNP). The target nucleic acids of the present inventive aspects may be derived from any organism or other source, including but not limited to prokaryotes, eukaryotes, plants, animals, and viruses, as well as synthetic nucleic acids. The target nucleic acids may contain DNA, RNA, and/or variants or derivatives thereof. Target nucleic acids can be single-stranded or double-stranded, and when a nucleic acid of interest is, or presumed to be double-stranded, the term "target nucleic acid" refers to a specific sequence in either strand of the double-stranded nucleic acid. Therefore, a full complement to any single-stranded nucleic acid of interest is treated for particular embodiments herein as the same target nucleic acid. In certain embodiments, the "target nucleic acid" resides between two primer sequences used for amplification and detection. Either one of the two DNA strands may be named herein as a "sense" strand while another (complementary) strand is called an "antisense" strand. This definition is used only for purpose of distinguishing two strands during the discussion and it does not mean assigning to the DNA strand any special property. In particular aspects, the nucleic acid of interest is isolated and purified from a sample source before applying methods of the present invention. Preferably, the target nucleic acids are sufficiently free of proteins and/or any other substances that interfer with the inventive amplification and detection reactions. Many art recognized methods are available for the isolation and purification of target nucleic acids, including commercial kits and specialty instruments. For example, nucleic acids can be isolated using organic extraction with a phenol/chloroform organic reagent followed by ethanol precipitation (Ausubel et al., eds., Current Protocols in Molecular Biology Vol. 1, Chapter 2, Section I, John Wiley & Sons, New York (1993). Solid phase adsorption method (Walsh et al. (1991) Biotechniques, 10:506-513, Boom et al., U.S. Pat. No. 5,234,809) and salt-induced DNA precipitation (Miller et al (1988) Nucleic Acids Res., 16:1215) are yet other known approaches to purify nucleic acids. Typically, amounts of nucleic acids of interest present in samples are limited, and the target nucleic acid needs, therefore, to be amplified using a suitable amplification procedure to facilitate detection using the inventive methods.

The terms "amplification" and "amplifying" a target nucleic acid as used herein refers to a procedure wherein multiple copies of the nucleic acid of interest are generated, for example, in the form of DNA copies. Many methods and protocols are known in the art to amplify target nucleic acids. The resent invention comprises use of PCR to amplify the nucleic acids of interest.

The term "amplicon" or "amplification product" as used herein refers to a product or products of PCR that may be a population of polynucleotides, single or double stranded, that are replicated from one or more nucleic acids of interest. If primer extension in PCR is efficient, amplicons are usually in form of a double-stranded duplex at the end of the extension stage. To initiate the next round of extension, double-stranded amplification products are preferably denatured at temperature >90° C. Either strand of the double stranded PCR product whether in single state or in the duplex is treated herein as amplification products including the products of incomplete extension. The amplicon sequences are generally defined by the oligonucleotide primers which are incorporated into the amplification products during PCR. Amplicons of the invention "fold into a secondary structure" when they are in a single-stranded state. The secondary structure is provided by the design of oligonucleotide primers which incorporate a 5'-'specialty sequence.' These amplicons are key components for the nucleic acid detection in the methods of the present invention. Amplicons of the invention may additionally contain certain structural nucleotide modifications, if their presence is required or useful for providing DNAs with specific properties, e.g. enhanced or improved hybridization properties. For example, the PCR amplification products may incorporate deoxyuridine (dU) monomer using a respective dUTP in the reaction mixture. A primary purpose of the dU application is in preventing contamination carryovers from sample to sample as described in Gelfand D. H. et al (1995) U.S. Pat. No. 5,418,149.

The terms "complementary" or "complementarity" are used herein in reference to the polynucleotides base-pairing rules. DNA consists of two base pairs wherein, for example, G forms a three hydrogen bonds complex or pair with C and A forms a two hydrogen bonds complex with T and it is said herein that G is complementary to C and A is complementary to T. In this sense, for example, an oligonucleotide 5'-GATTTC-3' is complementary to the sequence 3'-CTAAAG-5'. Complementarity may be "partial" or "complete." In partial complementarity only some of the nucleic acids bases are matched according to the base pairing rules. The degree of complementarity between nucleic acid strands has significant effects on the strength of hybridization between nucleic acids. This is particularly important in performing amplification and detection reactions that depend upon nucleic acids binding. The terms may also be used in reference to individual nucleotides and oligonucleotide sequences within the context of polynucleotides. As used herein, the terms "complementary" or "complementarity"

refer to the most common type of complementarity in nucleic acids, namely Watson-Crick base pairing as described above, although the oligonucleotide components and amplification products of the invention may participate, including an intelligent design, in other types of "none-canonical" pairings like Hoogsteen, wobble and G-T mismatch pairing.

The term "secondary structure" refers to an intramolecular complex formation of one sequence in a polynucleotide with another sequence in the same polynucleotide due to a complete or partial complementarity between these two sequences. Unless contextually specified otherwise, the term "complex" means the same as "duplex" and it represents a double stranded fragment of a nucleic acid formed on the principal rules of the Watson-Crick base pairing. The terms "hairpin" structure or "stem-loop" structure may be also used here in describing the secondary structure elements and both terms refer to a double-helical region (stem) formed by base pairing between complementary sequences in a single strand RNA or DNA. The present invention is based on providing amplicons that fold into secondary structures, and these structures actively participate in nucleic acid detection (e.g, FIGS. 5-8, 10-13). These secondary structures are created deliberately by the design of oligonucleotide primers carrying 5'-specialty sequences (e.g., FIG. 9).

The term "homology" and "homologous" refers to a degree of identity between nucleic acids. There may be partial homology or complete homology.

"PCR" is an abbreviation of term "polymerase chain reaction," the nucleic acids amplification technology used in all preferred methods of the present invention, and which was originally discovered and described by Mullis K. B. et al, U.S. Pat. No. 4,683,195 and Mullis K. B., U.S. Pat. No. 4,683,202. The commonly used PCR profile employs two oligonucleotide primers for each strand that are designed such as extension of one primer provides a template for another primer in the next PCR cycle. Either one of a pair of oligonucleotide primers may be named herein as a "forward" or "reverse" primer with the purpose of distinguishing the oligonucleotide primers in discussion. Generally, a PCR consists of repetition (or cycles) of (i) a denaturation step which separates the strands of a double stranded nucleic acid, followed by (ii) an annealing step, which allows primers to anneal to positions flanking a sequence of interest; and then (iii) an extension step which extends the primers in a 5' to 3' direction thereby forming a nucleic acid fragment complementary to the target sequence. Each of the above steps may be conducted at a different temperature using an automated thermocycler. The PCR cycles can be repeated as often as desired resulting in an exponential accumulation of a target DNA fragment whose termini are usually defined by the 5' ends of the primers used. Certain exceptions to this rule may apply, including those described herein. Particular temperatures, incubation time at each step and rates of change between steps depend on many factors well-known to those of ordinary skill in the Art and the examples can be found in numerous published protocols, for example, McPherson M. J. et al. (1991 and 1995) and the like. Although conditions of PCR can vary in a broad range, a double-stranded target nucleic acid may be denatured at temperature >90° C., primers annealed at a temperature in the range 50-75° C., and the extension is preferably performed in the range 72-78° C.

The cycle time of the PCR is usually less than 5 minutes and even more commonly less than 2 minutes. In preferred embodiments of the invention, oligonucleotide components of the assays are designed to perform at elevated annealing temperatures >65° C. or even >70° C. The increase of the annealing temperatures to the temperature range (72-75° C.) which is optimal for thermostable DNA polymerases improves productivity and specificity of PCR and it allows "merging" the annealing and extension stages. Thus, in preferred embodiments, PCR is performed in two stages, (i) strand denaturation and (ii) annealing/extension stage (combined). The number of the PCR cycles that is necessary to provide a detectable target nucleic acid concentration depends on the initial target nucleic acid load which is commonly unknown. A PCR time/temperature profile can be shown herein, for example, as 95°2'→(95°10"→65°45")$_{55}$ and this means that a PCR reaction was exposed to 95° C. for 2 minutes followed by 55 cycles of PCR where a cycle consist of a heating stage at 95° C. for 10 seconds and annealing/extension for 45 seconds at 65° C. The term "PCR" encompasses derivative forms of the reaction, including but not limited to, "RT-PCR," "real time PCR," "nested PCR," "quantitative PCR," "multiplexed PCR," "asymmetric PCR" and the like. These derivative forms may be used in practicing methods of the invention.

When nucleic acid of interest is RNA, it can be converted prior to PCR to DNA/RNA heteroduplexes or to duplex cDNA by known methods, for example, described in Simpson D. et al (1988) *Biochem. Biophys. Res. Commun.*, 151: 487-492 and Belyaysky A. et al (1989) *Nucleic Acids Res.*, 17: 2919-2932 and the like. These methods employ a "reverse transcriptase" activity of enzymes that can extend an oligonucleotide primer hybridized to a RNA template providing synthesis of complementary DNA (cDNA) in presence of deoxynucleoside 5'-triphosphates (dNTPs); that is, "reverse transcription PCR" or "RT-PCR" and it is also described in a U.S. Pat. No. 5,168,038 of Tecott L. et al (1992), which patent is incorporated herein by reference. Certain thermostable DNA polymerases express the reverse transcriptase activity, e.g. described in Myers T. W. and Gelfand D. H. (1991) *Biochemistry*, 30: 7661-7666, and both stages, cDNA synthesis and PCR, may be performed in the same reaction mixture.

In certain preferred embodiments, detection of the target nucleic acids can be performed in "real time." Real time detection is possible when all detection components are available during the amplification and the reaction conditions (e.g., temperature, buffering agents to maintain pH at a selected level, salts, co-factors, scavengers, and the like) support both stages of the reaction, amplification and the detection. This permits a target nucleic acid to be measured as the amplification reaction progresses decreasing the number of subsequent handling steps required for the detection of amplified material. "Real-time PCR" means a PCR for which the amount of reaction product, i.e. target nucleic acid, is monitored as the reaction proceeds. Real-time PCR differ mainly in the detecting chemistries for monitoring the target nucleic acids in the reaction, for example, Gelfand et al, U.S. Pat. No. 5,210,015 describe use of 5'-nuclease cleavable FRET probes ("TaqMan"); Tyagi et al, U.S. Pat. No. 5,925,517 use hybridization-triggered FRET probes ("Beacons") which patents are incorporated herein by reference. Reviews of the detection chemistries for real time PCR can be also found in Didenko V. V. (2001) *BioTechniques*, 31, 1106-1121; Mackay I. M. et al (2002) *Nucleic Acids Res.*, 30: 1292-1305, and Mackay J., Landt O. (2007) *Methods Mol. Biol.*, 353: 237-262, which are also incorporated herein by reference. In preferred embodiments of the present invention, detection of nucleic acids is also based on use of FRET effect and FRET probes. The detection is provided by a strand specific cleavage of three-strand cleavage structures which are formed by amplification products which folds into a secondary structure and, in certain embodiments, hybridized to oligonucleotide cleavage components. Placing the FRET dyes on opposite sides of the cleavage point permanently disrupt the FRET providing a detectable fluorescent signal.

In certain aspects, the amplification and detection stages may be performed separately, not in real time, when the detection stage follows the PCR amplification. The term "post-PCR detection" is used herein to describe such assays. For example, Endonuclease IV from *E. coli* does not survive at elevated temperatures of PCR and it can be added to the reaction mixture, as may be said herein "post-PCR," to initiate the detection.

The term "nested PCR" as used herein refers to a two-stage PCR wherein the amplification product of a first PCR becomes the sample for a second PCR using a new set of primers, at least one of which binds to an interior location of the amplification product of first PCR.

The term "multiplexed PCR" as used herein refers to a PCR wherein multiple target nucleic acids are simultaneously amplified and detected. Usually, this PCR employs sets of target-specific primers for each sequence being amplified.

The term "quantitative PCR" as used herein means a PCR designed to measure the abundance of one or more specific target sequences in a sample. Quantitative measurements are made using one or more reference nucleic acid sequences which may be assayed separately or together with a target nucleic acid. Techniques for quantitative PCR are well-known in the art and they are exemplified in the following manuscripts that are incorporated herein by reference: Gu Z. et al (2003) *J. Clin. Microbiol.*, 41:4636-4641; Becker-Andre M. and Hahlbrock K. (1989) *Nucleic Acids Res.*, 17:9437-9446; Freeman W. M. et al (1999) *Biotechniques*, 26:112-122, 124-125; Lutfalla G. and Uze G. (2006) *Methods Enzymol.*, 410:386-400; Clementi M. et al (1993) *PCR Methods Appl.* 2:191-196; Diviacco S. et al (1992) *Gene*, 122:313-320.

"Asymmetric PCR" refers to a PCR when concentrations of oligonucleotide primers for any particular target amplification are not equal. For example, one of pair PCR oligonucleotide primers is used at 100 nM in the reaction mixture while another primer is applied at 200 nM concentration. The oligonucleotide primers have commonly the same concentration in PCR ("symmetric PCR"). In certain cases, it may be advantageous for the detection assay to increase the yield of one amplicon strand over the complementary strand then the oligonucleotide primer providing this strand in PCR is taken in a molar excess over another primer of the target pair. Both, symmetric and asymmetric approaches may be used in methods of the invention.

The term "fluorescent agent" means a detecting agent that provides a fluorescence signal. The preferred fluorescent agents are those molecules that change fluorescence properties upon the interaction with nucleic acids providing detectable signal. SYBR Green I and II from Invitrogen are examples of commonly used fluorescent agents as described in Schneeberger C. et al (1995) *PCR Methods Appl.*, 4:234-238 and Mackay J., Landt O. (2007) *Methods Mol. Biol.*, 353:237-262.

The term "polynucleotide" and "oligonucleotide" are used interchangeably herein, and each means a linear polymer of nucleotide monomers. Polynucleotides typically range in size from a few monomeric units, e.g. 5-40, when they are usually referred to as "oligonucleotides," to several thousand monomeric units. The exact size will depend on many factors, which in turn depends on the ultimate function or use of the oligonucleotide. The oligonucleotide may be generated in any manner, including chemical synthesis, DNA replication, reverse transcription, or a combination thereof. Whenever a polynucleotide or oligonucleotide is represented by a sequence of letters, for example, "CCGTATG," it is understood herein, unless otherwise specified in the text, that the nucleotides are in 5'→3' order from left to right and that "A" denotes deoxyadenosine, "C" denotes deoxycytidine, "G" denotes deoxyguanosine, and "T" denotes deoxythymidine, unless otherwise indicated or obvious from context. Usually DNA polynucleotides comprise these four deoxyribonucleosides linked by phosphodiester linkage whereas RNA comprise four their ribose counterparts with uridine ("U") in place of "T".

The term "oligonucleotide component" refers to any molecule of the polynucleotide nature that is required or helpful in conducting either amplification or detection reaction of the invention or both. Oligonucleotide components include but not limited to oligonucleotide primers, probes, hybridization and cleavage enhancers, oligonucleotide cleavage components, effectors, etc. Oligonucleotide components can be labeled or have structural modifications of any kind.

Figure 2:
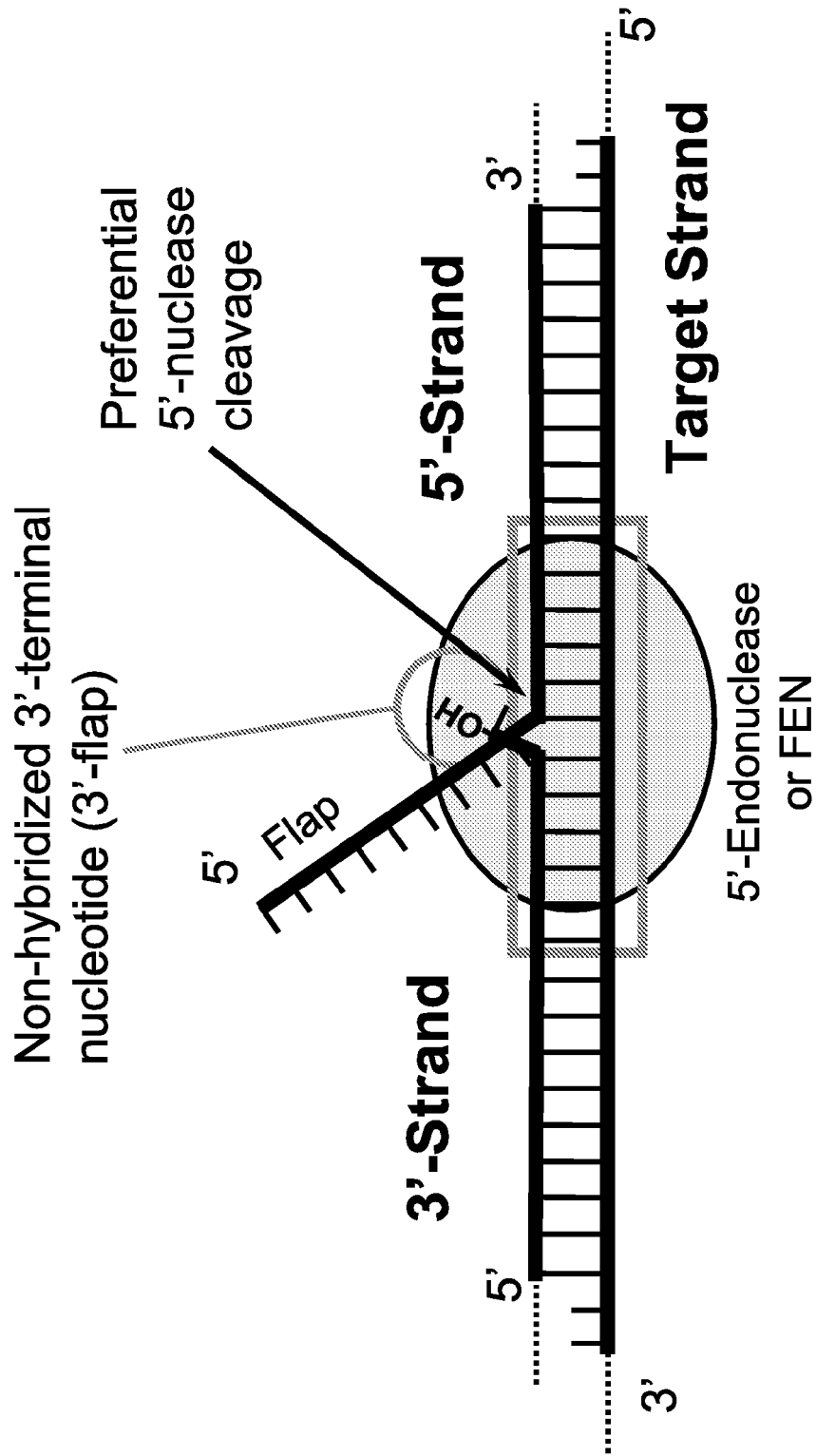
FIG. 2 shows a schematic diagram of an optimal three-strand cleavage structure for practicing 5'-nuclease assays of the invention. Two duplexes are formed without a target strand gap. The 3'-strand contains a single nucleoside flap which is an important element for the 5'-endonuclease recognition and binding. The presence of an "unblocked" 3'-hydroxyl group is important. The arrow points to a phosphodiester bond between the first and second hybridized nucleosides of the 5'-strand, preferably hydrolyzed by the enzyme. The presence of the 5'-flap is optional but a cleaved flap may be detected in certain methods of the invention (e.g., FIG. 10). Any structural duplex abnormalities within ~4-6 base pairs on either side of the duplex junction (shown by a grey box) may negatively affect the nuclease binding/cleavage and this property can be used in detecting (discriminating) polymorphic variations in nucleic acids of interest.
Figure 6:
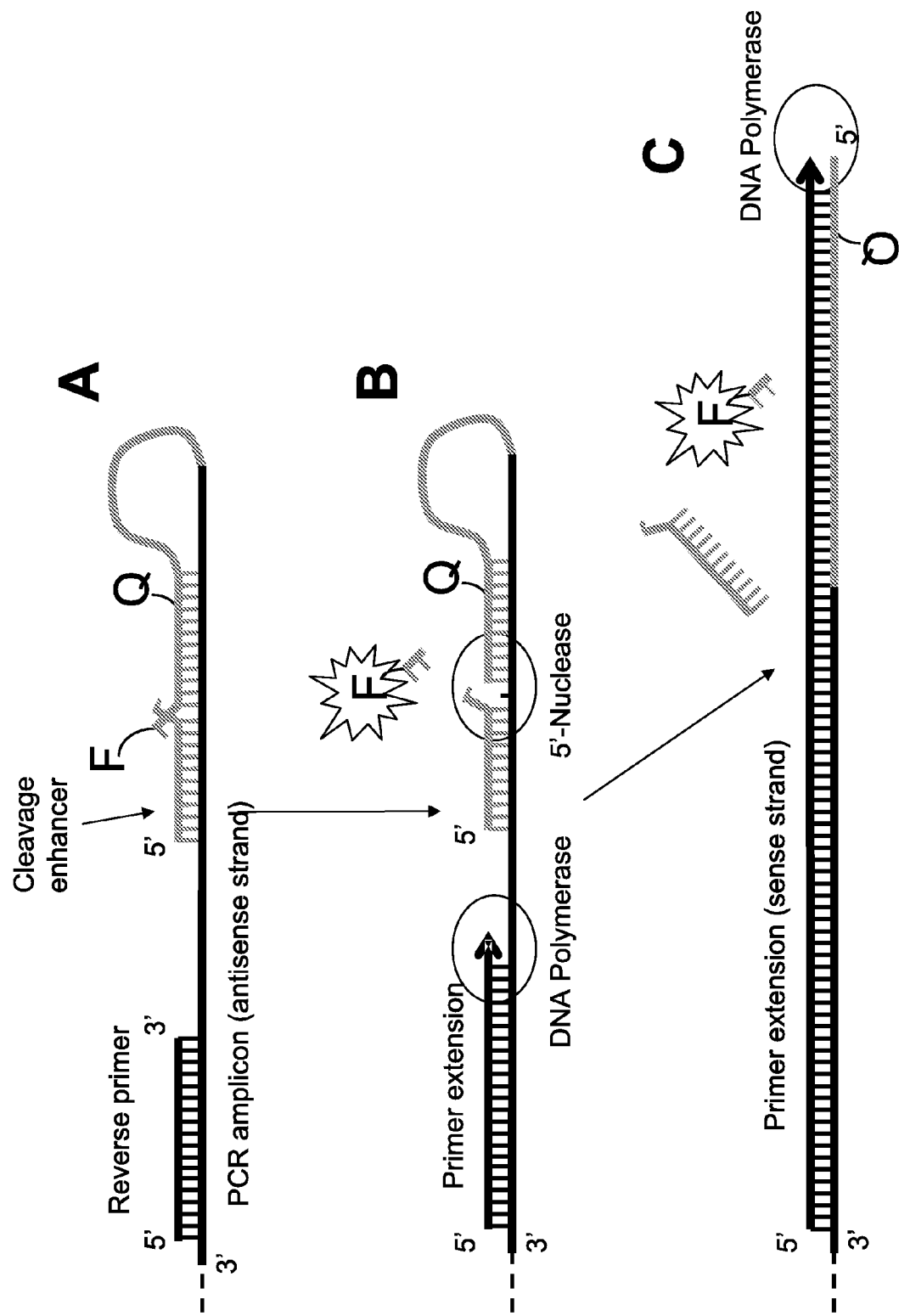
FIG. 6 shows an exemplary method of the invention that is similar in many aspects to that shown in FIG. 5, but with a principal difference. The three-strand cleavage structure in the method of FIG. 5 is formed during the strand extension and thus the cleavage may take place within a short period of time while the DNA polymerase extension complex reaches the hybridized specialty strand and initiates its cleavage/displacement. By contrast, the method shown in this figure employs an additional oligonucleotide component, a 'cleavage enhancer.' An antisense amplicon which incorporates the specialty primer folds into a secondary structure (stage A). The cleavage enhancer binds next to the duplex formed by a FRET-labeled specialty sequence. Collectively this complex represents an optimal cleavage structure effectively recognized and cleaved by 5'-nuclease or FEN (stage B). In this design, the structure-specific cleavage does not directly depend on the strand extension and it can happen at any time before a reverse primer hybridizes to the amplicon initiating the complementary strand synthesis and the extension complex reaches the three-strand cleavage structure in stage B. The extension complex eventually passes/displaces the components of the cleavage structure providing a full length double stranded amplicon in stage C. In this approach, the structure-specific cleavage reaction may take place after the PCR amplification stops, e.g. due to "consumption" of all oligonucleotide primers. The specialty FRET-primer shown in this embodiment does not incorporate a none-extendable linker "X." Thus, to avoid potential problems described in the context of FIG. 12, it is designed to carry a single nucleotide 5'-flap.
Figure 7:
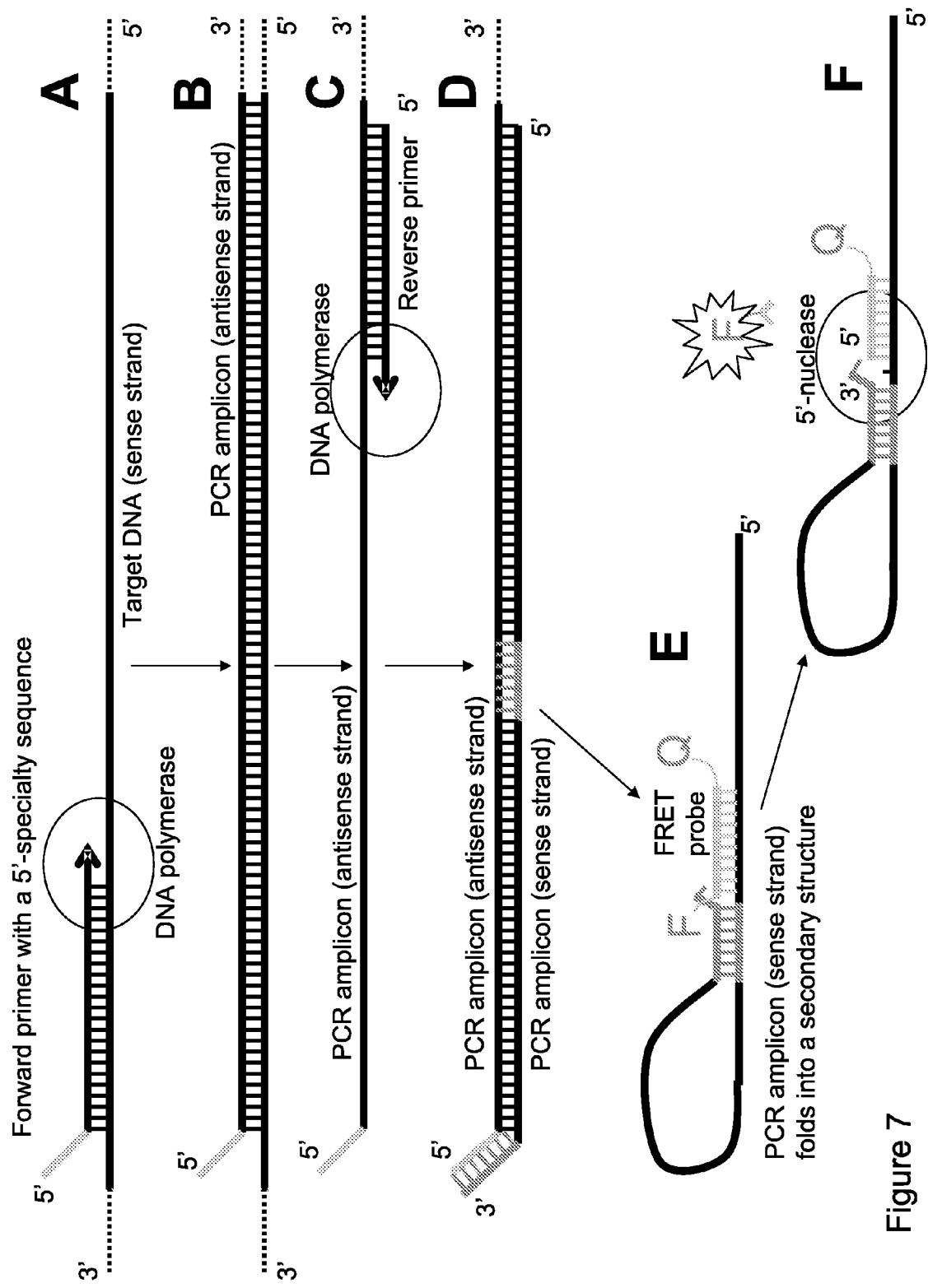
FIG. 7 shows another method embodiment of the invention that is based on the use of a 5'-nuclease activity. A forward oligonucleotide primer contains a 5'-specialty sequence (shown in gray color) wherein the primer template and specialty sequences represent an uninterrupted chain of nucleotides. Extension of this specialty primer in stage A results in synthesis of an antisense strand providing a double stranded amplicon (stage B). After the strand separation (e.g., 95° C.), a reverse primer hybridizes to the antisense strand and DNA polymerase extends the complex (stage C) resulting in yet another double stranded amplicon (stage D). Since the specialty primer is fully extendable (does not incorporate a none-extendable linker), a full complement to the forward primer specialty sequence appears at the 3'-end of a sense amplicon strand. After another round of strand separation, the sense amplicon (synthesized in stage D) folds into a secondary structure carrying a single nucleoside 3'-flap (stage E). A FRET probe is designed to bind to this amplicon next to the secondary structure duplex forming an optimal three-strand cleavage structure as shown in the stage E. A 5'-nuclease recognizes the structure and cleaves the probe strand disrupting the FRET and proving a detectable fluorescent signal in stage F. In this method, unlike in other methods of the invention, the detected amplicon is not the one which incorporates the specialty primer sequence but rather its replica, which also folds into a secondary structure. The method shown in this figure may be performed in a cycling mode when more than one probe is cleaved per target amplicon molecule. This may be achieved, for example, by providing a molar excess of the oligonucleotide probe over amounts of the respective oligonucleotide primers used in amplifying a nucleic acid of interest.
Figure 10:
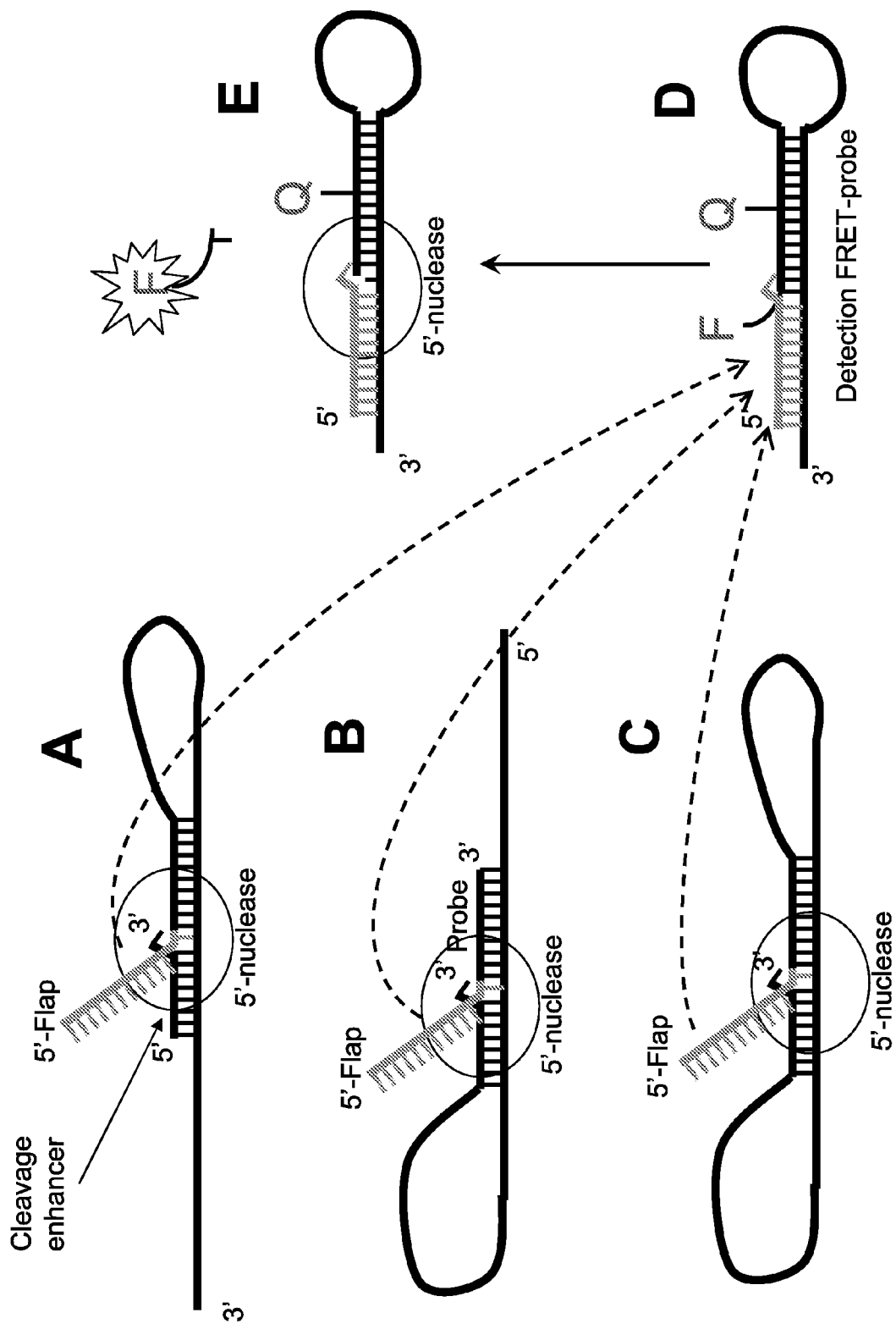
FIG. 10 shows diagrammatic examples of embodiments of the invention wherein a detectable cleavage product is an oligonucleotide sequence. A 5'-flap sequence is cleaved by a 5'-nuclease in three optimal cleavage structures A, B and C of the invention and this oligonucleotide fragment serves as a 'cleavage enhancer' in a subsequent reaction D, forming another three-strand optimal cleavage structure with a hairpin-type FRET probe. Cleavage of this complex results in a detectable fluorescent signal as shown in stage E.
Figure 11:
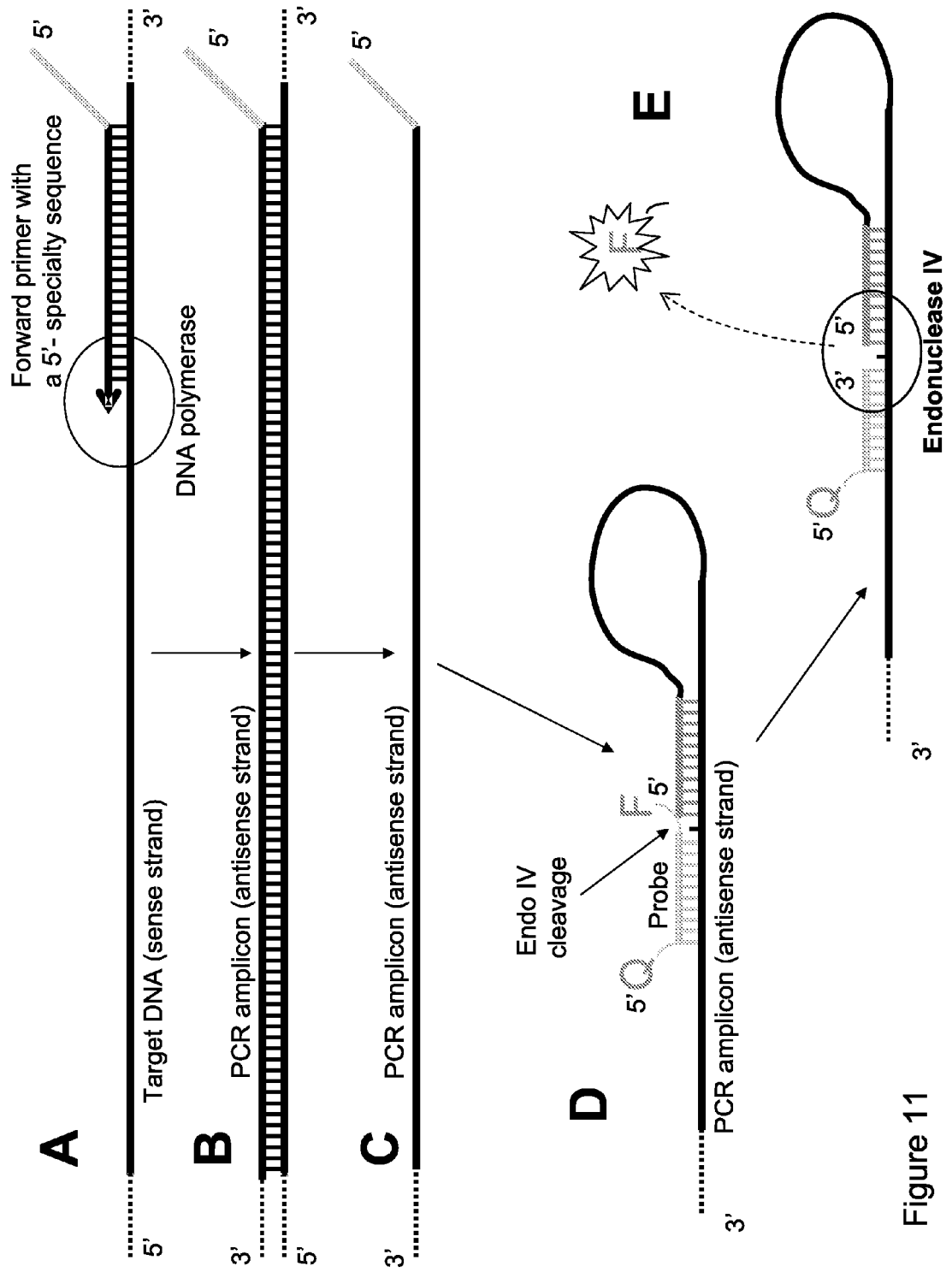
FIG. 11 shows an embodiment of the inventive 3'-nuclease assay. A forward primer carrying a 5'-specialty sequence hybridizes to a sense strand of a target DNA (stage A). A DNA polymerase recognizes the complex and extends the primer resulting in a double stranded amplicon (stage B). When the antisense strand is separated from its complement (stage C), it folds into a secondary structure. A FRET probe is designed to form a duplex with a respective site of the amplicon such as the duplex is separated from the amplicon duplex structure by one target strand nucleotide (stage D). These two duplexes collectively form an optimal three-strand cleavage structure which is recognized and cleaved by a 3'-nuclease, Endonuclease IV (stage E), providing a detectable fluorescent signal. The FRET probe is designed to carry a reporter dye "F" at the 3'-end whereas a quencher "Q" is attached to the 5'-end.

As used herein, the term "oligonucleotide cleavage component" refers to a molecule of the polynucleotide nature which hybridizes to an amplification product of the invention that folds into a secondary structure generating a three-strand cleavage structure, examples of which may be found in FIGS. 6, 7, 10 and 11. The three-strand cleavage structure is cleaved in presence of a "duplex-specific nuclease" generating a detectable cleavage product. In certain aspects, the oligonucleotide cleavage component is not the cleaved strand. Then it may be referred herein as a "cleavage enhancer" (FIGS. 6 and 10). In other aspects, the oligonucleotide cleavage component represents the strand that is cleaved. In such cases, it may be named herein as an "oligonucleotide probe" or "probe" (FIGS. 7, 10 and 11). The core structure and specific structural elements of the oligonucleotide cleavage component is determined by a specific method of the invention. For example, when the oligonucleotide cleavage component serves as a cleavage enhancer in a 5'-nuclease assay, it is substantially complementary to an amplicon site that is in proximity to the specialty sequence binding site, preferably forming an optimal three-strand cleavage structure as shown in FIG. 2. In preferred aspects, the 3'-nucleotide of the cleavage enhancer is not in a complex with the target counterpart. This can be readily achieved, for example, when an unnatural or modified nucleotide, e.g. universal base, is incorporated to the 3'-end of the cleavage enhancer. In certain embodiments, when Endonuclease IV is used to cleave the three-strand cleavage structure, oligonucleotide cleavage component is an oligonucleotide probe which carries a 3'-tail, the cleavage of which is detected in the assay (FIG. 11). In a preferred aspect of the invention, the tail contains a fluorescent dye which is in a FRET interaction with a quencher dye located at the 5'-end of the oligonucleotide probe. In addition to dyes, universal bases and linkers, the oligonucleotide cleavage components of the invention may contain other structural modifications like modified bases, including the duplex-stabilizing ones, conjugated intercalators, minor groove binders, etc.

Figure 1:
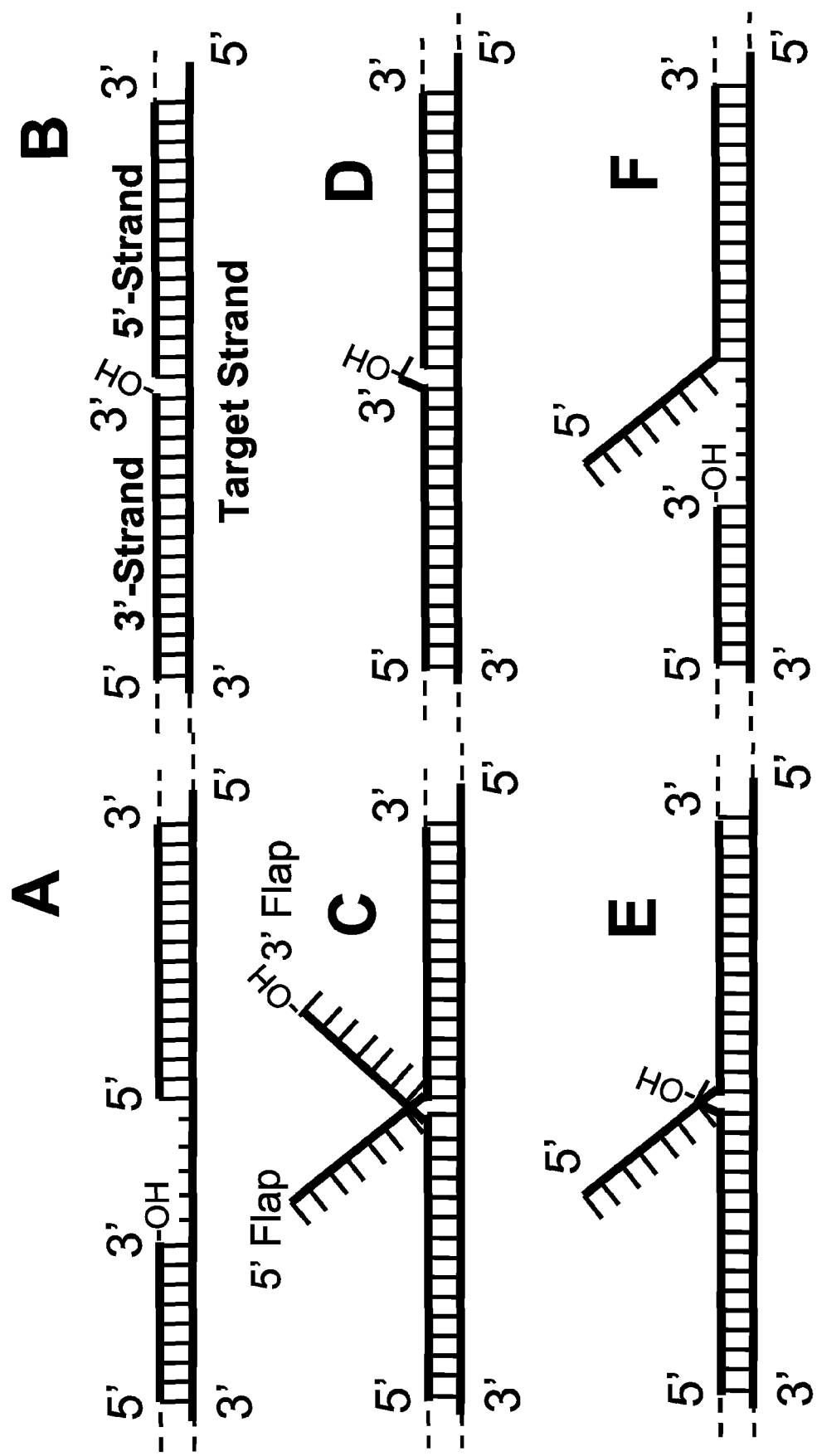
FIG. 1 shows examples of the 'three-strand' cleavage structures that are formed in methods of the invention. A 'three-strand cleavage structure' refers to a duplex structure wherein two oligonucleotide sequences anneal to neighboring regions of the same linear complementary nucleic acid sequence. The strands are defined by specific names as shown in the structure B: target strand, 3'-strand, and 5'-strand. The symbol "—OH" represents 3'-hydroxyl group of a 3'-terminal nucleoside of the 3'-strand. Two duplexes in the "three-strand cleavage structures" can be separated by ten and preferably less then five nucleotides of a "target strand" as shown in structures A and F. The three-strand cleavage structures may incorporate either "3'-flap" (structures C, D and E) or "5'-flap" (structures C, E and F) sequences. The flap sequences may or may not be complementary to the target strand. The three-strand cleavage structures of the invention exemplified here are formed wherein at least two of the strands, e.g. the target strand and 5'-strand or the target strand and 3'-strand, are provided by a PCR amplification product. In certain embodiments, all three strands of a cleavage structure are provided by a PCR amplicon. Either 3'- or 5'-strands may be cleaved in methods of the invention.
Figure 4:
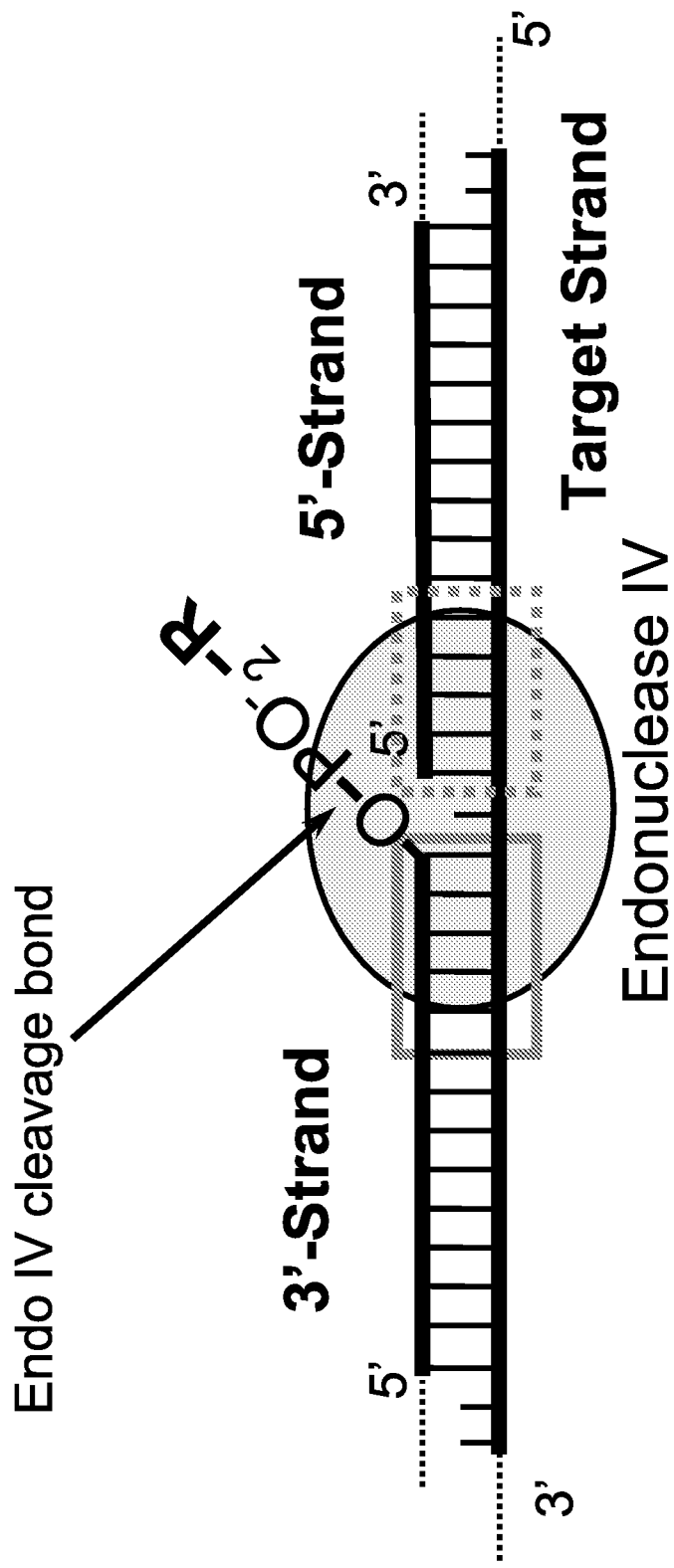
FIG. 4 shows a schematic diagram of an Endo IV optimal cleavage (see also Kutyavin I. V. et al (2004) US Patent Application #20040101893; Kutyavin I. V. et al (2006) Nucleic Acids Res., 34: e128 and references cited therein). Endonuclease IV cannot cleave an internucleotide phosphodiester bond unless a nucleoside which is 3'- to this bond is damaged, e.g. a nucleoside base is missing (abasic site). The enzyme is duplex-specific but the presence of another duplex nearby the cleaved strand significantly accelerates the tail cleavage. An optimal substrate shown here simulates a partially "degraded" abasic site of two duplexes separated with one base target gap. Decrease (no gap) or increase in the gap length was shown to reduce the Endo IV activity. The endonuclease recognizes the substrate and cleaves a 3'-tail (—PO-2-R) between the 3'-deoxyribose oxygen and phosphor atoms initiating the DNA repair process. The enzyme is particularly sensitive to structural abnormalities like single base mismatches (SNPs), insertions or deletions within ~4-6 base pairs duplex (solid grey box) counting from the terminal nucleotide of the 3'-strand. Mismatches within the 5'-strand duplex (broken grey box) may also affect the substrate properties but with a lesser degree.

As used herein, the term "three-strand cleavage structure" refers to a duplex structure when two oligonucleotide sequences anneal to neighboring regions of the same linear complementary nucleic acid sequence. Examples of the three-strand cleavage structures of the invention are shown on FIG. 1. Duplex-specific nucleases can cleave a two-strand duplex with certain degree of efficiency but, in many occasions, the cleavage rate significantly increases when yet another duplex structure appears in proximity forming a three-strand cleavage structure. Two duplexes in the three-strand cleavage structures can be separated by ten and preferably less then five nucleotides of a "target strand" which are not involved in complementary binding. The three-strand cleavage structures may incorporate "flap" sequences at the strand ends which in certain aspects may be, at least partially, complementary to the target strand. In the present invention, at least two of the three-strand cleavage structure, the target strand and one of the 3'- or 5'-strands, are provided by a PCR amplification product. In certain aspects, the PCR amplicon folds in to a secondary structure providing all three strands of the three-strand cleavage structure. Preference in the choice of cleaved structure depends on number of factors but mainly on the substrate properties of duplex-specific nucleases used in methods of the invention. The optimal (preferred) three-strand cleavage structures for 5'-endonuclease and for 3'-endonuclease assays are shown in FIGS. 2 and 4 respectively. Although the cleavage rate is usually maximum in the optimal three-strand cleavage structures, all of the structures exemplified in FIGS. 1 and 2 are within a scope of the present invention. For example, as has been shown by Lyamichev V. et al (1993) Science, 260: 778-783, many "suboptimal" cleavage structures shown in FIG. 1 may rearrange forming somewhat "optimal" three-strand cleavage structures with minor structural abnormalities. The terms "optimal" and "suboptimal" cleavage structures are used herein to indicate a degree of preference in use providing that the optimal structures are the preferred ones. It is understood herein that both strands of the three-strand structures are sufficiently complementary to the target strand, although a non-complementary nucleotide or longer sequences can be interspersed into the duplexes. In preferred aspects, 4-6 nucleotides at the 3'-end of the 3'-strand and at the 5'-end of the 5'-strand are in a perfect complementary match with the respective target strand sequences. The sensitivity of the duplex-specific nucleases to the duplex structures within these regions may be used in certain aspects to discriminate and to detect small polymorphic variations like SNP.

As used herein, the term "nuclease" refers to an enzyme which expresses a phosphomonoesterase or phosphodiesterase activity and capable of cleaving a phosphorester bond in compounds R'—O—P(O)(OH)$_2$ and R'—O—P(O)(OH)—O—R" resulting in products R'—OH+P(O)(OH)$_3$ and R'—OH+P(O)(OH)$_2$—O—R" (or R"—OH+P(O)(OH)$_2$—O—R'), respectively, and wherein R' and R" may be moieties of any structure which are not necessarily of a nucleotide nature.

The term "duplex-specific nuclease activity" refers to enzymes that recognize specific DNA duplex structures and cleave these structures. The duplex-specific nucleases useful in practicing the invention do not substantially cleave either oligonucleotide probes or primers when they are in a single stranded state and when they are not hybridized to the target nucleic acids or PCR amplicons. The term "duplex-specific endonucleases" incorporate both "exo" and "endo" nucleases. Cleavage efficiency of duplex-specific nucleases of the invention in many occasions is significantly improved when yet another duplex structure appears in proximity of their cleavage site. This property of the endonucleases is used herein in cleaving the three-strand cleavage structures in PCR detection assays. Examples of the three-strand cleavage structures of the invention are shown in FIGS. 1-4. The duplex-specific nucleases may be divided on two main classes, "5'-nucleases" and "3'-nucleases" (5'- or 3'-nuclease activities respectively). 5'-Nucleases cleave 5'-strand of the three-strand cleavage structures while 3'-nucleases cleave the 3'-strand. Duplex-specific 5'-nuclease activities useful in practicing the invention may be found in many DNA polymerases, e.g. *E. coli* DNA polymerase I and DNA polymerase isolated from *Thermus aquaticus* (Taq), *Thermus thermophilus* (Tth), *Pyrococcus furiosus* (Pfu) and *Thermus flavus* (Tfl).

Figure 3:
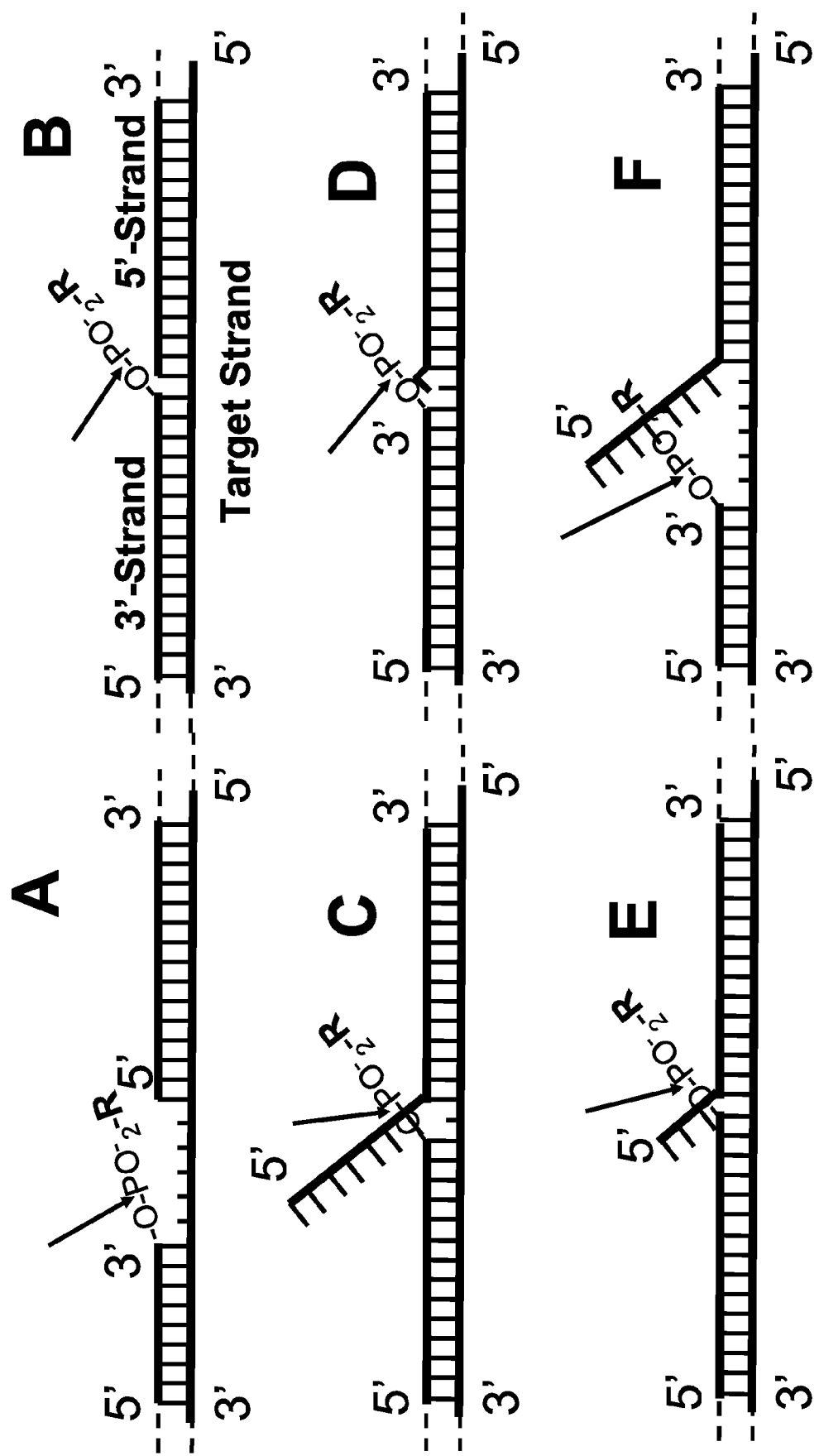
FIGS. 3A-3F shows examples of three-strand cleavage structures that may be used in 3'-nuclease assays of the invention. The three-strand cleavage structures are formed herein between a PCR amplicon and oligonucleotide probe carrying a —PO-2-R tail wherein R is a detectable label. In these cases, the amplicon folds into a secondary structure and provides a target strand and 5'-strand while an oligonucleotide probe provides a 3'-strand. The strand assignment is shown in structure B. Endonuclease IV (Endo IV) may be used in the inventive assays to provide a strand-specific cleavage of a 3'-tail in the shown structures. The arrows point to a hydrolyzed phosphodiester bond between a 3'-oxygen and phosphorous atoms of the tail. All examples of the three-strand cleavage structures shown in this Figure may be used in the 3'-nuclease assays of the invention with differing degrees of preference. An Endo IV optimal cleavage structure is shown in FIG. 4. Presence of a very short 5'-flap, e.g. structure D, is anticipated to have little, if any negative effect on the Endo IV activity but in certain derivative forms of the 3'-endonuclease assay presence of such short 5'-flaps may be important.

In certain preferred embodiments of the invention, both assay activities, DNA polymerase and 5'-nuclease, are provided by the same enzyme, for example, Taq polymerase. "Flap endonucleases" ("FENs") are yet another example of 5'-duplex-specific nucleases that may be used to cleave the three-strand structures of the invention. Flap endonucleases are a class of nucleolytic enzyme that acts as structure-specific 5'-exo and 5'-endonucleases during DNA replication, DNA repair and DNA recombination (Lyamichev V. et al (1993) Science, 260: 778-783). Flap endonucleases have been identified in eukaryotes, prokaryotes, archea and viruses. Optimal cleavage structures for 5'-nucleases and FENs are similar and one of such structures is shown on FIG. 2. Examples of 3'-duplex-specific nucleases include DNA repair enzymes. 3'-nucleases from Endo IV family of enzymes are in particular interest to this invention. For example, Endonuclease IV from *E. coli* does not cleave internucleotide phosphodiester bond but it efficiently cleaves a DNA strand in duplexes containing abasic cites and it also removes phosphates and other tails from the 3'-end of a three-strand cleavage structure as shown in FIGS. 3 and 4. Although the Endo IV is duplex-specific, presence of another duplex structure nearby the 3'-cleaved end was shown to accelerate the cleavage (Kutyavin I. V. et al (2004) US Patent Application #20040101893; Kutyavin I. V. et al (2006) *Nucleic Acids Res.*, 34: e128). The three-strand cleavage structures apparently simulate the 3'-endonuclease natural substrates commonly found in DNA lesions. Although Endonuclease IV from *E. coli* does not survive in PCR, use of methophilic endonucleases in post-PCR detection may be advantageous in certain aspects.

The term "polymorphic variations" refers to differences in nucleic acid sequence between two nucleic acids of interest. For example, two target nucleic acids can share a substantial degree of the sequence homology but they may vary in sequence by the presence of single base substitutions and/or deletions or insertions of one or more nucleotides. These two target nucleic acids that can be two genes are said to vary in sequence from one another and the target nucleic acid is said to have polymorphic variations.

The term "oligonucleotide primer" refers to a single-stranded DNA or RNA molecule that hybridizes to a target nucleic acid and primes enzymatic synthesis of a second nucleic acid strand in presence of a DNA polymerase. In this case, as used herein, the target nucleic acid "serves as a template" for the oligonucleotide primer. An "oligonucleotide primer" may occur naturally, as in a purified restriction digest or may be produced synthetically. A primer is selected to have on its 3' end a region that is substantially complementary to a strand of specific sequence of the template or target nucleic acid. The oligonucleotide primer sequence which is substantially complementary to a fragment of the template may refer herein as a "primer template sequence." A primer must be sufficiently complementary to hybridize with a template strand for primer elongation to occur. An oligonucleotide primer sequence does not need to reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template-primer complex for synthesis of the extension product of the oligonucleotide primer. Certain oligonucleotide primers of the invention may be designed applying conventional rules. At least one of a pair of oligonucleotide primers used in methods of the invention is "designed to incorporate a 5'-specialty sequence." As used herein, the specialty sequence is an oligonucleotide fragment that is substantially complementary to a target nucleic acid sequence and, in certain aspects, may be partially complementary to the primers template sequences or their target binding sites. In preferred embodiments, the target complement to the "5'-specialty sequence" is located between the sites of the primers binding. The sequence which is complementary to the "specialty sequence" is produced in PCR as result of the primer extension. Since the specialty primer is incorporated into the amplification product, this prompts the amplicon to fold into a (steam-loop) secondary structure, as exemplified in FIGS. 5-8 and 10-13. Examples of the specialty oligonucleotide primers of the invention are provided in FIG. 9. In certain embodiments, the primer template and specialty sequences may represent uninterrupted chain of nucleotides. When such an oligonucleotide primer is incorporated into an amplicon and the amplicon serves as a template in next PCR cycle, a DNA polymerase is capable to replicate the amplicon extending the complementary strand to the very 5'-end of the template including the sequence of this primer. Such an oligonucleotide primer is referred herein as a "fully extendable" oligonucleotide primer. In other embodiments, the 3'-end of the specialty sequence is coupled to the 5'-end of the primer template sequence through a "non-extendable linker" which does not support the strand extension by a DNA polymerase and the complementary strand synthesis is terminated once the polymerase reaches the 5'-end of the primer template sequence. These oligonucleotide primers are referred herein as "partially extendable" oligonucleotide primers. DNA polymerases are sensitive to the DNA template structure. Virtually any moiety or combination of moieties that are substantially different from the nucleotide structure may be used in the invention as "non-extendable linkers." Examples of such moieties include but not limited to the commercially available compounds commonly applied in oligonucleotide synthesis such as universal bases, abasic sites, and also propane diol, triethylene glycol, 4-butyramidomethyl-1-(2-nitrophenyl)-ethyl linkers (Glen Research) and the like. Another example is a hexaethylene glycol linker which is usually used for the same purpose in design of Scorpion primers as described in Whitcombe D. et al (1999) *Nature Biotech.*, 17: 804-807; Thelwell N. et al (2000) *Nucleic Acids Res.*, 28: 3752-3761. In certain embodiments when the fully extendable primers with 5'-specialty sequence are used, the amplicon which incorporates the primer may not be the detected amplification product. The detected PCR product may be its replica or other DNA strand which also folds into a secondary structure and this structure participates in forming a three-strand cleavage structure (FIG. 7). Oligonucleotide primers of the invention may incorporate sequences other than the specialty and primer template sequences. In such a case, these sequences are preferably positioned between the specialty and primer template sequences. In certain aspects, the oligonucleotide primers of the invention are cleaved once they are incorporated into amplicons which fold into a secondary structure resulting in detectable cleavage products as shown in FIGS. 5, 6, 8 and 10. Thus the oligonucleotide primers used herein may incorporate detectable elements like labels, e.g. dyes, mass tags, etc., or 5'-flap sequences. In cases when the detection is based on FRET effect, the oligonucleotide primers may be named herein as "FRET primers." The oligonucleotide primers used herein may also contain "structural modifications" that is used for reasons other than detection, for example, to improve the sequence hybridization properties (e.g. duplex-stabilizing modified bases).

As used herein, the term an "oligonucleotide probe" refers to an oligonucleotide cleavage component which is cleaved during the PCR assay and it represents an oligonucleotide that forms a duplex structure with a PCR amplicon, due to complementarity of at least one sequence in the probe with a sequence in the target nucleic acid (e.g. FIGS. 7, 10 and 11). The oligonucleotide probes of the invention incorporate detectable elements like labels, e.g. dye, mass tag, etc., or 5'-flap sequences. In certain aspects, the probe cleavage may be performed in a "cycling mode" when the target amplicon is said "recycled" and more than one probe can be cleaved per the target molecule (e.g. methods in FIGS. 7 and 11). This is usually the case when the probe concentration exceeds the concentration of the respective PCR primers which, in term, determine the yield of the detected amplicon. In preferred embodiments, the oligonucleotide probes contain two dyes which are in a FRET interaction and which are permanently separated due to the cleavage providing a detectable fluorescent signal. These probes may be also referred herein as "FRET probes." Similar to oligonucleotide primers, the oligonucleotide probes of the present invention may be "modified" or contain "structural modifications" that, e.g. enhance their hybridization properties, improve the binding specificity or stability in PCR, improve the cleavage or cleavage specificity, etc.

The term "structural modifications" refers to any chemical substances such as atoms, moieties, residues, polymers, linkers or nucleotide analogs which are usually of a synthetic nature and which are not commonly present in natural nucleic acids. As used herein, the term "structural modifications" also include nucleoside or nucleotide analogs which are rarely present in natural nucleic acids, and include but are not limited to inosine (hypoxanthine), 5-bromouracil, 5-methylcytosine, 5-iodouracil, 2-aminoadenosine, 6-methyladenosine, preudouridine and the like.

"Duplex-stabilizing modifications" refer to structural modifications, which when present in double-stranded nucleic acids provide duplex-stabilizing effects when compared in terms of thermal stability, usually measured as Tm, with the respective nucleic acid complexes that have no structural modification, e.g. comprising of natural nucleotides. Duplex-stabilizing modifications are structural modifications that are most commonly applied to the synthesis of oligonucleotide probes and primers. Those of ordinary skill in the art will appreciate that there are certain rules and limits to use of the structural modifications in oligonucleotide primers. The 3' end of the primers must not be blocked to allow for initiation of DNA synthesis. For example, when minor groove binders (MGB) are conjugated to enhance the primer hybridization properties, the MGB moiety is usually coupled to the 5' end (Afonina I. et al (1997) *Nucleic Acids Res.*, 25:2657-2660). Certain nucleotide analogs can be incorporated into the oligonucleotide primers, although the number of these modifications is limited. Examples of such nucleotide analogs include but not limited to "universal" bases (Burgner D. et al (2004) *Nucleosides Nucleotides Nucleic Acids*, 23:755-765) and "locked nucleic acids" ("LNA") (Latorra D. et al (2003) *Mol. Cell. Probes*, 17:253-259; Latorra D. et al (2003) *Hum. Mutat.*, 22:79-85; Di Giusto D. A. and King G. C. (2004) *Nucleic Acids Res.*, 32:e32), in accordance with teachings of the cited references which are incorporated herein by reference. Certain base-modified nucleotide analogs are well tolerated by DNA polymerases and these analogs can be used in primer design without any limits. Examples of such base-modified nucleotide analogs include but not limited to 5-methyl cytosine and 2,6-diamino purine (Lebedev Y. et al (1996) *Genet. Anal.*, 13: 15-21). Unlike the oligonucleotide primers, oligonucleotide probes may have no limits in use of the structural modifications. For example, according to Ortiz E. et al (1998) *Mol. Cell. Probes,* 12:219-226, the oligonucleotide probes can be completely made of unnatural "peptide nucleic acid" ("PNA") monomers; as these probes have no natural nucleotides in their structures. Application of other base-modified (Lebedev Y. et al (1996) *Genet. Anal.,* 13, 15-21) or sugar-modified nucleotide analogs like LNA (Johnson M. P. et al (2004) *Nucleic Acids Res.,* 32:e55; Simeonov A. and Nikiforov T. T. (2002) *Nucleic Acids Res.,* 30:e91) is also widely applicable to probes. Oligonucleotide probes can carry an MGB moiety conjugated at either end. For example, 5'-MGB-conjugated FRET probes are not cleaved in detection PCR and these probes provide a signal due to a hybridization-triggered mechanism of action as described in Vermeulen N. et al (2002) *J. Clin. Ligand Assay,* 25:268-275. By contrast, 3'-MGB-conjugated FRET probes are not blocked from 5'-nuclease degradation and these probes generate fluorescent signasl due to cleavage by Taq polymerase as exemplified in Kutyavin I. V. et al (2000) *Nucleic Acids Res.,* 28:655-661. This information can be used in design of the oligonucleotide probes of the invention. For example, if 5'-nuclease is used to cleave the three-strand cleavage structure and the probe provides the cleavable strand, MGB-moiety shell be conjugated to the 3'-end of the probe. In contrast, if 3'-nuclease, e.g. Endonuclease IV, is used for the same reason, the MGB-moiety shall be conjugated to the 5'-end of the probe. Placing the structural modifications within 4-6 nucleotides on either side from the cleavage point should be avoided unless the compatibility of a structural modification with a specific nuclease has been studied and verified. A list of the structural modifications that may be used in preparing oligonucleotide probes of the invention includes but not limited to PNA monomers (Ortiz E. et al (1998) *Mol. Cell. Probes,* 12, 219-226), 2,6-diamino purine and 5-methyl cytosine nucleotide analogues (Lebedev Y. et al (1996) *Genet. Anal.,* 13, 15-21), sugar-modified nucleotide analogs like LNA (Johnson M. P. et al (2004) *Nucleic Acids Res.,* 32: e55; Simeonov A. and Nikiforov T. T. (2002) *Nucleic Acids Res.,* 30: e91) and the like.

"Hybridizing," "hybridization" or "annealing" as used herein refers to a process of interaction between two or more polynucleotides forming a complementary complex through base pairing which is most commonly a duplex or double-stranded complex as originally described in Marmur J., Lane D. (1960) *Proc. Natl. Acad. Sci. USA,* 46:453-461 and Doty P. et al (1960) *Proc. Natl. Acad. Sci. USA,* 46:461-476. The stability of a nucleic acid duplex is measured by the melting temperature, or "$T_m$." The $T_m$ of a particular nucleic acid duplex under specified conditions is the temperature at which, on average, half of the base pairs have disassociated.

"Hybridization properties" of a polynucleotide refers to the ability of this polynucleotide or a fragment thereof to form a sequence-specific complex with another complementary polynucleotide or its fragment. "Hybridization properties" also generally refers herein to the complementary complex stability. In this aspect, "hybridization properties" is used in a similar fashion to "melting temperature" or "Tm."

"Improved" or "enhanced hybridization properties" of a polynucleotide, as used herein, refers to an increase in stability of a complex of this polynucleotide with its complementary sequence because of any factor, including but not limited to a change in reaction conditions such as pH, salt concentration and composition (e.g., an increase in magnesium ion concentration, presence of complex stabilizing agents such as intercalators or minor groove binders, etc.). The hybridization properties of a polynucleotide or oligonucleotide can be also altered by an increase or decrease in polynucleotide or oligonucleotide length. The cause or basis of the hybridization property enhancement is usually found in context herein.

"Melting temperature" or "Tm" refers to the temperature at which a complementary complex of nucleic acids, usually double-stranded, becomes half dissociated into single strands. These terms are also used in describing stabilities of polynucleotide secondary structures wherein two or more fragments of the same polynucleotide interact in a complementary fashion with each other forming complexes, e.g., hairpin-like structures, etc. A simple estimate of the Tm value may be calculated using the equation Tm=81.5+0.41(% G+C), when a nucleic acid is in aqueous solution at 1 M NaCl. More accurate calculations can be made using the base pair thermodynamics of a "nearest-neighbors" approach (Breslauer K. J. et al (1986) *Proc. Natl. Acad. Sci. USA,* 83:3746-3750; SantaLucia J. Jr. (1998) *Proc. Natl. Acad. Sci. USA,* 95:1460-1465).

The term "label" refers to any atom or molecule that can be used to provide a detectable signal and that can be attached to a nucleic acid or oligonucleotide. Labels include but are not limited to isotopes, radiolabels such as $^{32}P$; binding moieties such as biotin; haptens such as digoxygenin; luminogenic, mass tags; phosphorescent or fluorescent moieties, fluorescent dyes alone or in combination with other dyes or moieties that can suppress or shift emission spectra by FRET effect. Labels may provide signals detectable by fluorescence, radioactivity, colorimetry, gravimetry, X-ray diffraction or absorption, magnetism, enzymatic activity, mass spectrometry, binding affinity and the like. A label may be a charged moiety or alternatively, may be charge neutral. Labels can include or consist of nucleic acid or protein sequence, so long as the sequence comprising the label is detectable. The term "FRET-labeled" refers an oligonucleotide primer or probe which usually incorporated two dyes that are in a FRET interaction. A FRET-labeled oligonucleotide may incorporate one fluorescent dye but then, it is understood herein, that the fluorescence of this dye conjugated to an oligonucleotide is suppressed by any means other than a quenching dye, e.g. fluorescence of fluorescein is reduced in presence of neighboring guanosines.

"Fluorescent label" refers to a label that provides a fluorescent signal. Fluorescent labels are commonly fluorescent dyes, but may comprise any molecule including but not limited to a macromolecule like protein or a particle made from inorganic material like quantum dots as described in Robelek R. et al (2004) *Anal. Chem.,* 76: 6160-6165.

"FRET" is an abbreviation of Förster Resonance Energy Transfer effect. FRET is a distance-dependent interaction occurring between two dye molecules in which excitation is transferred from a donor to an acceptor fluorophore through dipole-dipole interaction without the emission of a photon. As a result, the donor molecule fluorescence is quenched, and the acceptor molecule becomes excited. The efficiency of FRET depends on spectral properties, relative orientation and distance between the donor and acceptor chromophores (Förster T. (1965) Delocalized excitation and excitation transfer. In Sinanoglu, O. (ed.), *Modern Quantum Chemistry, Istanbul Lectures, part III*. Academic Press, New York: 93-137). In the case of random dipole orientation, and with a good overlap between emission spectrum of the donor and absorption spectrum of the acceptor, the efficiency of FRET is dependent on the inverse sixth power of the intermolecular separation (Clegg R. M. (1992) *Methods Enzymol.,* 211:353-388; Clegg R. M. (1995) *Curr. Opin. Biotech.,* 6:103-110; Selvin P. R. (1995) *Methods Enzymol.,* 246:300-334). This makes FRET useful over distances comparable to the dimensions of biological macromolecules (Stryer L. and Haugland R. P. (1967) *Proc. Natl. Acad. Sci. USA,* 58:719-726) and this effect is widely used in biomedical research and particularly in probe designs for nucleic acid detection (Didenko V. V. (2001) *BioTechniques,* 31, 1106-1121).

As used herein, the term "FRET probe" refers to a fluorescent oligonucleotide which is used for detection of a nucleic acid of interest wherein detection is based on FRET effect. The FRET probe commonly contains two chromophores. The acceptor chromophore is usually a non-fluorescent dye chosen to quench fluorescence of the reporting fluorophore (Eftink M. R. (1991) In Lakowicz J. R. (ed.), *Topics in Fluorescence Spectroscopy.* Plenum Press, New York, V.2:53-126). Formation of sequence specific hybrids between target nucleic acid and probes leads to a change in fluorescent properties of the probe providing detection of the nucleic acid target. Many detection designs exploring the FRET effect have been reported to date. The most common FRET probes are: TaqMan™ (Lie Y. S. and Petropoulos C. J. (1998) *Curr. Opin. Biotech.,* 9:43-48; Livak K. J. et al (1995) *PCR Methods and Applications,* 4:357-362); Beacon (Tyagi S, and Kramer F. R. (1996) *Nat. Biotechnol.,* 14:303-308; Bonnet G. et al (1999) *Proc. Natl. Acad. Sci. USA,* 96:6171-6176; Tyagi S. et al (2000) *Nat. Biotechnol.,* 18:1191-1196; Marras S. A. E. et al (2002) *Nucleic Acids Res.,* 30:e122; Piatek A. S. et al (1998) *Nat. Biotechnol.,* 16 359-363; Lewin S. R. et al (1999) *J. Virol.,* 73:6099-6103); Eclipse (Afonina I. A. et al (2002) *BioTechniques,* 32:940-949); Scorpion primers (Whitcombe D. et al (1999) *Nature Biotech.,* 17:804-807; Thelwell N. et al (2000) *Nucleic Acids Res.,* 28:3752-3761); self-quenching (Livak K. J. et al, U.S. Pat. No. 5,723,591) probes, and the cited manuscripts and patents are incorporated herein by reference. The FRET probe may comprise a single oligonucleotide molecule or more than one oligonucleotide; for example, Adjacent Hybridization probes (Heller M. J. and Morrison L. E. (1985) In Kingsbury, D. T. and Falkow, S. (eds.), *Rapid Detection and Identification of Infectious Agents.* Academic Press, New York, 245-256; Cardullo R. A. et al (1988) *Proc. Natl. Acad. Sci. USA,* 85:8790-8794; Gundry C. N. et al (1999) *Genet. Test.,* 3:365-370). A detailed review on various designs and applications of FRET oligonucleotide probes can be found in Didenko V. V. (2001) *BioTechniques,* 31:1106-1121. The FRET probes of the invention for 5'-nuclease assay are designed to provide an optimal cleavage structure shown in FIG. 7 using the basic rules established for TaqMan™ cleavable probe assays described in Lie Y. S. and Petropoulos C. J. (1998) *Curr. Opin. Biotech.,* 9: 43-48; Livak K. J. et al (1995) *PCR Methods and Applications,* 4: 357-362). However, unlike the TaqMan™ probes which commonly require to have elevated stability (Tm by ~5° C. higher than PCR annealing temperature), the FRET probes used herein may have Tm equal or ~5° C. lower than PCR annealing temperature. Guidance for the design of FRET probes used in 3'-nuclease assay of the invention can be found in Kutyavin I. V. et al (2004) US Patent Application #20040101893; Kutyavin I. V. et al (2006) *Nucleic Acids Res.,* 34: e128.

A "reaction mixture" generally refers to a solution containing all the necessary reactants for performing an amplification or detection reaction or both, which in addition to main components such as target nucleic acids, DNA polymerases, oligonucleotide primers, probes or other oligonucleotide components, may include (but not limited to the inclusion of) detecting agents, specialty enzymes, nucleoside 5'-triphosphates including the modified ones, buffering agents to maintain pH at a selected level during a reaction, salts, co-factors and additives, for example, 1-methyl-2-pyrrolidinone, glycerol, poly(ethylene glycol), dimethyl sulfoxide or formamide and the like.

The term "reaction vessel" refers to any kind of a container used to perform the amplification and/or detection reactions of the methods of the invention and wherein the term "reaction vessel" means any appropriate way of isolation of the reaction mixture from the environment. A "reaction vessel" may be made from any solid material, including but not limited to, plastic, glass, quartz, metal, etc. The reaction vessels may be of any sizes wherein the reaction volume may be measured in nanoliter, microliter, milliliter or liter scales. The reaction vessels can be of any shape, e.g. tubes, wherein multiple reaction vessels are combined in one plate. The reaction vessels may be made from a liquid material wherein, for example, aqueous drops of the reaction mixtures of the invention are suspended and floating in oil. The term "reaction vessel" also includes a micro-fluidic or fluidic card made from any material, usually plastic, and wherein the card comprises reaction chambers and channels allowing mixing the reaction components in an order or simultaneously as required by the methods of the invention.

As used herein, the term "kit" refers to any system for delivering materials. In the context of reaction assays, such delivery systems include elements allowing the storage, transport, or delivery of reaction components such as oligonucleotides, buffering components, additives, reaction enhancers, enzymes and the like in the appropriate containers from one location to another commonly provided with written instructions for performing the assay. Kits may include one or more enclosures or boxes containing the relevant reaction reagents and supporting materials. The kit may comprise two or more separate containers wherein each of those containers includes a portion of the total kit components. The containers may be delivered to the intended recipient together or separately.

The term "solid support" refers to any material that provides a solid structure with which another material can be attached. Such materials may include but not limited to silicon, plastic, metal, glass, ceramic surfaces, and the like. Solid support may be of a rigid or non-rigid nature like gels, rubbers, polymers, etc. and it may be any type of shape including spherical shapes like beads. Certain embodiments of the present invention have at least one of the reaction components such as, e.g. oligonucleotide primer, oligonucleotide probe, cleavage enhancer or modified amplicon immobilized on solid support at amplifying or detecting stages or both. Examples of immobilization are shown in FIG. 19. A biological material is "immobilized" to a solid support when it is associated with the solid support through a non-random chemical or physical interaction. The immobilization or attachment may be through a covalent bond using specialty spacer molecule or linker group. However, the immobilization need not be covalent or permanent.

As used herein, "detection assay" or "assay" refers a reaction or chain of reactions that are performed to detect nucleic acids of interest. The assay may comprise of multiple stages including amplification and detection reactions performed consequently or in real time, nucleic acid isolation and intermediate purification stages, immobilization, labeling, etc. The terms "detection assay" or "assay" encompass variety of derivative forms of the methods of the invention, including but not limited to, a "5'-" or "3'-nuclease assay" when an assay is based on use of 5'- or 3'-nuclease respectively, a "post-PCR assay" when the detection is performed after the amplification stage, a "real time assay" when the amplification and detection are performed simultaneously, a "FRET assay" when the detection is based using FRET effect, "immobilized assay" when one of either amplification or detection oligonucleotide components or an amplification product is immobilized on solid support, and the like.

The term "assay design" has broad meaning related to any, sometimes not necessarily to a particular, method of the invention including all reaction conditions (e.g. temperature, salt, pH, enzymes, oligonucleotide component concentrations, etc.), structural parameters (e.g. length and position of primers, design of specialty sequences, apply or do not apply a cleavage enhancer, etc.) and assay derivative forms (e.g. post-PCR, real time, immobilized, 5' or 3'-nuclease, FRET or flap detection schemes, etc.) chosen to amplify and to detect the nucleic acids of interest.

DETAILED DESCRIPTION OF EXEMPLARY ASPECTS

Nucleic acids of interest are commonly present in test samples at a low concentration which does not allow the direct detection. Amplification of the target nucleic acids is needed and PCR remains to be the most common choice of the amplification technique, although other technologies, e.g. isothermal amplification schemes, are emerging. PCR may amplify nucleic acids to a nanomolar range of concentrations starting from as little as a single molecule of the nucleic acid of interest. Nanomolar concentrations are well within the detection range of fluorescence-based technologies providing a convenient way of the amplification products detection, especially in real time.

The most advanced detection techniques used in PCR employ Förster Resonance Energy Transfer effects (FRET). This is because the energy transfer is very effective within the distances comparable to the dimensions of biological macromolecules. The FRET based technology wherein the FRET interaction is disrupted permanently due to the cleavage of a respective FRET-labeled oligonucleotide component have an advantage over the hybridization triggered approaches. The cleavage-based technologies like TaqMan™ assay may generates two-three times more fluorescent signal per target molecule than the Molecular Beacon™, Scorpion™, Eclipse™ and other hybridization triggered assay designs. This is mainly because of the signal accumulation effect. Since the probe cleavage is irreversible in TaqMan™, the signal generated at a given PCR cycle is a sum of signals generated at that particular cycle plus all previous ones whereas the signal in the hybridization triggered technologies is always in a linear ratio to the target concentration at a given cycle. Amplification products play somewhat "passive" role in many reported (e.g., as "BACKGROUND" herein above) conventional PCR assays including those wherein the detection is based on oligonucleotide cleavage. In these assays, the amplicons provide one (target) strand while the rest of the cleavage structure is assembled employing oligonucleotide components.

Unlike in the conventional assays, PCR amplification products of the present invention "actively participate" in the detection providing at least two and, in certain embodiments, all three strands of the cleavage complex, used herein under a term "three-strand cleavage structure." The invention can be practiced in a variety of derivative forms to expand and to improve the nucleic acid detection capabilities in detection of polymorphic variation, gene expression analysis, forensics, pathogen detection, environmental testing, clinical diagnostics, etc. The inventive aspects benefit nucleic acid detection in many ways, for example, by reducing the manufacturing cost of the detection components, simplifying and accelerating the detection, saving time on the assay development, reducing the assay failure rate (first designs), increasing the assay sensitivity and specificity of action, improving the assay multiplexing capabilities, etc.

In one embodiment, the invention provides a method for the detection of a target nucleic acid in a sample, comprising: (i) amplifying said target nucleic acid using PCR in presence of a pair of oligonucleotide primers wherein at least one oligonucleotide primer is designed to incorporate a 5'-specialty sequence to provide an amplification product which folds into a secondary structure, (ii) detecting said amplification product which folds into a secondary structure, comprising: a) providing an oligonucleotide cleavage component, b) hybridizing said oligonucleotide cleavage component with said amplification product to form a three-strand cleavage structure wherein two strands of said three-strand cleavage structure are provided by said secondary structure of said amplification product, b) cleaving 3'- or 5'-strands of said three-strand cleavage structure in media containing duplex-specific nuclease activity resulting in a cleavage product, c) detecting said cleavage product, wherein presence of said cleavage product in the reaction mixture is indicative of the presence of said target nucleic acid in said sample.

In yet another embodiment, the invention provides a method for the detection of a target nucleic acid in a sample, comprising: (i) amplifying said target nucleic acid using PCR in presence of a pair of oligonucleotide primers wherein both oligonucleotide primers are designed to incorporate 5'-specialty sequences to provide an amplification products which folds into a three-strand cleavage structure, (ii) detecting at least one of said amplification products, comprising: a) cleaving 3'- or 5'-strands of said three-strand cleavage structure in media containing duplex-specific nuclease activity resulting in a cleavage product, b) detecting said cleavage product, wherein presence of said cleavage product in reaction mixture is indicative to presence of said target nucleic acid in said sample.

I. Three-Strand Cleavage Structures Formed by Amplicons Folding into Secondary Structures.

Virtually any randomly taken polynucleotide, including the 96-mer target oligodeoxyribonucleotide (SEQ ID NO:1) that was used as a target nucleic acid in the working Examples of the invention, may form elements of secondary structure, e.g. bulge loops, internal loops, hairpins, Y-structures, heterologous loops, and the like due to an "accidental" complementarity of one sequence within the polynucleotide to yet another sequence of the same polynucleotide. It has been shown that the progression of several types of DNA polymerases, from prokaryotes, phages and eukaryotes, is impended at certain DNA sequences which were predicted to fold into secondary structures, e.g. LaDuca R. J. et al (1983) *Biochemistry*, 22: 5177-5188; Bedinger P. et al (1989) *J. Biol. Chem.*, 264: 16880-16886; Bierne H. and Michel B. (1994) *Mol. Microbiol.*, 13: 17-23. Stabilization of the secondary structures in nucleic acids was blamed for negative results of certain duplex-stabilizing base modifications observed in RNA detection (Nguyen A. et al (2002) *BMC Biotechnology*, 2: 14; Hacia J. G. et al (1998) *Nucleic Acids Res.*, 26: 4975-4982). Lyamichev et al showed that these secondary structure elements may be cleaved and detected in presence of a 5'-nuclease activity and this may find a practical use in nucleic acids polymorphism identification (Dahlberg J. E. et al (1998) U.S. Pat. No. 5,719,028; Kaiser M. W. et al (1998) U.S. Pat. No. 5,843,669; Dahlberg J. E. et al (1999) U.S. Pat. No. 5,888,780). If the secondary structure duplex is relatively long and stable, this may render certain target nucleic acids as none-amplifiable in PCR, e.g. as exemplified in Dahlberg J. E. et al (1995) U.S. Pat. No. 5,422,253, especially when 5'-nuclease activity is present during the amplification. It has been well established in the art that amplification of nucleic acids of interest which may fold into "apparent" secondary structures should be avoided due to the anticipated negative effect of those structures on PCR. Modern software used to design oligonucleotide components for PCR, e.g. Visual OMP (DNA software), Beacon designer 7.00 (Premier Biosoft International) and the like, are set to screen the potential designs for the secondary structure elements, including the amplicons, assigning a secondary structure penalty score and thus eliminating several designs from the consideration.

Despite the well justified and documented concern about the negative role of polynucleotide secondary structures in PCR, the present inventive aspects are based on amplification and detection of nucleic acids that fold into the secondary structures. Although these structures may be natural, i.e. originally present in the target nucleic acids, in preferred embodiments of the invention these secondary structures are intentionally created by using oligonucleotide primers which carry 5'-specialty sequences. In particular, at a certain degree of stability, the amplicon secondary structures may have very little, if any, negative effect on the PCR amplification while considerably enhancing and simplifying the nucleic acid detection process. The amplicons of the invention fold into secondary structures and, in certain aspects, with help of oligonucleotide cleavage components, in yet other aspects, without the oligonucleotide cleavage components, form three-strand cleavage structures. These cleavage structures are cleaved in the methods of the invention resulting in cleavage products. The cleavage products are detected and this is indicative of presence of the target nucleic acids in samples. Examples of the three-strand cleavage structures that may be formed in methods of the invention are shown in FIG. 1. The three-strand cleavage structures are duplex structures when two oligonucleotide sequences anneal to neighboring regions of the same linear complementary nucleic acid sequence.

FIG. 1 shows examples of the 'three-strand' cleavage structures that are formed in methods of the invention. A 'three-strand cleavage structure' refers to a duplex structure wherein two oligonucleotide sequences anneal to neighboring regions of the same linear complementary nucleic acid sequence. The strands are defined by specific names as shown in the structure B: target strand, 3'-strand, and 5'-strand. The symbol "—OH" represents 3'-hydroxyl group of a 3'-terminal nucleoside of the 3'-strand. Two duplexes in the "three-strand cleavage structures" can be separated by ten and preferably less then five nucleotides of a "target strand" as shown in structures A and F. The three-strand cleavage structures may incorporate either "3'-flap" (structures C, D and E) or "5'-flap" (structures C, E and F) sequences. The flap sequences may or may not be complementary to the target strand. The three-strand cleavage structures of the invention exemplified here are formed wherein at least two of the strands, e.g. the target strand and 5'-strand or the target strand and 3'-strand, are provided by a PCR amplification product. In certain embodiments, all three strands of a cleavage structure are provided by a PCR amplicon. Either 3'- or 5'-strands may be cleaved in methods of the invention.

Double stranded nucleic acids are substrates for duplex-specific nucleases. For example, RNase H enzymes cleaves RNA strand in RNA/DNA heteroduplexes (Fong W. et al (2000) *J. Clin. Microbiol.*, 38: 2525-2529; Modruzan Z. et al (2000) *Diagn. Microbiol. Infect. Dis.*, 37: 45-50; Harvey J. J. et al (2004) *Anal. Biochem.*, 333: 246-255). 5'-Nuclease activity that may be found in many DNA polymerases degrades DNA duplexes by the 5'-ends of the strands. A DNA duplex represent a suboptimal substrate for the duplex-specific 5'-nucleases and the cleavage is inefficient. However, for this reason, the DNA polymerases selected for the DNA sequencings are commonly deficient in 5'-nuclease activity. Although duplex-specific nucleases can cleave a nucleic acids duplex with certain degree of efficiency but, in many occasions, the cleavage rate significantly increases when yet another duplex structure appears in proximity forming a three-strand cleavage structure. The present invention particularly exploits this property of the duplex-specific nucleases. Two duplexes in the three-strand cleavage structures can be separated by ten and preferably less then five nucleotides of a "target strand." The three-strand cleavage structures of the invention commonly incorporate flap sequences at the strand ends which in certain aspects may be, at least partially, complementary to the target strand.

The choice of a particular three-strand cleavage structure to perform the methods of the invention depends on number of factors but mainly on the substrate properties of the duplex-specific nuclease employed. For example, the structures shown in FIG. 1 are, in particular, useful in practicing 5'-nuclease assays wherein the 5'-strands of the structures A-F are cleaved. The structures D and E represent examples of an optimal cleavage structure for these assays. An optimal cleavage structure for 5'-nuclease methods is also shown in FIG. 2.

FIG. 2 shows a schematic diagram of an optimal three-strand cleavage structure for practicing 5'-nuclease assays of the invention. Two duplexes are formed without a target strand gap. The 3'-strand contains a single nucleoside flap which is an important element for the 5'-endonuclease recognition and binding. The presence of an "unblocked" 3'-hydroxyl group is important. The arrow points to a phosphodiester bond between the first and second hybridized nucleosides of the 5'-strand, preferably hydrolyzed by the enzyme. The presence of the 5'-flap is optional but a cleaved flap may be detected in certain methods of the invention (e.g., FIG. 10). Any structural duplex abnormalities within ~4-6 base pairs on either side of the duplex junction (shown by a grey box) may negatively affect the nuclease binding/cleavage and this property can be used in detecting (discriminating) polymorphic variations in nucleic acids of interest.

According to the research of Lyamichev V. and coworkers (collectively from all manuscripts and patents cited herein with this name in authorship), the three-strand structures A, B, C and F are not optimal substrates for 5'-nuclease. However, these structures are within the scope of particular inventive aspects as long as, at least, two strands of the three-strand cleavage structures are provided by PCR amplification products. It was found by Lyamichev V. et al (1993, *Science*, 260: 778-783) that certain suboptimal structures, e.g. structures A, B, C and F, may rearrange into structures of relatively efficient cleavage which are "simulating" the optimal structures (like D and E) although with certain structural abnormalities. Moreover, in one of the examples provided herein (FIG. 16) comparable efficiencies of the 5'-nuclease cleavage were observed in both, an optimal and suboptimal cleavage structures.

In certain embodiments of the invention, the three-strand cleavage structures are cleaved in presence of 3'-duplex specific nucleases. Endonuclease IV from *E. coli* is an example of such 3'-nucleases. An optimal three-strand cleavage structure for this enzyme is shown in FIG. 4.

FIG. 4 shows a schematic diagram of an Endo IV optimal cleavage (see also Kutyavin I. V. et al (2004) US Patent Application #20040101893; Kutyavin I. V. et al (2006) *Nucleic Acids Res.*, 34: e128 and references cited therein). Endonuclease IV cannot cleave an internucleotide phosphodiester bond unless a nucleoside which is 3'- to this bond is damaged, e.g. a nucleoside base is missing (abasic site). The enzyme is duplex-specific but the presence of another duplex nearby the cleaved strand significantly accelerates the tail cleavage. An optimal substrate shown here simulates a partially "degraded" abasic site of two duplexes separated with one base target gap. Decrease (no gap) or increase in the gap length was shown to reduce the Endo IV activity. The endonuclease recognizes the substrate and cleaves a 3'-tail (—PO-2-R) between the 3'-deoxyribose oxygen and phosphor atoms initiating the DNA repair process. The enzyme is particularly sensitive to structural abnormalities like single base mismatches (SNPs), insertions or deletions within ~4-6 base pairs duplex (solid grey box) counting from the terminal nucleotide of the 3'-strand. Mismatches within the 5'-strand duplex (broken grey box) may also affect the substrate properties but with a lesser degree.

The Endonuclease IV initiates repair of naturally occurring abasic sites cleaving the "damaged" strand in double stranded DNA hydrolyzing phosphodiester bond which is 5' to the lesion. This 3'-nuclease also can remove $3'-PO^-_2$—R tails in the three-strand cleavage structures shown in FIG. 3.

FIG. 3 shows examples of three-strand cleavage structures that may be used in 3'-nuclease assays of the invention. The three-strand cleavage structures are formed herein between a PCR amplicon and oligonucleotide probe carrying a —PO-2-R tail wherein R is a detectable label. In these cases, the amplicon folds into a secondary structure and provides a target strand and 5'-strand while an oligonucleotide probe provides a 3'-strand. The strand assignment is shown in structure B. Endonuclease IV (Endo IV) may be used in the inventive assays to provide a strand-specific cleavage of a 3'-tail in the shown structures. The arrows point to a hydrolyzed phosphodiester bond between a 3'-oxygen and phosphorous atoms of the tail. All examples of the three-strand cleavage structures shown in this Figure may be used in the 3'-nuclease assays of the invention with differing degrees of preference. An Endo IV optimal cleavage structure is shown in FIG. 4. Presence of a very short 5'-flap, e.g. structure D, is anticipated to have little, if any negative effect on the Endo IV activity but in certain derivative forms of the 3'-endonuclease assay presence of such short 5'-flaps may be important.

Although the enzyme expresses the tail-clipping activity on simple duplex structures but presence of another duplex nearby the cleaved strand significantly accelerates the tail cleavage (Kutyavin I. V. et al (2004) US Patent Application #20040101893; Kutyavin I. V. et al (2006) *Nucleic Acids Res.*, 34: e128). An optimal substrate shown in FIG. 4 simulates a partially "degraded" abasic site of two duplexes separated with one base target gap. Decreasing (no gap) or increasing the gap length was shown to reduce the Endo IV activity. However, the cleavage rate within the suboptimal cleavage structures, e.g. structures A, C, D and F (FIG. 3) may be still elevated when compared with that observed on a simple duplex substrate (structures A through F in FIG. 3 with 5'-strand is absent).

II. Amplification of Nucleic Acids by Polymerase Chain Reaction (PCR)

Amplicons carrying elements of secondary structure may be obtained using amplification technologies other than PCR, for example, Loop-Mediated Amplification (LMA) (Notomi T. and Hase T., U.S. Pat. No. 6,410,278; Notomi T. et al (2000) *Nucleic Acids Res.*, 28, e63) and Helicase-Dependent Amplification (HAD) (Vincent M. et al (2004) *EMBO reports*, 5: 795-800; An L. et al (2005) *JBC*, 280: 28952-28958). Nevertheless PCR which was originally discovered and described by Mullis K. B. et al, U.S. Pat. No. 4,683,195 and Mullis K. B., U.S. Pat. No. 4,683,202 is the preferred choice for the inventive aspects because of many reasons, but primarily because of the possibility to conduct the detection assays in real time. The PCR amplification is commonly performed using two oligonucleotide primers. The oligonucleotide primers are designed to hybridize to the opposite nucleic acid strands such as extension of one primer provides a template for another primer in the next PCR cycle. Generally, a PCR consists of repetition (or cycles) of (i) a denaturation step which separates the strands of a double stranded nucleic acid, followed by (ii) an annealing step, which allows primers to anneal to positions flanking a sequence of interest; and then (iii) an extension step which extends the primers in a 5' to 3' direction thereby forming a nucleic acid fragment complementary to the target sequence. Each of the above steps may be conducted at a different temperature using an automated thermocycler. The PCR cycles can be repeated as often as desired resulting in an exponential accumulation of a target DNA fragment whose termini are usually defined by the 5' ends of the primers used. Certain exceptions to this rule may apply when partially extendable primers of the invention are used. Particular temperatures, incubation time at each step and rates of change between steps depend on many factors well-known to those of ordinary skill in the art and examples can be found in numerous published protocols, for example, McPherson M. J. et al. (1991 and 1995) and the like. Although conditions of PCR can vary in a broad range, a double-stranded target nucleic acid may be denatured at temperature >90° C., primers annealed at a temperature in the range 50-75° C., and the extension is preferably performed in the range 72-78° C.

The cycle time of the PCR is usually less than 5 minutes and even more commonly less than 2 minutes. In preferred embodiments of the invention, oligonucleotide components of the assays are designed to perform at elevated annealing temperatures >65° C. or even >70° C. The increase of the annealing temperatures to the temperature range (72-75° C.) which is optimal for thermostable DNA polymerases improves productivity and specificity of PCR and it allows "merging" the annealing and extension stages. Thus, in preferred embodiments, PCR is performed in two stages, (i) strand denaturation and (ii) annealing/extension stage (combined). The number of the PCR cycles that is necessary to provide a detectable target nucleic acid concentration depends on the initial target nucleic acid load (amount) which is commonly unknown. PCR of the invention may be performed in many derivative forms well known in the art, including but not limited to, RT-PCR, real time PCR, nested PCR, quantitative PCR, multiplexed PCR, hot start PCR, asymmetric PCR and the like. Detailed guidance for conducting these PCR variations may be found numerous published protocols, e.g. McPherson M. J. et al. (1991 and 1995); Clementi M. et al (1993) *PCR Methods Appl.*, 2:191-196; Clegg R. M. (1992) *Methods Enzymol.*, 211: 353-388; Livak K. J. et al (1995) *PCR Methods and Applications*, 4: 357-362; Freeman W. M. et al (1999) *Biotechniques*, 26: 112-122, 124-125; Lie Y. S. and Petropoulos C. J. (1998) *Curr. Opin. Biotech.*, 9: 43-48; Mackay I. M. et al (2002) *Nucleic Acids Res.*, 30: 1292-1305; Mackay J., Landt O. (2007) *Methods Mol. Biol.*, 353: 237-262; Niesters H. G. (2001) *Methods*, 25: 419-429 and the like.

Hot start PCR eliminates exposure of DNA polymerase to the reaction components at low temperature avoiding nonetarget specific priming. This can be achieved manually, by adding the enzyme to a preheated reaction mixture. An antibody blocked Taq polymerase (JumpStart Taq polymerase, Sigma) was used in the Examples herein. This polymerase is inactive at low temperatures and it is quickly activated after the first denaturation cycle. This is a preferred method of the hot start PCR in the methods of the invention. The methods of the invention may also benefit performing asymmetric PCR. It may be desired to increase concentration of one of two complementary amplicon strands, especially the detected strand. For example, in the method of FIG. 11, the forward specialty oligonucleotide primer may be taken in excess amount over the respective reverse primer. This would lead to a preferential amplification of the PCR amplicon antisense strand which is folded into a secondary structure and detected in reaction with Endonuclease IV cleavable FRET-probe. In the method of FIG. 8, the excess of the reverse specialty primer would also increase the yield of the three-strand cleavage structure E. Those of ordinary skill in the art will appreciate that more than one target nucleic acid may be amplified and detected in the same reaction mixture using the methods of the invention providing multiplexed PCR. In this case, the oligonucleotide components such as oligonucleotide primers, including specialty primers, oligonucleotide cleavage components, if they are necessary due to the method choice, would be designed for every nucleic acid of interest amplified and detected. Methods of the invention may be used in combination with other conventional technologies in multiplexed PCR wherein at least one target nucleic acid of a mixture is amplified and detected by a method of the invention.

In preferred embodiments of the present invention, detection of the target nucleic acids can be performed in real time. Real time detection is possible when all detection components are available during the amplification and the reaction conditions (e.g., temperature, buffering agents to maintain pH at a selected level, salts, co-factors, scavengers, etc.) support both stages of the reaction, amplification and the detection. In real time assays, a target nucleic acid is detected as the amplification reaction progresses.

Many modern real time PCR techniques are based on fluorescent detection employing, in particular, FRET effect. Reviews of the detection chemistries in real time PCR can be found in, e.g. Didenko V. V. (2001) *BioTechniques*, 31, 1106-1121; Mackay I. M. et al (2002) *Nucleic Acids Res.*, 30: 1292-1305, and Mackay J., Landt O. (2007) *Methods Mol. Biol.*, 353: 237-262, which are also incorporated herein by reference. In preferred embodiments of the present invention, detection of nucleic acids is also based on use of FRET effect and FRET probes. The detection is provided by a strand-specific cleavage of three-strand cleavage structures which are formed by amplification products which folds into a secondary structure and, in certain embodiments, hybridized to oligonucleotide cleavage components. Placing the FRET dyes on opposite sides of the cleavage point permanently disrupt the FRET providing a detectable fluorescent signal. The Examples provided herein demonstrate the methods of the invention, which were performed in real time and which explored numerous FRET system designs (FIGS. 14-18).

The real time methods of the invention are, in particular, useful for quantitative PCR designed to measure the abundance of one or more specific target sequences in a sample. Quantitative measurements are usually made using one or more reference nucleic acid sequences which may be assayed separately or together with a target nucleic acid. Techniques for quantitative PCR are well-known to those of ordinary skill in the Art and a detailed guidance may be found in, e.g. Gu Z. et al (2003) *J. Clin. Microbiol.*, 41: 4636-4641; Becker-Andre M. and Hahlbrock K. (1989) *Nucleic Acids Res.*, 17: 9437-9446; Freeman W. M. et al (1999) *Biotechniques*, 26:112-122, 124-125; Lutfalla G. and Uze G. (2006) *Methods Enzymol.*, 410: 386-400; Clementi M. et al (1993) *PCR Methods Appl.*, 2:191-196; Diviacco S. et al (1992) *Gene*, 122: 313-320.

In certain aspects of the invention, the amplification and detection stages may be performed separately, not in real time, when the detection stage follows the PCR amplification in post-PCR assay format. For example, Endonuclease IV from *E. coli* does not survive at elevated temperatures of PCR and it can be added to the reaction mixture after the amplification has been completed, to initiate the detection (FIG. 11).

The post-PCR detection may be performed in a variety of derivative forms. In one aspect, all detection components may be present in the reaction mixture during PCR but they do not perform. For example, the detection components of the invention assays shown in FIGS. 6, 7, 8 and 11 (e.g. cleavage enhancers and oligonucleotide probes) may be designed to perform at a relatively low temperature, e.g. 50° C. while PCR is conducted at elevated temperatures, e.g. >70° C.

The oligonucleotide template sequences are respectively designed to insure robust amplification at these stringent conditions but the specialty sequences are preferably designed to provide stable secondary structures in amplicons at the detection stage (50° C.) while these structure do not essentially form during PCR. The detection reaction may be initiated in this exemplified assay by lowering the temperature to 50° C. after PCR is complete. In yet another aspect, one or all detection components may be added to a PCR reaction vessel to begin the detection of the amplified target nucleic acids. In a preferred embodiment of the invention, the reactions of the invention (PCR and detection) are performed in a microfluidic or fluidic card usually made from a plastic material and wherein the card comprises reaction chambers and channels allowing mixing the reaction components in an order or simultaneously.

Post-PCR methods of the invention are particularly useful in qualitative detection assays commonly performed to detect polymorphic variations in nucleic acids of interest as small as a single nucleotide polymorphism or SNP. Example of such an assay may be found, for example, in Kutyavin I. V. et al (2006) *Nucleic Acids Res.*, 34: e128. Those of ordinary skill in the art will appreciate that all methods of the invention can be used for detection of polymorphic variations. One of the preferred methods of the invention for this purpose is shown in FIG. 7.

FIG. 7 shows another method embodiment of the invention that is based on the use of a 5'-nuclease activity. A forward oligonucleotide primer contains a 5'-specialty sequence (shown in gray color) wherein the primer template and specialty sequences represent an uninterrupted chain of nucleotides. Extension of this specialty primer in stage A results in synthesis of an antisense strand providing a double stranded amplicon (stage B). After the strand separation (e.g., 95° C.), a reverse primer hybridizes to the antisense strand and DNA polymerase extends the complex (stage C) resulting in yet another double stranded amplicon (stage D). Since the specialty primer is fully extendable (does not incorporate a none-extendable linker), a full complement to the forward primer specialty sequence appears at the 3'-end of a sense amplicon strand. After another round of strand separation, the sense amplicon (synthesized in stage D) folds into a secondary structure carrying a single nucleoside 3'-flap (stage E). A FRET probe is designed to bind to this amplicon next to the secondary structure duplex forming an optimal three-strand cleavage structure as shown in the stage E. A 5'-nuclease recognizes the structure and cleaves the probe strand disrupting the FRET and proving a detectable fluorescent signal in stage F. In this method, unlike in other methods of the invention, the detected amplicon is not the one which incorporates the specialty primer sequence but rather its replica, which also folds into a secondary structure. The method shown in this figure may be performed in a cycling mode when more than one probe is cleaved per target amplicon molecule. This may be achieved, for example, by providing a molar excess of the oligonucleotide probe over amounts of the respective oligonucleotide primers used in amplifying a nucleic acid of interest.

In many cases when the target polymorphic variations are short sequences, the oligonucleotide primers including specialty primers may be designed the same for all detected targets. The sequence discrimination (individual sequence detection) is achieved by using different oligonucleotide probes each of which is individually labeled and fully complementary to every detected nucleic acid. The probes are designed to bind to the target nucleic acids such as the sequences of polymorphic variations are located within their binding sites. In case of the 5'-nuclease assay of FIG. 7, the best discrimination may be achieved when the polymorphic sequence, e.g. SNP, is positioned at the 5'-end of the probe strand. As discussed in the context of FIG. 2, 5'-nucleases are very sensitive to the duplex structural abnormalities nearby to the cleavage point. The cleavage takes place if probes are forming fully complementary complexes, but mismatched complexes usually show very little, if any detectable cleavage. Although thermostable 5'-nucleases usually slow down at temperatures of ~45-55° C., these reaction conditions may allow using short probes which are exceptionally discriminatory in distinguishing the polymorphic variation. Alternatively, methophilic 5'-nucleases may be applied when the assay is performed in post-PCR format.

In certain embodiments of the invention, at least one of the reaction components such as an oligonucleotide primer, oligonucleotide probe, cleavage enhancer or modified amplicon, is/are immobilized on solid support during the amplifying or detecting stages, or during both stages. The immobilization or attachment may be through a covalent bond using specialty spacer molecule or linker group as described, e.g. in Mitterer G., Schmidt W. M. (2006) *Methods Mol. Biol.*, 345: 37-51; Fedurco M. et al (2006) *Nucleic Acids Res.*, 34: e22; Kojima T. et al (2005) *Nucleic Acids Res.*, 33: e150; Mercier J. F., Slater G. W. (2005) *Biophys. J.*, 89: 32-42; Mercier J. F. et al (2003) *Biophys. J.*, 85: 2075-2086. Examples of the immobilization schemes that may be used in the methods of the invention are shown in FIG. 19.

FIG. 19 diagrammatically shows certain examples of immobilization of oligonucleotide components or amplicons of the invention during PCR or detection reactions. Panel A is wherein a cleavage enhancer in 5'-nuclease assay is coupled to a solid support. Panel B illustrates the method shown in FIG. 7 wherein a reverse (conventional) oligonucleotide primer is coupled by its 5'-end to a solid support. Panel C shows an immobilized probe in a 3'-nuclease method of the invention which is discussed in FIG. 11. Panel D demonstrates immobilization of a specialty oligonucleotide primer in the method of FIG. 5.

However, the immobilization need not be covalent or permanent. In preferred embodiments, the oligonucleotide component immobilization is achieved using biotin-avidin complex. Immobilization of cyanuric chloride activated oligonucleotides on amino modified surfaces is yet another example as described in Van Ness J. et al (1991) *Nucleic Acids Res.*, 19: 3345-3350.

A typical PCR reaction of the invention when the detection components are not present in the reaction mixture comprises a target nucleic acid, a pair of oligonucleotide primers, a suitable DNA polymerase, and a mixture of four deoxynucleoside 5'-triphosphates (dATP, dTTP, dCTP and dGTP). At least one of the oligonucleotide primers is a specialty primer of the invention. Magnesium ion is preferably present in the reaction mixture because it enables catalytic activity of DNA polymerases. The reaction components are mixed using appropriate stock solution to provide, for example, the following concentrations in a 25 µl reaction mixtures: PCR primers—200 nM each; JumpStart DNA polymerase (Sigma)—0.04 U/µl; deoxynucleoside 5'-triphosphates (dNTPs)—200 µM each in 50 mM KCl, 2 mM $MgCl_2$, 20 mM Tris-HCl (pH 8.0). In addition to the components listed above a PCR reaction mixture of the invention may include, but not be limited to, oligonucleotide cleavage components such as cleavage enhancers or probes (e.g. at 200 nM concentration), duplex-specific nucleases or specialty enzymes other than DNA polymerase, salts other than KCL and $MgCl_2$, co-factors and additives, for example, 1-methyl-2-pyrrolidinone, glycerol, poly(ethylene glycol), dimethyl sulfoxide or formamide and the like.

III. Detection of Amplified Nucleic Acids

Amplification products of the invention fold into secondary structures which, in certain embodiments with oligonucleotide cleavage components, form three-strand cleavage structures recognized and cleaved by duplex-specific nucleases. The cleavage products are detected in the methods of the invention and their presence in reaction mixtures is indicative of presence of nucleic acids of interest in samples. Particular methods of the invention may be divided into two mutually different approaches. In certain embodiments, the three-strand cleavage structures are representing optimal substrates for 5'-nucleases. In other embodiments of the invention, the cleaving enzymes are 3'-nucleases.

The cleavage products in the reactions of the invention can be detected by any physical, chemical or biological means including but not limited to electrical force (e.g. electrophoresis), gravity (e.g. sedimentation), spectroscopy (e.g. radio spectroscopy, UV, mass spectroscopy, fluorescence, chemiluminescence, chemifluorescence, etc.), absorption, magnetism, chromatography (HPLC, reverse-phase, ion-exchange, volume exclusion, etc.), reactions with proteins (restrictases, endonucleases, polymerases, kinases and other enzymatic activities), binding affinity and the like. In preferred embodiments, the cleavage products are labeled and the label is used in their detecting. The useful labels include but are not limited to isotopes, radiolabels such as $^{32}P$, binding moieties such as biotin, luminogenic and mass tags, phosphorescent or fluorescent moieties, fluorescent dyes alone or in combination with other dyes or moieties that can suppress or shift emission spectra by FRET effect. A label may be a charged moiety or alternatively, may be charge neutral. Labels can include or consist of nucleic acid or protein sequence, so long as the sequence comprising the label is detectable. In certain embodiments, the cleavage product can be a flap sequence which, for example, may be detected in a consequent cleavage reaction with a FRET-labeled probe as this is shown in FIG. 10.

FIG. 10 shows diagrammatic examples of embodiments of the invention wherein a detectable cleavage product is an oligonucleotide sequence. A 5'-flap sequence is cleaved by a 5'-nuclease in three optimal cleavage structures A, B and C of the invention and this oligonucleotide fragment serves as a 'cleavage enhancer' in a subsequent reaction D, forming another three-strand optimal cleavage structure with a hairpin-type FRET probe. Cleavage of this complex results in a detectable fluorescent signal as shown in stage E.

Fluorescent labels are preferred labels in detecting the cleavage products in the methods of the invention. Use of the FRET effect in detecting the fluorescent labels is, in particular, effective and recommended. FRET effect may be achieved in all methods of the invention by conjugation of two dyes, one of which may be a none-fluorescent dye or quencher, to an oligonucleotide cleavage component or probe or, in certain aspects, to specialty oligonucleotide primers. Signal generation based on FRET allows development of real time detection techniques of the invention as this is demonstrated in the Examples provided herein and in FIGS. 5-8, 11 and 14-18.

In certain methods of the invention, a nucleic acid of interest is detected using an oligonucleotide probe. The oligonucleotide probes of the invention interact with the PCR amplicons folded into secondary structures forming cleavage substrates for duplex specific nucleases. In preferred embodiments, the oligonucleotide probes are FRET-labeled as this is exemplified in FIGS. 7 and 11 and also discussed in Examples 2 and 3.

FIG. 7 shows another method embodiment of the invention that is based on the use of a 5'-nuclease activity. FIG. 11 shows an embodiment of the inventive 3'-nuclease assay. A forward primer carrying a 5'-specialty sequence hybridizes to a sense strand of a target DNA (stage A). A DNA polymerase recognizes the complex and extends the primer resulting in a double stranded amplicon (stage B). When the antisense strand is separated from its complement (stage C), it folds into a secondary structure. A FRET probe is designed to form a duplex with a respective site of the amplicon such as the duplex is separated from the amplicon duplex structure by one target strand nucleotide (stage D). These two duplexes collectively form an optimal three-strand cleavage structure which is recognized and cleaved by a 3'-nuclease, Endonuclease IV (stage E), providing a detectable fluorescent signal. The FRET probe is designed to carry a reporter dye "F" at the 3'-end whereas a quencher "Q" is attached to the 5'-end.

Examples 1, 4 and 5 demonstrate methods of the invention wherein the FRET-labeled oligonucleotide components are the specialty oligonucleotide primers of the invention. The FRET-labeled probes or primers usually contains two chromophores. The acceptor chromophore is preferably a non-fluorescent dye chosen to quench fluorescence of the reporting fluorophore (Eftink M. R. (1991) In Lakowicz J. R. (ed.), *Topics in Fluorescence Spectroscopy*. Plenum Press, New York, V.2: 53-126). By the design of the FRET-labeled oligonucleotides, endonuclease cleavage permanently separates the reporting dye from interaction with the quencher (none-fluorescent dye) providing a fluorescent signal which is detected in the methods of the invention.

IV. Reaction Components:

A. Target Nucleic Acids.

The nucleic acids of interest that can be detected by the methods of the invention can be of any nature, e.g. DNA, RNA or DNA/RNA hybrids, any sequence, structure or shape, e.g. linear or circular, single stranded or double stranded. When the nucleic acid of interest is RNA, it can be converted prior to PCR to DNA/RNA heteroduplexes or to duplex cDNA by known methods in the Art, e.g. described in Simpson D. et al (1988) *Biochem. Biophys. Res. Commun.*, 151: 487-492 and Belyaysky A. et al (1989) *Nucleic Acids Res.*, 17: 2919-2932 and the like. These methods employ a reverse transcriptase activity of certain DNA polymerase that can extend an oligonucleotide primer hybridized to a RNA template providing synthesis of complementary DNA (cDNA) in presence of deoxynucleoside 5'-triphosphates (dNTPs). Regarding the PCR-based detection assays, the methods are well known in the art under the names "reverse transcription PCR" or "RT-PCR" as described in a U.S. Pat. No. 5,168,038 of Tecott L. et al (1992), which patent is incorporated herein by reference. Certain thermostable DNA polymerases which may be used in PCR were found to express the reverse transcriptase activity, e.g. Myers T. W. and Gelfand D. H. (1991) *Biochemistry*, 30: 7661-7666. Thus the same enzyme may be used in practicing the invention performing the reverse transcription stage and PCR amplification.

Those of ordinary skill in the art will appreciate that the target nucleic acids should be sufficiently free of proteins and other substances interfering with PCR process. Many methods are available for the isolation and purification of nucleic acids of interest including commercial kits and specialty instruments. For example, nucleic acids can be isolated using organic extraction with a phenol/chloroform organic reagent followed by ethanol precipitation (Ausubel et al., eds., Current Protocols in Molecular Biology Vol. 1, Chapter 2, Section I, John Wiley & Sons, New York (1993). Solid phase adsorption method (Walsh et al. (1991) *Biotechniques*, 10: 506-513, Boom et al., U.S. Pat. No. 5,234,809) and salt-induced DNA precipitation (Miller et al (1988) *Nucleic Acids Res.*, 16: 1215) are yet other known approaches to purify nucleic acids.

B. Oligonucleotide Primers with 5'-Specialty Sequences.

PCR amplicons of the invention fold into secondary structures forming three-strand cleavage structures, in certain aspects with help of oligonucleotide cleavage components. Unlike the "accidental" secondary structures which commonly present in single stranded nucleic acids (discussed above), the secondary structures of the invention are formed due to an intelligent or purposeful design of the oligonucleotide primers. At least one primer of a pair oligonucleotide primers designed to amplify a target nucleic acid in PCR carries a 5'-specialty sequence. Examples of the specialty oligonucleotide primer designs are shown in FIG. 9.

Figure 9:
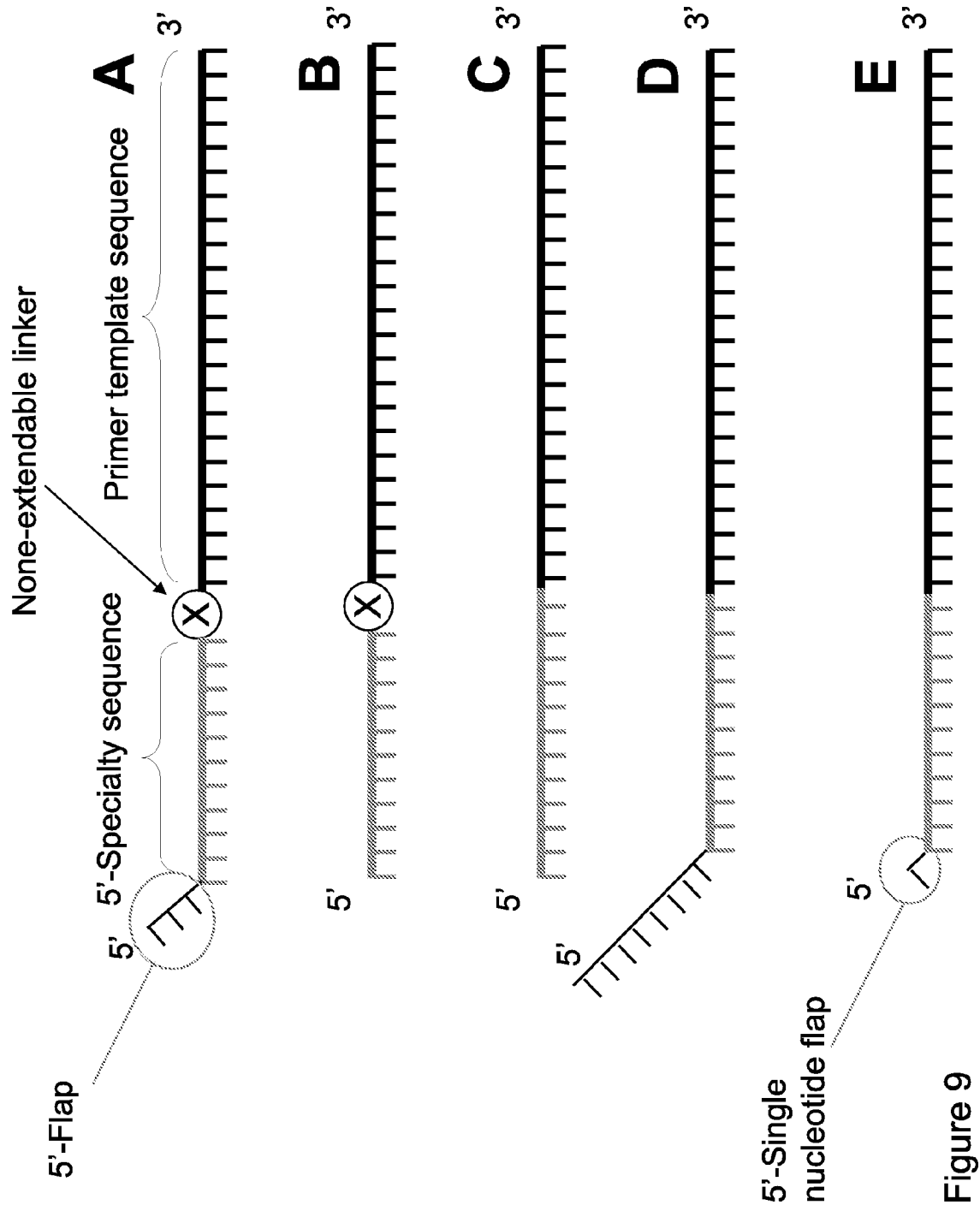
FIG. 9 shows exemplary embodiment of the designs of specialty oligonucleotide primers of the invention. As shown for the primer A, oligonucleotide primers of the invention comprise of a primer template sequence which is usually fully complementary to a respective site in a target nucleic acid. The primer template sequence is coupled by its 5'-end to the 3'-end of a 'specialty sequence' that is also complementary to the target nucleic acid but its complement is usually located between the binding sites of the amplification primer template sequences. The primer template and specialty sequences may be coupled through a non-extendable linker X (circled) (Primers A and B). Another design is shown where the primer template and specialty sequences represent uninterrupted chains of nucleotides (Primers C, D and E). The specialty primers of the invention commonly contain a 5'-flap sequence, e.g. Primers A, D and E. In preferred embodiments, the flap sequences are not complementary to nucleic acids of interest. In certain aspects, the flap sequence may serve as a detectable element (e.g., FIG. 10). The presence of a 5'-flap may also help to avoid problems described in the context of FIG. 12. Primer E is a preferred design of the specialty oligonucleotide primers of the invention used in performing the method embodiments described in FIGS. 7 and 8.

FIG. 9 shows exemplary embodiment of the designs of specialty oligonucleotide primers of the invention. As shown for the primer A, oligonucleotide primers of the invention comprise of a primer template sequence which is usually fully complementary to a respective site in a target nucleic acid. The primer template sequence is coupled by its 5'-end to the 3'-end of a 'specialty sequence' that is also complementary to the target nucleic acid but its complement is usually located between the binding sites of the amplification primer template sequences. The primer template and specialty sequences may be coupled through a non-extendable linker X (circled) (Primers A and B). Another design is shown where the primer template and specialty sequences represent uninterrupted chains of nucleotides (Primers C, D and E). The specialty primers of the invention commonly contain a 5'-flap sequence, e.g. Primers A, D and E. In preferred embodiments, the flap sequences are not complementary to nucleic acids of interest. In certain aspects, the flap sequence may serve as a detectable element (e.g., FIG. 10). The presence of a 5'-flap may also help to avoid problems described in the context of FIG. 12. Primer E is a preferred design of the specialty oligonucleotide primers of the invention used in performing the method embodiments described in the context of FIGS. 7 and 8.

The 5'-specialty sequence is an oligonucleotide fragment which is complementary to a target nucleic acid sequence, in preferred embodiments, located between the binding sites of the primer template sequences. There is no restriction in general for the design of amplicons folding into secondary structures as long as the design does not interfere with PCR process and it assures the target specific detection. In certain aspects, the specialty sequences may be partially (overlap design) or even completely complementary to the primers template sequences or their target binding sites. The rules established in the art for PCR primers design are preferably applied to the design of the primers template sequences (Gu Z. et al (2003) *J. Clin. Microbiol.*, 41: 4636-4641; Becker-Andre M. and Hahlbrock K. (1989) *Nucleic Acids Res.*, 17: 9437-9446; Freeman W. M. et al (1999) *Biotechniques*, 26:112-122, 124-125; Lutfalla G. and Uze G. (2006) *Methods Enzymol.*, 410: 386-400; Clementi M. et al (1993) *PCR Methods Appl.*, 2:191-196; Diviacco S. et al (1992) *Gene*, 122: 313-320). One of a pair PCR primers used in certain embodiments of the invention may be a conventional oligonucleotide primer comprised of a primer template sequence with no 5'-specialty sequence attached. Varying the base composition and the sequence length, the primer template sequences are selected to be sufficiently complementary to hybridize with a template strand for primer elongation to occur, i.e. the primer hybridization properties (Tm's) are adjusted to address the temperatures (annealing stage) in PCR. The target nucleic acid sequence which is complementary to the specialty sequence is produced in PCR as result of the primer extension. Since the specialty primer is incorporated into the amplification product, this prompts the amplicon to fold into a steam-loop secondary structure, as exemplified in FIGS. 5-8 and 10-13.

In many cases, the PCR amplicon that incorporates the specialty primer is the detected product, e.g. as exemplified in FIGS. 5, 6, 8 and 11. In certain embodiments, the detected product is a replica of this amplicon which also folds into a secondary structure as shown, for example, in the method of FIG. 7. In certain embodiments, the primer template and specialty sequences may represent an uninterrupted chain of nucleotides (Structures C, D and E in FIG. 9).

When such an oligonucleotide primer is incorporated into an amplicon and the amplicon serves as a template in next PCR cycle, a DNA polymerase is able to replicate the amplicon extending the complementary strand to the 5'-end of the template including the specialty sequence of this primer (e.g. FIGS. 6 and 7). Such a design represents a "fully extendable" oligonucleotide primer. In other embodiments, the 3'-end of the specialty sequence may be coupled to the 5'-end of the primer template sequence through a "non-extendable linker" that does not support the strand extension by a DNA polymerase and the complementary strand synthesis is terminated once the polymerase reaches the 5'-end of the primer template sequence. These "partially extendable" oligonucleotide primers, e.g. Structures A and B in FIG. 9, may be effectively used in many derivative forms of the methods of the invention. Those of ordinary skill in the art will appreciate that in many aspects the partially extendable specialty primers is a preferred design because the exclusion of a specialty sequence from the amplification process helps to avoid certain potential problems of the invention, e.g. described in FIGS. 12 and 13.

DNA polymerases are sensitive to the DNA template structure. Virtually any moiety or combination of moieties that are substantially different from the nucleotide structure may be used in the invention as "non-extendable linkers" to design the "partially extendable" oligonucleotide specialty primers. Examples of such moieties include but not limited to the commercially available compounds commonly applied in oligonucleotide synthesis such as universal bases, abasic sites, and also propane diol, triethylene glycol, 4-butyramidomethyl-1-(2-nitrophenyl)-ethyl linkers (Glen Research) and the like. Hexaethylene glycol linker which is usually used for the same purpose in design of Scorpion primers (e.g. described in Whitcombe D. et al (1999) *Nature Biotech.*, 17: 804-807; Thelwell N. et al (2000) *Nucleic Acids Res.*, 28: 3752-3761) was successfully used in the Examples of the invention provided herein.

Oligonucleotide primers of the invention may incorporate sequences other than the specialty and primer template sequences. For example, relatively G/C-rich sequences may be inserted to improve the primer hybridization properties during PCR. These sequences may be part of a primer-dimer eliminating technology described in Brownie J. et al (1997) *Nucleic Acids Res.*, 25: 3235-3241. In such cases, these "additional" sequences are preferably positioned between the specialty and primer template sequences. In certain aspects, the oligonucleotide primers of the invention are cleaved once they are incorporated into amplicons which fold into a secondary structure resulting in detectable cleavage products as shown in FIGS. 5, 6, 8 and 10. Thus, the oligonucleotide primers used herein may incorporate detectable labels, e.g. dyes, mass tags, radioactive elements, etc., or 5'-flap sequences. In cases when the detection is based on FRET effect, the oligonucleotide primers are designed to carry two conjugated dyes at least one of each is a fluorescent dye as exemplified in FIGS. 5, 6 and 8. The oligonucleotide primers of the invention may also contain "structural modifications" that may be used for the reasons other than the detection, for example, to improve the sequence hybridization properties (e.g. duplex-stabilizing modified bases).

Aspects of the present invention may be practiced in many derivative forms, several examples of which are shown in FIGS. 5, 6, 7, 8 and 11. The detection can performed using 5'- or 3'-nucleases in real time or in a post-PCR format. One of a pair or both PCR primers can carry specialty sequences. Multiple nucleic acids of interest can be detected using the methods of the invention (multiplex PCR). The methods of the invention can be used to measure the amount of the target nucleic acids in samples (quantitative PCR) or they can be performed to detect polymorphic variations (qualitative PCR). There are many variables in the assay design and many derivative forms of the invention, and detailed guidance for the specialty oligonucleotide primer design in every particular embodiment of the invention is not included herein. However, given the present teachings, the Examples provided herein (FIGS. 14-18), and the knowledge in the relevant art, such variables and derivative forms and certain generic rules will be appreciated by those of ordinary skill in the art of detection reactions employing DNA nucleases.

The partially extendable oligonucleotide primers (Structures A and B in FIG. 9) is a preferred design of the specialty primers unless the use of the fully extendable primers is required by a specific choice of the methods applied, e.g. as shown in FIGS. 7 and 8. This design helps avoid the potential PCR-terminating pathways exemplified in FIGS. 12 and 13. However, application of the fully extendable primers may be a preferred design for certain methods of the invention regardless the referred above problem. An example of such an assay is shown in FIG. 11.

FIG. 11 shows an embodiment of the inventive 3'-nuclease assay. A forward primer carrying a 5'-specialty sequence hybridizes to a sense strand of a target DNA (stage A). A DNA polymerase recognizes the complex and extends the primer resulting in a double stranded amplicon (stage B). When the antisense strand is separated from its complement (stage C), it folds into a secondary structure. A FRET probe is designed to form a duplex with a respective site of the amplicon such as the duplex is separated from the amplicon duplex structure by one target strand nucleotide (stage D). These two duplexes collectively form an optimal three-strand cleavage structure which is recognized and cleaved by a 3'-nuclease, Endonuclease IV (stage E), providing a detectable fluorescent signal. The FRET probe is designed to carry a reporter dye "F" at the 3'-end whereas a quencher "Q" is attached to the 5'-end.

Figure 12:
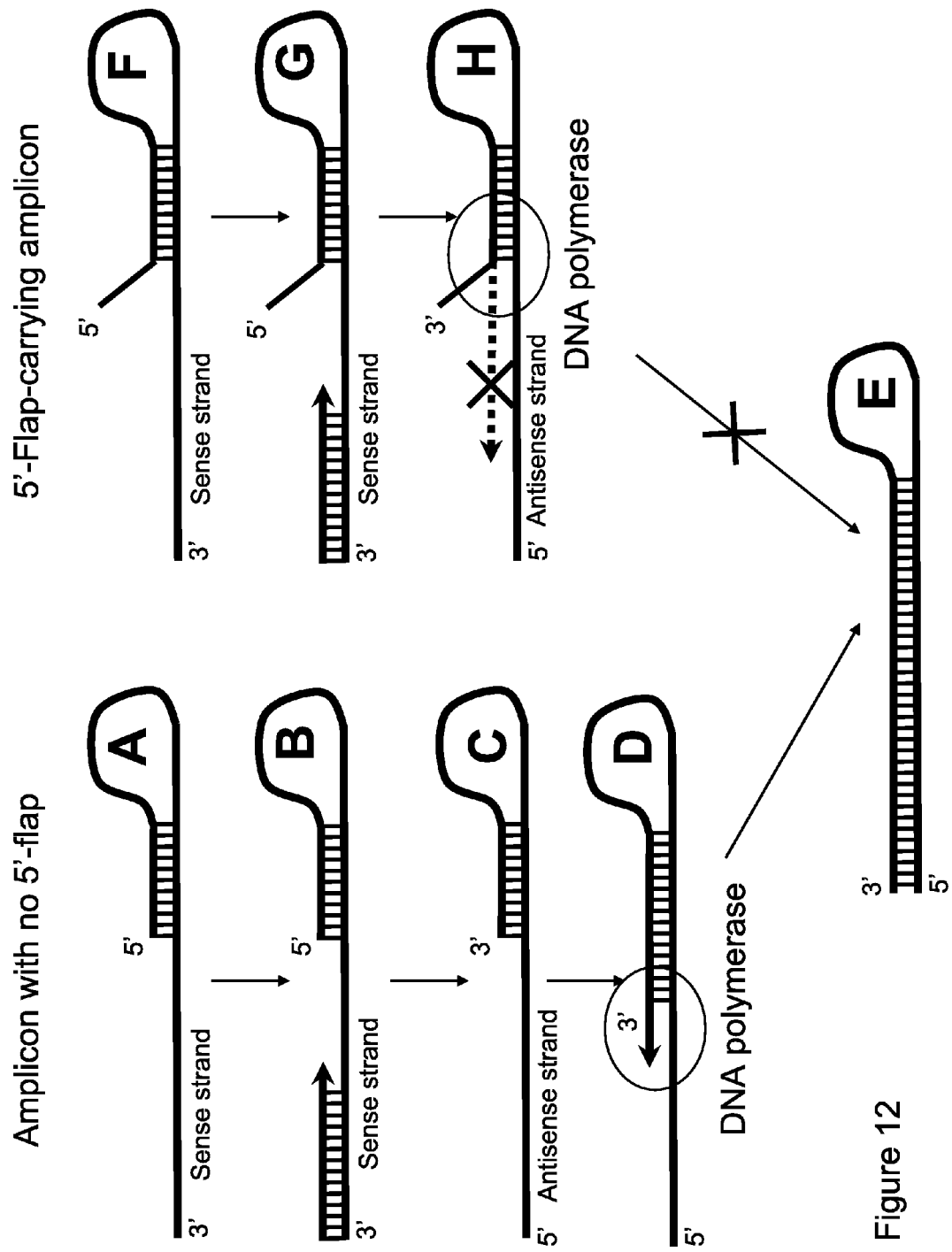
FIGS. 12A-12H diagrammatically shows a potential problem associated with amplicons forming secondary structures. Use of a specialty oligonucleotide primers C (FIG. 9) in PCR leads to formation of an amplicon with a secondary structure (stage A). This amplicon serves as a template in a subsequent primer extension reaction (stage B) providing a replica, a complementary antisense strand (stage C), which also folds into a secondary structure. This secondary structure is recognized by a DNA polymerase as an extension complex and this leads to synthesis of a complementary strand (stage D) resulting in formation of a hairpin-like molecule (stage E). The structure E represents a "terminating" product of PCR. Depending on the efficiency of the reaction that leads to formation of the structure E, PCR may slow down to an unacceptable degree. As shown in this diagram, the 5'-flap-carrying amplicons do not result in formation of the structure E. However, if 5'-nuclease activity is present, during PCR, the 5'-flap may be cleaved and this may result in formation of the amplification-terminating structure E. Such a scenario is shown in FIG. 13.
Figure 13:
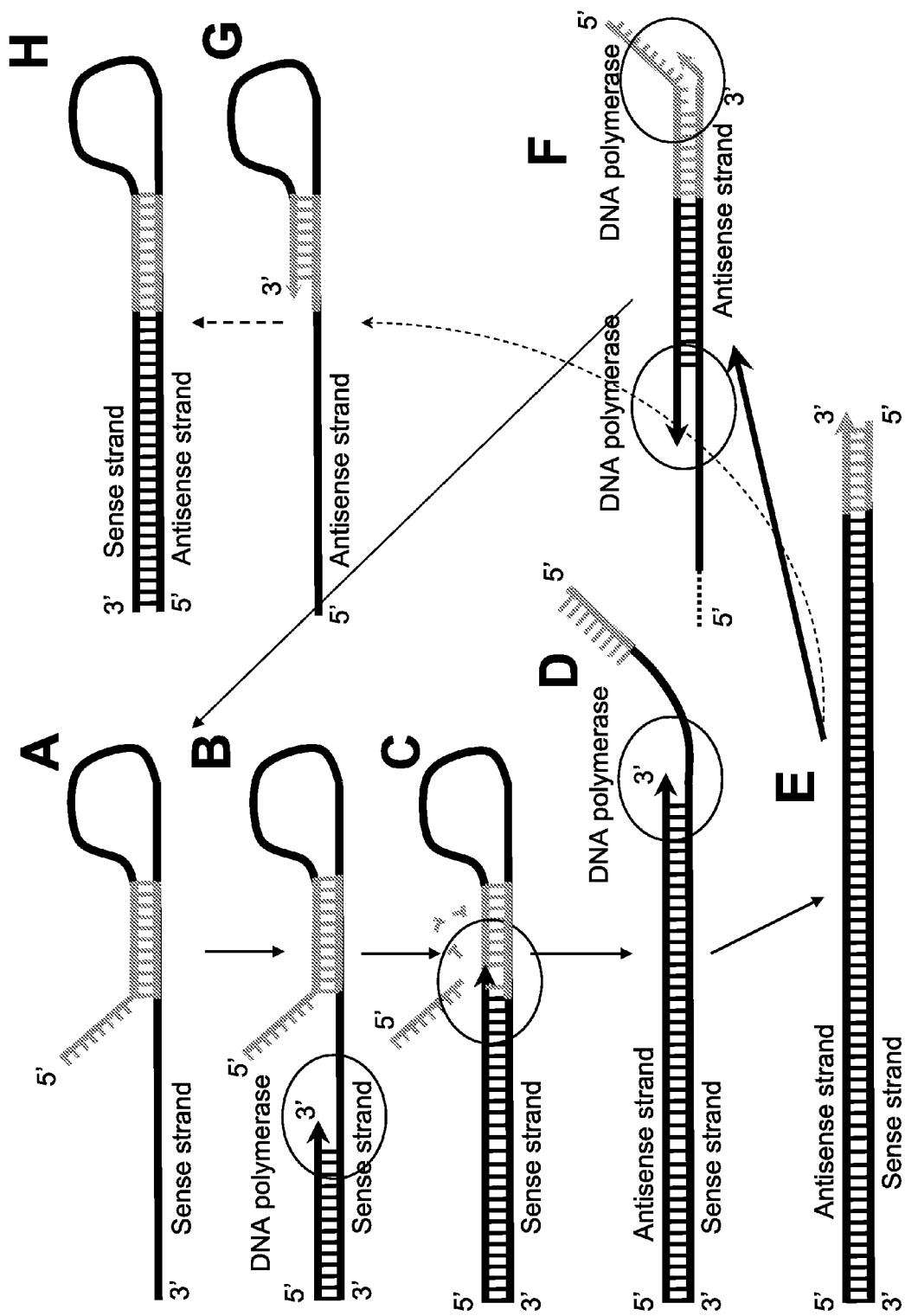
FIG. 13 diagrammatically shows an anticipated PCR pathway in cases when an amplicon carrying a 5'-flap secondary structure element (stage A) is cleaved by a 5'-nuclease during the primer extension (stages B and C). The specialty sequence and its target complement are shown in gray color for the illustrative convenience. Once the 5'-flap is cleaved; a specialty sequence segment may be displaced by a DNA polymerase (stage D) providing the double stranded amplicon shown in stage E. After the strand separation at high temperature (95° C.), the "truncated" antisense strand may fold into a secondary structure G which, due to a perfect complementarity of the 3'-end segment, may be recognized by the DNA polymerase and extended to a PCR-terminating structure H. This pathway could occur to some extent at any stage of PCR. However, it would expected to accelerate at the late PCR cycles when a specialty oligonucleotide primer (creating the structure A) is substantially reduced in concentration due to its consumption. At the early cycles of PCR, when the specialty primer is in a significant excess over the PCR products, the pathway leading to the structure F is anticipated to prevail. Although truncated, the antisense strand of the structure E still serves as a template for the specialty primer (stage F). Moreover, hybridization of the specialty primer with this amplicon leads to "restoring" of the truncated end as shown in the stage F.

Endonuclease IV from *E. coli* does not survive in PCR and this prompts the detection reaction to be performed in post-PCR format. In one aspect, the specialty primer B (FIG. 9) may be used to create respectively an optimal cleavage structure shown in FIG. 4. In yet another aspect, the specialty oligonucleotide primer C may bring an advantage to the assay. For example, two PCR primers are designed to perform at 75° C. annealing temperatures but the specialty sequence in the Primer C (FIG. 9) is selected to be too short to form a stable secondary structure within an amplicon at these elevated temperature conditions. However, the secondary structure is effectively formed during the detection stage at temperatures 45-50° C. While a detected amplicon participates in an optimal cleavage structure formation (FIG. 11), the replica of the detected amplicon would fold into a secondary structure shown in FIG. 12 (Amplicon with no 5'-flap). This would lead to a strand extension providing the structure E (FIG. 12). In many cases of the invention, the amplicon strand needs to be in a single-stranded state in order to be detected. Two complementary PCR amplicon strands tend to reanneal and this may correspondingly reduce the concentration of the detected amplicon. Extension of a non-detected amplicon to the structure E would eliminate this effect maintaining the concentration of the detected strand steady during the detection stage. The amplicon strand reannealing would obviously compete with the formation of structure E, but the strand separation stage (>90° C.) followed by the reaction exposure to low temperature stage (45-50° C.) may be repeated as often as desired before the initiating the detection (i.e. adding the detection components, FRET-probes and the endonuclease IV) converting more of the none-detected amplicon into the structure E and thus increasing the concentration of the single stranded detected amplicon strand. Moreover, DNA polymerase may be in a competition with Endo IV for binding to the three-strand cleavage structure, especially when the 3'-tail has been removed. Extension of the non-detected amplicon strand would occupy DNA polymerase allowing to the endonuclease IV to perform, preferably in a cycling mode.

As has been shown in the Examples of the invention, overly stable secondary structures within the PCR amplicons may interfere with PCR usually resulting in a "delayed" threshold (CO values in real time assays. If the secondary structure is too unstable, it may not serve the purpose of the invention or provide little help in detecting the amplification products (e.g. see 6, 7 and 8-mer curves in FIG. 15B). Nevertheless, as has been proved in the Examples of the invention, optimal designs of the specialty oligonucleotide primers can always be found for every particular method of the invention when the amplicon secondary structure has little, if any, effect on PCR efficiency while significantly enhancing the detection stage. An optimal stability of the amplicon secondary structure is a function of many parameters but mainly the temperature of the detection stage. On the other hand, delaying the threshold value does not change the functional relationship between the initial target nucleic concentration and $C_t$. Those of ordinary skill in the art of real time PCR will agree that use of the methods of the invention with a "delayed" detection could actually be beneficial in, e.g. detecting the targets of reference which are usually present in samples at high concentration.

C. Oligonucleotide Cleavage Components.

In certain embodiments of the invention, the three-strand cleavage structures are formed by oligonucleotide cleavage components which hybridize to amplification products of the invention that fold into a secondary structures. Examples of the methods of the invention wherein the oligonucleotide cleavage components are used may be found in FIGS. 6, 7, 10 and 11.

The three-strand cleavage structures are cleaved in the presence of duplex-specific nucleases generating a detectable cleavage product. In certain aspects, the oligonucleotide cleavage component is not of the cleaved strand and is named herein as a "cleavage enhancer" (FIGS. 6 and 10). In other aspects, the oligonucleotide cleavage component represents the strand that is cleaved. In such cases, it serves as an "oligonucleotide probe" (FIGS. 7, 10 and 11). The core structure and specific structural elements of the oligonucleotide cleavage component are determined by a specific method of the invention. For example, when the oligonucleotide cleavage component serves as a cleavage enhancer in a 5'-nuclease assay, it is substantially complementary to an amplicon site that is in proximity to the specialty sequence binding site, preferably forming an optimal three-strand cleavage structure as shown in FIG. 2. In preferred aspects, the 3'-nucleotide of the cleavage enhancer is not in a complex with the target counterpart (contains a 3'-single nucleotide flap). The 3'-flap may be a natural nucleoside which is not complementary to the target amplicon. However, this approach may have limitations, especially, if the cleavage component is designed to have a Tm value above the annealing temperature in PCR. Although the priming ability of the cleavage component is substantially reduced in reaction with DNA polymerase, it may be eventually extended and this would lead to amplification of an amplicon which is shorter than the target amplicon providing an art-recognized effect of amplification interference. This may be readily avoided, for example, when an unnatural or modified nucleoside, e.g. universal base, is incorporated to the 3'-end of the cleavage enhancer using, for example, 5'-dimethoxytrityl-2'-deoxy-3-nitropyrrole-ribofuranosyl, 3'-succinoyl-long chain alkylamino-CPG or 5'-dimethoxytrityl-2'-deoxy-5-nitroindole-ribofuranosyl, 3'-succinoyl-long chain alkylamino-CPG (Glen Research) in oligonucleotide automated synthesis. Cleavage enhancers may be designed to have Tm values in a broad range, above or below the annealing temperature or temperature of the detection stage (when the assay is a post-PCR assay). The Tm value of the cleavage enhancer is preferably not more than 5° C. lower than the detection reaction temperature. Those of ordinary skill in the art will appreciate that the enhancer with elevated hybridization properties may interfere to a certain degree with the primer extension in a real time assay shown in FIG. 6. The preferred design of a cleavage enhancer is when it has Tm in a range of −5 to +5° C. from the reaction temperature.

In certain embodiments of the invention, the oligonucleotide cleavage component is an oligonucleotide probe providing a cleaving strand to the three-strand cleavage structure. Examples of these assays are shown in FIGS. 7 and 11. The assay of the FIG. 7 is also discussed in Examples 2 and 3.

The oligonucleotide probes of the invention incorporate detectable elements like labels, e.g. dye, mass tag, etc., or 5'-flap sequences (see Structure B in FIG. 10). In certain aspects, the probe cleavage may be performed in a cycling mode when the target amplicon is recycled and more than one probe can be cleaved per the target molecule (e.g. methods in FIGS. 7 and 11). This is usually the case when the probe concentration exceeds the concentration of the respective PCR primers which, in term, determine the yield of the detected amplicon (Examples 2 and 3). In preferred embodiments, the oligonucleotide probes contain two dyes which are in a FRET interaction and which are permanently separated due to the cleavage providing a detectable fluorescent signal. In addition to dyes, universal bases and linkers, the oligonucleotide cleavage components of the invention may contain other structural modifications like modified bases, including the duplex-stabilizing ones, conjugated intercalators, minor groove binders, etc.

D. Structural Modification and Synthesis of Oligonucleotide Components.

The oligonucleotide components of the invention such as oligonucleotide primers, cleavage enhancers and probes may be synthesized using techniques that are well known in the Art. Although the primers can be prepared by, for example, cloning and restriction digest analysis of appropriate sequences; direct chemical synthesis is a preferred approach. Oligonucleotide components can be prepared by a suitable chemical synthesis method, including, for example, the phosphodiester method disclosed in Brown E. L. et al (1979) *Methods Enzymol.,* 68*:* 109-151, the phosphotriester method described in Narang S. A. et al (1979) *Methods Enzymol.,* 68: 90-98. The preferred approach is the diethylphosphoramidate method disclosed in Beaucage S. L., Caruthers M. H. (1981) *Tetrahedron Lett.,* 22: 1859-1862, in combination with the solid support method disclosed in Caruthers M. H., Matteucci M. D. (1984) U.S. Pat. No. 4,458,066 and performed using one of commercial automated oligonucleotide synthesizer.

When oligonucleotide primers and probes of the invention need to be labeled with a fluorescent dye, a wide range of fluorophores may be applied in probe and primer designs and synthesis. Available fluorophores include but not limited to coumarin, fluorescein (FAM, usually 6-fluorescein or 6-FAM), tetrachlorofluorescein (TET), hexachloro fluorescein (HEX), rhodamine, tetramethylrhodamine, BODIPY, Cy3, Cy5, Cy7, Texas red and ROX. Fluorophores may be chosen to absorb and emit in the visible spectrum or outside the visible spectrum, such as in the ultraviolet or infrared ranges. FRET probes and specialty oligonucleotide primers of the invention commonly incorporate a pair of fluorophores, one of which may be a none-fluorescent chromophore (commonly referred as a "dark quencher"). Suitable dark quenchers described in the Art include Dabcyl and its derivatives like Methyl Red. Commercial none-fluorescent quenchers, e.g. Eclipse (Glen Research) and BHQ1, BHQ2, BHQ3 (Biosearch Technologies), may be also used for synthesis of FRET probes of the invention. Preferred quenchers are either dark quenchers or fluorophores that do not fluoresce in the chosen detection range of an assay.

The donor and acceptor fluorophores for manufacturing of the labeled oligonucleotide components of the invention may be selected from suitable fluorescent groups, e.g. 6-FAM (6-carboxyfluorescein); 6-hexachloro-fluorescein ([4,7,2',4', 5',7'-hexachloro-(3',6'-dipivaloylfluoresceinyl)-5-carboxylic acid]); 6-tetrachloro-fluorescein ([4,7,2',7'-tetrachloro-(3',6'-dipivaloylfluoresceinyl)-6-carboxylic acid]); 6-TAMRA (6-carboxytetramethylrhodamine; Dabcyl (4-((4-(dimethylamino)phenyl)azo)benzoic acid); Cy5 (Indodicarbocyanine-5); Cy3 (Indo-dicarbocyanine-3); and the like.

Oligonucleotide components of the invention may contain structural modifications other than fluorescent dyes and linkers, e.g. different moieties, residues and nucleotide analogs which are usually of a synthetic nature and which are not commonly present in natural nucleic acids. Modified nucleoside or nucleotide analogs which rarely present in natural nucleic acid may be incorporated synthetically into oligonucleotide components, for example, inosine (hypoxanthine), 5-bromouracil, 5-methylcytosine, 5-iodouracil, 2-aminoadenosine, 6-methyladenosine, preudouridine and the like. Duplex-stabilizing modifications are preferred structural modifications because, in general, use of these modifications allow to reduce the length of oligonucleotide components or, alternatively, to use more stringent PCR conditions providing better amplification results. Those of ordinary skill in the art will appreciate that there are certain rules and limits in use of the structural modifications in oligonucleotide primers. 3' end of the primers must not be blocked to initiate the DNA synthesis. For example, when minor groove binders (MGB) are conjugated to enhance the primer hybridization properties, the MGB moiety is coupled to the 5' end (Afonina I. et al (1997) *Nucleic Acids Res.,* 25: 2657-2660). This approach may be used in design of conventional PCR primers but should be avoided in the specialty oligonucleotide primers. Certain nucleotide analogs can be incorporated into the oligonucleotide primers, although the number of these modifications may be limited. Examples of such nucleotide analogs include but not limited to "universal" bases (Burgner D. et al (2004) *Nucleosides Nucleotides Nucleic Acids,* 23: 755-765) and "locked nucleic acids" ("LNA") (Latorra D. et al (2003) *Mol. Cell. Probes,* 17: 253-259; Latorra D. et al (2003) *Hum. Mutat.,* 22:79-85; Di Giusto D. A. and King G. C. (2004) *Nucleic Acids Res.,* 32: e32) in accordance with teaching of the cited manuscripts which are incorporated herein by reference. Certain base-modified nucleotide analogs are well adopted by DNA polymerases and these analogs can be used in primer design without any limits. Examples of such base-modified nucleotide analogs include but not limited to 5-methyl cytosine and 2,6-diamino purine (Lebedev Y. et al (1996) *Genet. Anal.,* 13:15-21). However, in many cases of structural modifications including the duplex-stabilizing ones, their effect on duplex-specific nucleases is unknown and additional restrictions on use may apply, especially when the oligonucleotide primers and probes provide a cleavable strand into the three-strand structure of the invention. The oligonucleotide probes do not participate in DNA amplification and these oligonucleotide components may be generally less restricted in use of the structural modifications. The duplex-specific endonucleases are anticipated to be especially sensitive to the structural "alterations" within their binding and cleavage sites. Based on this rational, those of ordinary skill in the art will appreciate that the structural modifications that are suspected to interfere with nucleases or their effect on the enzymes are unknown should be located away from the cleaved phosphodiester bond. For example, conventional FRET probes can carry a minor groove binding (MGB) moiety conjugated to either end. 5'-MGB-conjugated FRET probes are not cleaved in PCR due to the MGB interference and these probes provide signal according to a hybridization-triggered mechanism of action as described in Vermeulen N. et al (2002) *J. Clin. Ligand Assay,* 25: 268-275. For the same reason, incorporation of 5'-MGB is not recommended for the cleavage enhancers, if they are used in a real time assay. 3'-MGB-conjugated FRET probes are not blocked from 5'-nuclease degradation and these probes generate fluorescent signal in PCR (TaqMan assay) due to the cleavage by Taq polymerase as exemplified in Kutyavin I. V. et al (2000) *Nucleic Acids Res.,* 28: 655-661. This information can be used in design of the oligonucleotide probes of the invention. For example, if 5'-nuclease is used to cleave the three-strand cleavage structure and the probe provides the cleavable strand, MGB-moiety should be conjugated to the 3'-end of the probe. In contrast, if 3'-nuclease, e.g. Endonuclease IV, is used for the same reason, the MGB-moiety should be conjugated to the 5'-end of the probe. Placing the structural modifications within 4-6 nucleotides on either side from the cleavage point should be avoided unless the compatibility of a structural modification with a specific nuclease has been studied and verified. A list of the structural modifications that may be used in preparing oligonucleotide probes of the invention includes but not limited to 2,6-diamino purine and 5-methyl cytosine nucleotide analogues (Lebedev Y. et al (1996) *Genet. Anal.*, 13, 15-21), sugar-modified nucleotide analogs like LNA (Johnson M. P. et al (2004) *Nucleic Acids Res.*, 32: e55; Simeonov A. and Nikiforov T. T. (2002) *Nucleic Acids Res.*, 30: e91) and the like.

Oligonucleotide primers including 5'-specialty primers, cleavage enhancers and probes may be designed according to basic rules and specifications established in the art, including certain restrictions and limitations discussed herein. There are certain common requirements to the oligonucleotide components, for example, the hybridization properties of the oligonucleotide need to address the temperature of a particular reaction, usually referred as melting temperature (Tm). Tm defines a temperature at which a complementary complex of an oligonucleotide component with target nucleic acid becomes half dissociated into single strands. A simple estimate of the Tm value may be calculated using the equation $Tm=81.5+0.41(\% G+C)$, when a nucleic acid is in aqueous solution at 1 M NaCl. More accurate calculations can be made using the base pair thermodynamics of a "nearest-neighbors" approach (Breslauer K. J. et al (1986) *Proc. Natl. Acad. Sci. USA*, 83: 3746-3750; SantaLucia J. Jr. (1998) *Proc. Natl. Acad. Sci. USA*, 95: 1460-1465). Commercial programs, including Oligo™, Primer Design and programs available on the internet, including Primer3 and Oligo Calculator can be also used to calculate a Tm of a nucleic acid sequence useful according to the invention. Commercial programs, e.g. Visual OMP (DNA software), Beacon designer 7.00 (Premier Biosoft International), may be also helpful. Melting temperatures of secondary structures may be determined using approach and algorithm described in e.g. Zuker M. and Jacobsen A. B. (1995) *Nucleic Acids Res.*, 23: 2791-2797; Walter A. E. et al (1994) *Proc. Natl. Acad. Sci. USA*, 91: 9218-9222.

The nearest-neighbors thermodynamic parameters have been determined only for natural bases (see Breslauer K. J. et al (1986) *Proc. Natl. Acad. Sci. USA*, 83: 3746-3750). Analogous values for modified nucleotide analogs are not available making impossible accurate prediction of Tm values for the base modified oligonucleotide primers and probe of the invention. However, estimates may be made providing that substitution of one deoxyadenosine by d(2-amA) (2,6-diaminopurine) and one thymidine by 5-propynyl uridine increase Tm value of a randomly taken 20-mer oligonucleotide by 0.8-1° C. Tm values for MGB-conjugated oligonucleotide primers and probes may be assessed according to guidance of Kutyavin I. V. et al (1997) *Nucleic Acids Res.*, 25: 3718-3723. Melting temperatures of 3'-MGB TaqMan probes can be predicted using commercial software provided by the manufacturer (ABI, California, USA).

E. DNA Polymerases.

DNA polymerases are key components in practicing nucleic acid assays of the present invention. DNA polymerases useful according to the invention may be native polymerases as well as polymerase mutants, which are commonly modified to improve certain performance characteristics or to eliminate 5' to 3' and/or 3' to 5' exo/endo nuclease activities that may be found in many native enzymes. Nucleic acid polymerases can possess different degrees of thermostability. To perform in PCR, DNA polymerase should be stable at temperatures >90° C., preferably >95° C. and even more preferably >100° C. Examples of thermostable DNA polymerases which are useful for performing the methods of the invention include but not limited to Pfu, Taq, Vent, Deep Vent and UlTma DNA polymerases and other polymerase from Thermus species or from *Thermotoga maritima*. DNA polymerases used in the methods of the invention may incorporate 5'→3' and 3'→5' "associated" nuclease activities. For example, Taq DNA polymerase from *Thermus aquaticus* has duplex-specific 5'-nuclease activity and this may be used in 5'-nuclease assays of the invention. JumpStart DNA polymerase from Sigma (antibody blocked Taq polymerase) was used in Examples provided herein. The presence or absence in DNA polymerases of the 3'→5' nuclease activity, which is known in the art under a name "proofreading" nuclease activity, is not as significant for many methods of the invention as other characteristics such as the enzyme processivity, fidelity and DNA synthesis speed. However, use of the proofreading polymerases like Pfu DNA polymerase is the least preferred in the methods of FIGS. 7 and 8 because the 3'→5' nuclease activity may hydrolyze the 3'-single nucleotide flap in the amplicons of the invention providing an extension point and leading to the PCR terminating structure E (FIG. 12).

F. Duplex-Specific Nucleases.

Duplex-specific nucleases are important components of the detection reactions of the invention. These nucleases recognize the three-strand structures providing the cleavage and consequent detection of the cleaved products. The duplex-specific nucleases useful in practicing the invention do not substantially cleave either oligonucleotide probes or primers when they are in a single stranded state and when they are not hybridized to the target nucleic acids or PCR amplicons. Cleavage efficiency of duplex-specific nucleases of the invention in many occasions is significantly improved when yet another duplex structure appears in proximity of their cleavage site. This property of the endonucleases is used herein in cleaving the three-strand cleavage structures in PCR detection assays. Examples of the three-strand cleavage structures of the invention are shown in FIGS. 1-4.

The duplex-specific nucleases may be divided on two main classes, "5'-nucleases" and "3'-nucleases" (5'- or 3'-nuclease activities respectively). 5'-Nucleases cleave 5'-strand of the three-strand cleavage structures while 3'-nucleases cleave the 3'-strand. Duplex-specific 5'-nuclease activities useful in practicing the invention may be found in many DNA polymerases, e.g. *E. coli* DNA polymerase I and DNA polymerase isolated from *Thermus aquaticus* (Taq), *Thermus thermophilus* (Tth), *Pyrococcus furiosus* (Pfu) and *Thermus flavus* (Tfl). In certain preferred embodiments of the invention, both assay activities, DNA polymerase and 5'-nuclease, are provided by the same enzyme, for example, Taq polymerase. "Flap endonucleases" ("FENs") are yet another example of 5'-duplex-specific nucleases that may be used to cleave the three-strand structures of the invention. Flap endonucleases are a class of nucleolytic enzymes that act as structure specific 5'-exo and 5'-endonucleases during DNA replication, DNA repair and DNA recombination (Lyamichev V. et al (1993) Science, 260: 778-783). Flap endonucleases have been identified in eukaryotes, prokaryotes, archea and viruses. Optimal cleavage structures for 5'-nucleases and FENs is shown on FIG. 2. Preferred 5'-nucleases of the invention are thermophilic. However, methophilic 5'-endonucleases may be used in certain post-PCR assays of the invention.

3'-nucleases of the invention are enzymes which act in a duplex specific fashion hydrolyzing 3'-strand of the three-strand cleavage structures (FIG. 1). Examples of such enzymes may be found among exo and endonucleases participated in repair of DNA. AP endonucleases are particularly useful enzymes for performing 3'-nuclease assays of the invention. Examples of AP endonuclease include two structurally different families. Exonuclease III and Endonuclease IV (Endo IV) of E. coli are representatives of these two AP nuclease families. Both enzymes may be used in the 3'-endonuclease assays of the invention. However the preferred 3'-nucleases are Endonuclease IV and human AP endonuclease (Strauss P. R. et al (1997) J. Biol. Chem., 272: 1302-1307) because Exonuclease III expresses 3' terminal diesterase (Strauss P. R. and O'Regan N. E. (2001) DNA damage and repair. Humana Press, Totowa, Vol. III, pp. 43-86; Weiss B. (1998) DNA damage and repair. Humana Press, Totowa, Vol. I, 85-96; Levin J. D. et al (1988) J. Biol. Chem., 263, 8066-8071). It was also found that Endo IV is fairly heat-stable (Ljungquist S. (1977) J. Biol. Chem., 252, 2808-2814) and it begins to denature at 70° C. (Haas B. J. et al (1999) J. Bacteriol., 181: 2834-2839). Endonuclease IV from E. coli does not cleave internucleotide phosphodiester bond but it efficiently cleaves a DNA strand in duplexes containing abasic cites and it also removes phosphates and other tails from the 3'-end of a three-strand cleavage structure as shown in FIGS. 3 and 4. Although the Endo IV is duplex-specific but presence of another duplex structure nearby the 3'-cleaved end was shown to accelerate the cleavage. The three-strand cleavage structures apparently simulate the 3'-endonuclease natural substrates commonly found in DNA lesions. Although Endonuclease IV from E. coli does not survive in PCR, use of methophilic endonucleases in post-PCR detection may be advantageous in certain aspects. A detailed guidance in conducting 3'-nuclease assay of the invention (shown in FIG. 11) may be found in Kutyavin I. V. et al (2004) US Patent Application #20040101893; Kutyavin I. V. et al (2006) Nucleic Acids Res., 34: e 128.

V. Examples of the Methods of the Invention:

Example 1

The design of oligonucleotide components, forward and reverse primers, used in Example 1 and results of the experiments, real time fluorescent curves, are shown in FIG. 14.

Figure 5:
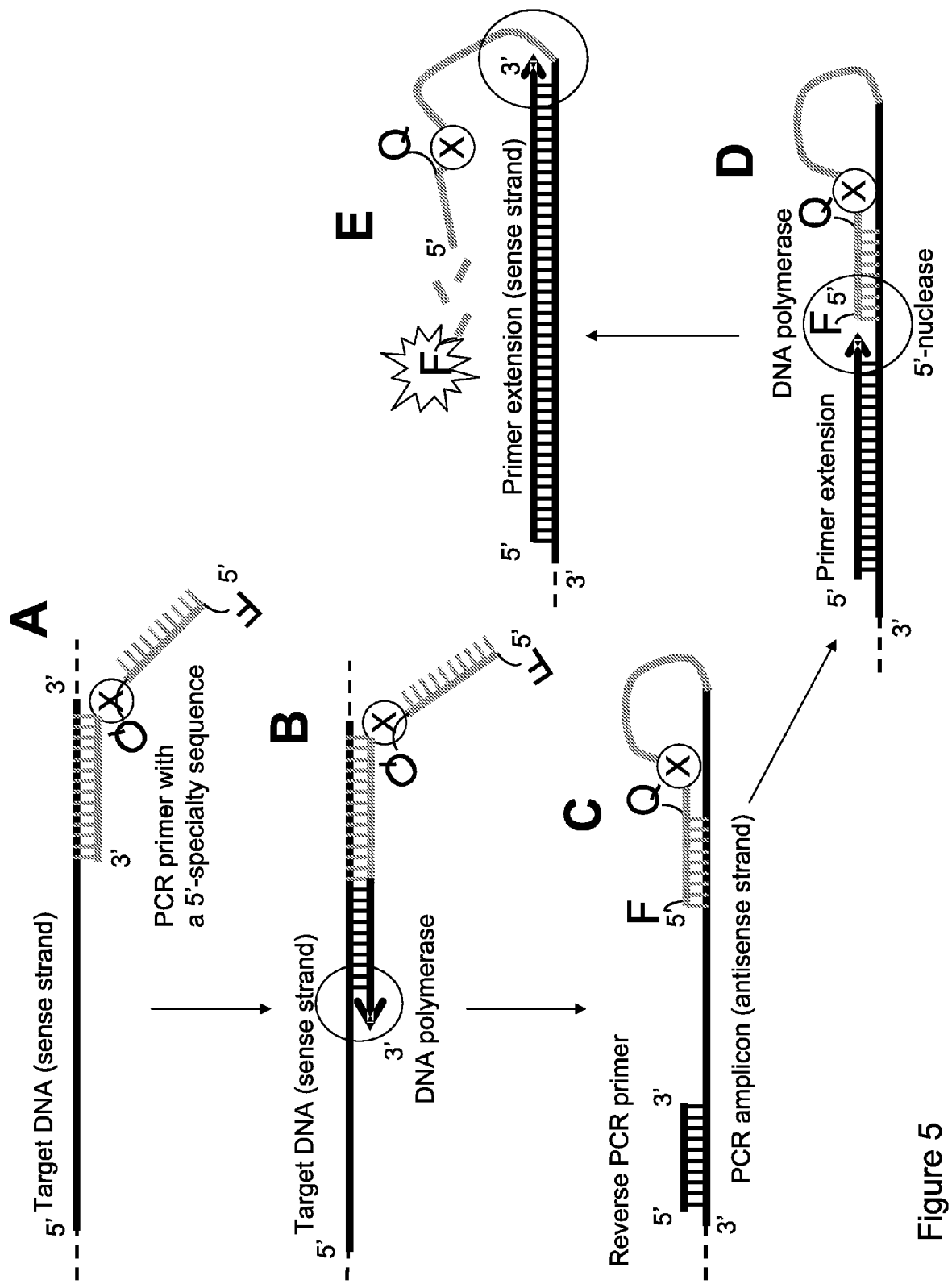
FIG. 5 shows an example of one method embodiment of the invention wherein a 5'-nuclease cleavage structure is created during an oligonucleotide primer extension and detection is based on use of FRET effect. A forward PCR primer incorporates a 5'-specialty sequence carrying a reporting fluorescent dye "F" conjugated to the 5'-end and a quencher "Q" dye conjugated to the 3'-end of the specialty sequence. The 3'-end of the specialty sequence is coupled to the 5'-end of a primer template sequence through a none-extendable linker "X" (circled). The "template sequence" of a specialty oligonucleotide primer hybridizes to a sense strand of a target DNA (stage A) wherein it is recognized by a DNA polymerase and extended (stage B) resulting in DNA duplex. The specialty sequence is designed to be complementary to a sequence within the extended antisense strand. After a strand denaturation stage (e.g., 95° C.), an antisense amplicon which incorporates the specialty primer folds into a secondary structure (stage C). Hybridization with a reverse oligonucleotide primer leads to extension by the DNA polymerase (stage D). During the reverse primer extension, when a 3'-end of the extension product reaches the 5'-end of the folded amplicon, the 'three-strand cleavage structure' is created and a 5'-nuclease cleaves the 5'-strand of the antisense amplicon (stage E) releasing the reporting dye "F" from FRET interaction with the quencher "Q", thus providing a detectable fluorescent signal. The DNA polymerase displaces an uncleaved part of the hybridized specialty sequence and continues the strand extension until it reaches the none-extendable linker "X." After completion of the stage E, followed by a denaturation stage, a newly synthesized sense amplicon may again hybridize with another molecule of the forward specialty primer initiating another cycle of the PCR.

FIG. 14 shows experimental data from performing real time FRET assays according to a method of the invention as described in the context of FIG. 5. FIG. 14A shows the design of oligonucleotide components used in the assays. Reverse primers #2-6 contained FRET-labeled specialty sequences of variable length but the same primer template sequence as shown for the reverse primer (SEQ ID NO:3). "FAM" is a 6-carboxy fluorescein whereas "Q" is BHQ1 quencher (Glen Research). The specialty sequences were coupled to the 5'-end of the common primer template sequence through a long and flexible polyethylene glycol C18 linker (Glen Research). A synthetic 96-mer oligonucleotide (SEQ ID NO:1) was used as a target nucleic acid. The sequence of the primers or their binding sites is underlined within the target sequence.

FIG. 14 B shows curves of fluorescence monitoring during the PCR cycles. The curves of every specialty primer tested in PCR are identified by a length of the specialty sequence.

FIG. 14C is a logarithmic representation of the same data shown in FIG. 14B. This is particularly useful in determining of the threshold values (Ct) for real time curves which are identified herein as interception points between the curves and axis X (PCR cycles). Appropriate stock solutions of the reaction components were mixed to provide the following concentrations in PCR (25 µl): forward (Primer #1) (SEQ ID NO:2) and one of the reverse specialty Primers #2-6—200 nM each; target oligonucleotide—10,000 copies per reaction; dNTPs—200 µM each; JumpStart DNA polymerase (Sigma)—0.04 U/µl in 50 mM KCl, 2 mM MgCl2, 20 mM Tris-HCl (pH 8.0). PCR was performed on SmartCycler (Cepheid Corporation) using a time/temperature profile (95°2')→(95°10"→60°45")$_{55}$. The reaction fluorescence was measured at the annealing/extension cycle stage (60°45") and plotted versus PCR cycles providing real time curves shown in FIG. 14B. Background fluorescence was subtracted using the instrument software.

The following oligonucleotide components were used in this set of reactions.

1) A synthetic 96-mer oligodeoxynucleotide (Sigma Genosys) was used as a target nucleic acid:

```
                                     (SEQ ID NO: 1)
'-CGGGCATTCCTGAAGCTGACAGCATTCGGGCCGAGATGTCTCGCTCCG
TGGCCTTAGCTGTGCTCGGGCTACTCTCTCTTTCTGGCCTGGAGGCT
A-3'
```

2) Forward oligodeoxynucleotide Primer #1:
```
                                     (SEQ ID NO: 2)
5'-GCATTCCTGAAGCTGACAGCA-3'
```

3) Reverse oligodeoxynucleotide primers:
Primer #2 (19-mer):
```
                                     (SEQ ID NO: 3)
5'-(FAM)TGTCTCGCTCCGTGGCCTT(Q)(C18)CTCCAGGCCAGAAAG
AGAGAGTAG-3'
```

Primer #3 (15-mer):
```
                                     (SEQ ID NO: 4)
5'-(FAM)tctcgctCcgtggcc(Q)(C18)ctccaggccagaaagagag
agtag-3'
```

Primer #4 (13-mer):
```
                                     (SEQ ID NO: 5)
5'-(FAM)CTCGCTCCGTGGC(Q)(C18)CTCCAGGCCAGAAAGAGAGAG
TAG-3'
```

Primer #5 (11-mer):
```
                                     (SEQ ID NO: 6)
5'-(FAM)TCGCTCCGTGG(Q)(C18)CTCCAGGCCAGAAAGAGAGAGTA
G-3
```

Primer #6 (9-mer):
```
                                     (SEQ ID NO: 7)
5'-(FAM)CGCTCCGTG(Q)(C18)CTCCAGGCCAGAAAGAGAGAGTA
G-3'
```

Primers #2-6 incorporate identical primer template sequence (underlined) and differ by the specialty sequences which are identified here and in FIG. 14 by the length (9, 11, 13, 15 and 19-mers).

The above shown oligonucleotide primers and oligonucleotide components used in other Examples of the invention were prepared according to standard procedures and laboratory techniques as described below.

Synthesis of oligonucleotide components. FAM is 6-carboxy fluorescein incorporated using 1-Dimethoxytrityloxy-2-(6-carboxy-(di-O-pivaloyl-fluorescein)-4-aminobutyl)-propyl-3-O-(2-cyanoethyl)-(N,N-diisopropyl)-phosphoramidite (Glen Research). Q is BHQ-1 quencher incorporated using a BHQ-1 DMT Amidite (Biosearch Technologies) and C18 is a hexaethyleneglycol linker incorporated using a 18-O-Dimethoxytrityl hexaethyleneglycol, 1-[(2-cyanoethyl)-(N,N-diisopropyl)]-phosphoramidite (Glen Research). Oligonucleotides were synthesized either on ABI394 DNA synthesizer (Applied Biosystems) or MerMaid 6 DNA synthesizer (BioAutomation Corporation) using protocols recommended by the manufacturers for 0.2 or 1 µmole synthesis scales. Standard phosphoramidites, solid supports and reagents to perform the solid support oligonucleotide synthesis were purchased from Glen Research.

5-Ethylthio-1H-tetrazile solution (0.25 M) was used as a coupling agent. After the automated synthesis, oligonucleotides were deprotected in aqueous 30% ammonia solution by incubation for 2 days at room temperature, 12 hours at 55° C. or 2 hours at 70° C.

Purification of oligonucleotide components. Tri-ON oligonucleotides were purified by HPLC on a reverse phase C18 column (LUNA 5 μm, 100A, 250×4.6 mm, Phenomenex Inc) using gradient of acetonitryl in 0.1 M triethyl ammonium acetate (pH 8.0) or carbonate (pH 8.5) buffer with flow rate of 1 ml/min. A gradient profile including washing stage 0→14% (10"), 14→45% (23'), 45→90% (10"), 90→90% (5'50"), 90→0% (30"), 0→0% (7'30") was be applied for purification of all Tri-ON oligonucleotides. The product containing fractions was dried down in vacuum (SPD 1010 SpeedVac system, TermoSavant) and trityl groups were removed by treatment in 80% aqueous acetic acid at room temperature for 40-60 minutes. After addition to the detritylation reaction (100 μl) of 20 μl sodium acetate (3 M), the oligonucleotide components were precipitated in alcohol (1.5 ml), centrifuged, washed with alcohol and dried down. Concentration of the oligonucleotide components was determined based on the optical density at 260 nm and the extinction coefficients calculated for individual oligonucleotides using on-line Oligo-Analyzer 3.0 software provided by Integrated DNA Technologies. Based on the measurements, convenient stock solutions in water were prepared and stored at −20° C. for further use.

Oligonucleotide quality control. Purity of all prepared oligonucleotide components was confirmed by analytical 8-20% PAAG electrophoresis, reverse phase HPLC and by spectroscopy on Cary 4000 UV-VIS spectrophotometer equipped with Cary WinUV software, Bio Package 3.0 (Varian, Inc.).

Oligonucleotide primer designs and Tm measurements. Market software Beacon Designer 3 (PREMIER Biosoft International) was used to design all oligonucleotide primers, probes and other oligonucleotide components. The same software provides duplex melting temperatures ($T_m$). $T_m$ calculations were also performed in accordance with protocols described in Puglisi J. D. and Tinoco I., Jr. (1989) *Methods Enzymol.*, 180: 304-325; Sugimoto N. et al (1996) *Nucleic Acids Res.*, 24: 4501-4505.

Preparation of PCR Reactions. Appropriate Stock Solutions of the Reaction Components were mixed to provide the following concentrations in PCR (25 μl): forward (Primer #1) and one of the reverse specialty Primers #2-6—200 nM each; target oligonucleotide—10,000 copies per reaction; dNTPs—200 μM each; JumpStart DNA polymerase (Sigma)—0.04 U/μl in 50 mM KCl, 2 mM $MgCl_2$, 20 mM Tris-HCl (pH 8.0). PCR was performed on SmartCycler (Cepheid Corporation) using a time/temperature profile (95°2')→(95°10"→60°45")$_{55}$.

The reaction fluorescence was measured at the annealing/extension cycle stage (60°45") and plotted versus PCR cycles providing real time curves shown in FIG. 14B. Background fluorescence was subtracted using the instrument software. FIG. 14C is a logarithmic representation of the same data shown in FIG. 14B. A certain point near the rise of fluorescence versus PCR cycles is called a threshold value. The threshold value (CO is a characteristic which is commonly used in the Art to describe the performance of real time PCR (usually quantitative PRC). The threshold value is mainly determined by two factors, initial concentration of a target nucleic acid in a sample and yield of the primer extension reaction at PCR cycles. There are many ways in the Art to define $C_t$. The threshold points are identified herein as interception points between the logarithmic curves of the fluorescence and axis X (PCR cycles). Each of the shown curves is an average of four independent reactions.

Example 1 represents a set of the real time PCR experiments to detect the target 96-mer oligonucleotide using a method of the invention which is schematically shown in FIG. 5.

FIG. 5 shows an example of one method embodiment of the invention wherein a 5'-nuclease cleavage structure is created during an oligonucleotide primer extension and detection is based on use of FRET effect. A forward PCR primer incorporates a 5'-specialty sequence carrying a reporting fluorescent dye "F" conjugated to the 5'-end and a quencher "Q" dye conjugated to the 3'-end of the specialty sequence. The 3'-end of the specialty sequence is coupled to the 5'-end of a primer template sequence through a none-extendable linker "X" (circled). The "template sequence" of a specialty oligonucleotide primer hybridizes to a sense strand of a target DNA (stage A) wherein it is recognized by a DNA polymerase and extended (stage B) resulting in DNA duplex. The specialty sequence is designed to be complementary to a sequence within the extended antisense strand. After a strand denaturation stage (e.g., 95° C.), an antisense amplicon which incorporates the specialty primer folds into a secondary structure (stage C). Hybridization with a reverse oligonucleotide primer leads to extension by the DNA polymerase (stage D). During the reverse primer extension, when a 3'-end of the extension product reaches the 5'-end of the folded amplicon, the 'three-strand cleavage structure' is created and a 5'-nuclease cleaves the 5'-strand of the antisense amplicon (stage E) releasing the reporting dye "F" from FRET interaction with the quencher "Q", thus providing a detectable fluorescent signal. The DNA polymerase displaces an uncleaved part of the hybridized specialty sequence and continues the strand extension until it reaches the none-extendable linker "X." After completion of the stage E, followed by a denaturation stage, a newly synthesized sense amplicon may again hybridize with another molecule of the forward specialty primer initiating another cycle of the PCR.

When reverse Primers #2-6 are incorporated into an amplicon as result of the primer extension in PCR, the FRET-labeled 5'-specialty sequences find their complements within the amplicon and this prompts the amplicon to fold into a secondary structure providing two strands of a three-strand cleavage structure. The third strand (3'-strand) of the three-strand cleavage structure is provided during the extension of the forward primer #1 hybridized to the same amplicon as exemplified in FIG. 5. JumpStart Taq polymerase (Sigma) used in all Examples of the invention is an antibody inactivated "hot start" DNA polymerase designed to minimize non-specific amplification while increasing target yield. The Taq polymerase express 5'-nuclease activity and it recognize the three-strand structure and it cleaves the FRET-labeled specialty sequence nearby the 5'-end releasing a fluorescein dye from the FRET interaction with a "dark" (none-fluorescent) quencher and providing a fluorescent signal as it can be seen for all tested Primers #2-6 in FIG. 14B. The best signal performance was observed for a reverse primer #4 (13-mer). Fewer signals were produced by longer specialty sequences (Primers #2 and 3, 19-mer and 15-mer respectively). This does not necessarily indicate the difference in the cleavage reaction efficiency. The shorter specialty sequence in primer #4 has better FRET quenching compare to the 15- and 19-mers in primers #2 and 3 and the background was subtracted. In respective TaqMan™ assays (when the FRET-labeled specialty sequences are not covalently linked to the 5'-end of the primer template sequence), FRET probes shorter than 13-mer are not cleaved providing no fluorescence signal. In the set of experiments shown here, even the shortest 9-mer specialty sequence was cleaved resulting in a real time curve. Without being bound by any particular theory the remarkably good performance of the reverse specialty primers #4 and 5 in the real time assays is likely because of two factors. First, stability of a DNA duplex formed by a secondary structure (intramolecular reaction) is elevated compare to the same duplex formed by separate sequences (intermolecular reaction). Second, there is always a possibility in a TaqMan™ assay when a probe does not find its complement within the target before the primer extension passes over this binding site. In such a case, the extension does not result in cleavage. The secondary structure formation of the invention is an intramolecular reaction and it is significantly faster than in many other conventional assays like TaqMan™. The general concern discussed herein about a negative effect on PCR of the amplicon having secondary structure elements is valid in this invention. For example, the data in FIG. 14C indicates ~3-4 cycle delay in $C_t$ values for primers #2 and 3 whereas the respective values for the primers #4 and 5 are in an anticipated range of ~26-27 cycles. The amplicon secondary structures formed in case of 19-mer and 15-mer specialty sequences are likely too stable, blocking Taq polymerase to a certain degree and reducing the yield the primer extension. This may be corrected, if desired, by extending time of the annealing/extension stage (e.g. to 60 seconds). Those of ordinary skill in the art will appreciate that the polymerase blockage effect observed herein for the Primers #2 and 3 may be eliminated by increasing the annealing/extension temperature from 60° C. (used in this set of the experiments) to, for example, 70 or 75° C. However, this would require respectively a redesign of the template oligonucleotide sequences to have elevated Tm values to address adequately the increase in the stringency of PCR. The $C_t$ delay in case of the primer #6 (9-mer) is likely caused by a relative drop in the signal performance and low stability of the amplicon secondary structure. The successful performance of the primer #4 (13-mer) in real time assay as judged by both characteristics, the signal and threshold value, proves that an optimal design of a specialty oligonucleotide primer can be always found for practicing this particular method of the invention.

Example 2

Figure 15:
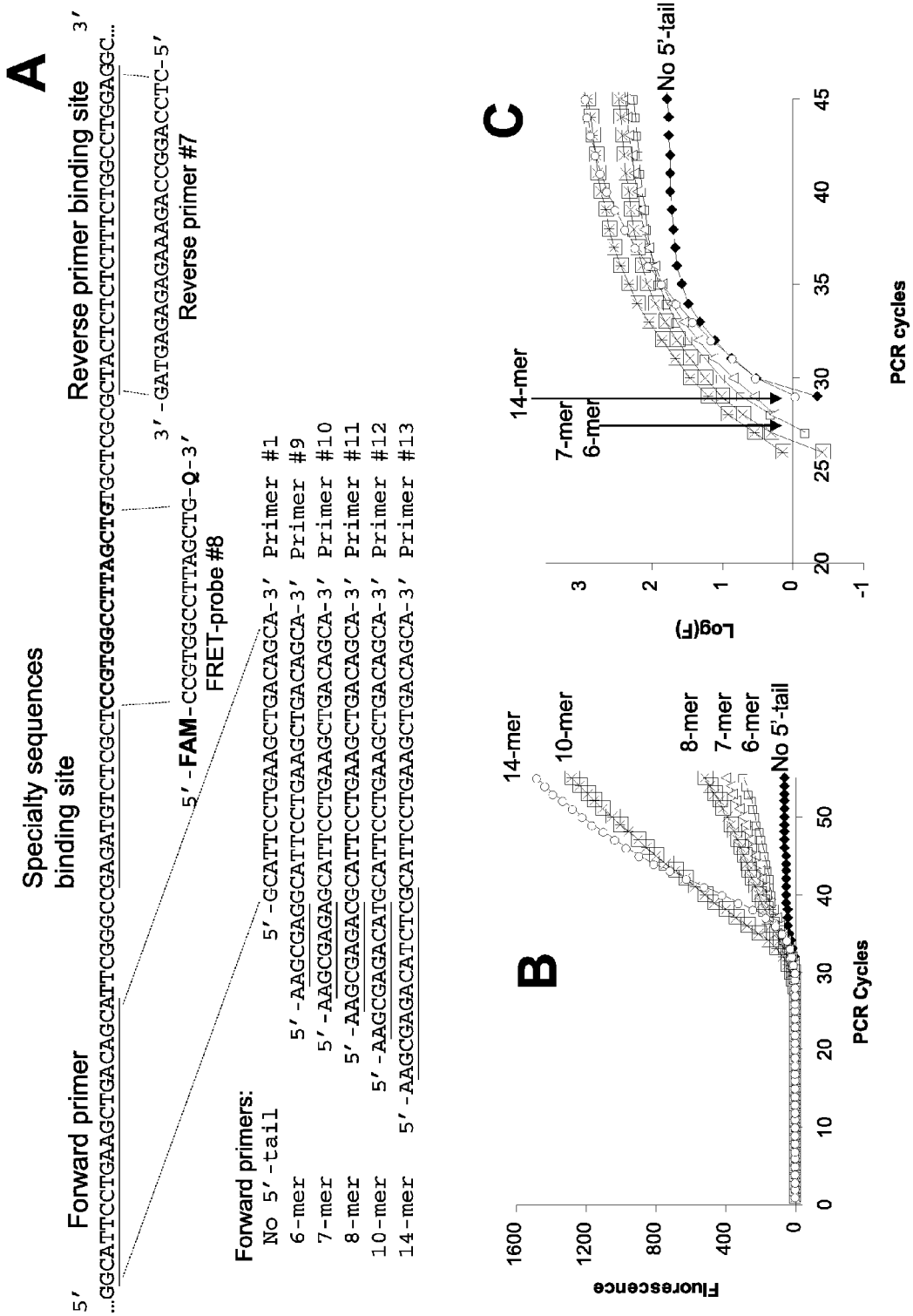
FIG. 15 shows experimental data from performing real time FRET assays according to a method of the invention described in FIG. 7.

The design of oligonucleotide components, forward and reverse primers, including specialty primers and a FRET-probe used in Example 2 and results of the real time experiments, are shown in FIG. 15.

FIG. 15 shows experimental data from performing real time FRET assays according to a method of the invention described in FIG. 7.

FIG. 15A shows the design of oligonucleotide components used in the assays. Forward primers #9-13 incorporated 5'-specialty sequences of a variable length. The oligonucleotide primer #1 (SEQ ID NO:2) is a conventional PCR primer (no 5'-specialty tail). Use of the forward primers #9-13 in combination with the reverse primer #7 (SEQ ID NO:3) in PCR leads to formation of amplicons which fold into secondary structures as shown in FIG. 7. The 5'-specialty tail sequences of the primers #9-13 were designed to provide respectively 6, 7, 8, 10 and 14-mer secondary structure duplexes, which collectively with a FRET-probe #8 (SEQ ID NO:13) form optimal cleavage structures for 5'-nuclease. The specialty sequences which participate in these duplex formations are underlined in the primers #9-13 (SEQ ID NOS:8-12). The 5'-terminal adenosine is not complementary to the target DNA providing a single nucleotide flap as shown in FIG. 7. "FAM" is a 6-carboxy fluorescein whereas "Q" is BHQ1 quencher (Glen Research). A synthetic 96-mer oligonucleotide (SEQ ID NO:1) was used as a target nucleic acid. The sequences of the primers or their binding sites as well as a binding site of the specialty sequences are underlined within the target sequence. The FRET-probe sequence is shown in bold font. Every forward primer shown in this Figure was individually tested in a real time PCR assay in a reaction mixture with the FRET-probe #8 (SEQ ID NO:13) and the reverse primer #7 (SEQ ID NO:3).

FIG. 15B shows the results of the fluorescence monitoring in the reactions of FIG. 15A. The curves are identified by a length of the specialty sequence fragment (underlined in primers #9-13) (SEQ ID NOS:8-12) which participates in the duplex formation (folded amplicons). Combination of the primers #1 (SEQ ID NO:2) and 7 (SEQ ID NO:3) with the FRET-probe #8 (SEQ ID NO:13) (No 5'-tail) represents a conventional (TaqMan) assay design.

FIG. 15C is a logarithmic representation of the same data shown in FIG. 15B provided here to determine the threshold values (Ct) as described in the context of FIG. 14. Appropriate stock solutions of the reaction components were mixed to provide the following concentrations in PCR (25 µl): one of the forward (primers #1 (SEQ ID NO:2) or 9-13 (SEQ ID NO:8-12)) and the reverse primer #7 (SEQ ID NO:3)—100 nM each; FRET-probe #8 (SEQ ID NO:13)—400 nM; target oligonucleotide—10,000 copies per reaction; dNTPs—200 µM each; JumpStart DNA polymerase (Sigma)—0.04 U/µl in 50 mM KCl, 2 mM MgCl2, 20 mM Tris-HCl (pH 8.0). PCR was performed on SmartCycler (Cepheid Corporation) using a time/temperature profile $(95°2')\rightarrow(95°10''\rightarrow64°45'')_{55}$. The reaction fluorescence was measured at the annealing/extension cycle stage (64°45'') and plotted versus PCR cycles providing real time curves shown in FIG. 15B. Background fluorescence was subtracted using the instrument software.

Sequence of the target DNA 96-mer used in these experiments is shown in Example 1.

The following oligonucleotide components were used in this set of reactions.

```
Forward primers:
Primer #1 (No 5'-tail):
                                     (SEQ ID NO: 2)
5'-GCATTCCTGAAGCTGACAGCA-3'

Primer #9 (6-mer):
                                     (SEQ ID NO: 8)
5'-AAGCGAGGCATTCCTGAAGCTGACAGCA-3'

Primer #10 (7-mer):
                                     (SEQ ID NO: 9)
5'-AAGCGAGAGCATTCCTGAAGCTGACAGCA-3'

Primer #11 (8-mer):
                                     (SEQ ID NO: 10)
5'-AAGCGAGACGCATTCCTGAAGCTGACAGCA-3'

Primer #12 (10-mer):
                                     (SEQ ID NO: 11)
5'-AAGCGAGACATGCATTCCTGAAGCTGACAGCA-3'

Primer #13 (14-mer):
                                     (SEQ ID NO: 12)
5'-AAGCGAGACATCTCGCATTCCTGAAGCTGACAGCA-3'

FRET probe #8:
                                     (SEQ ID NO: 13)
5'-FAM-CCGTGGCCTTAGCTG-Q-3'
```

-continued

Reverse Primer #7:
(SEQ ID NO: 3)
5'-CTCCAGGCCAGAAAGAGAGAGTAG-3'

Synthesis, purification and quality control of the shown oligonucleotide components were performed in accordance with protocols described in Example 1. FAM is 6-carboxy fluorescein incorporated using 1-Dimethoxytrityloxy-2-(6-carboxy-(di-O-pivaloyl-fluorescein)-4-aminobutyl)-propyl-3-O-(2-cyanoethyl)-(N,N-diisopropyl)-phosphoramidite (Glen Research). Q is BHQ-1 quencher incorporated using a BHQ-1 conjugated CPG (controlled pore glass) from Biosearch Technologies.

Preparation of PCR Reactions. Appropriate Stock Solutions of the Reaction Components were mixed to provide the following concentrations in PCR (25 µl): one of the forward (primers #1 or 9-13) and the reverse primer #7—100 nM each; FRET-probe #8—400 nM; target oligonucleotide—10,000 copies per reaction; dNTPs—200 µM each; JumpStart DNA polymerase (Sigma)—0.04 U/µl in 50 mM KCl, 2 mM MgCl$_2$, 20 mM Tris-HCl (pH 8.0).

PCR was performed on SmartCycler (Cepheid Corporation) using a time/temperature profile (95°2')→(95°10"→64°45")$_{55}$. The reaction fluorescence was measured at the annealing/extension cycle stage (64°45") and plotted versus PCR cycles providing real time curves shown in FIG. 15B. FIG. 15C is a logarithmic representation of the same data shown in FIG. 15B plotted here to determine the respective threshold values ($C_t$). Background fluorescence was subtracted using the instrument software. Each of the shown curves is an average of four independent reactions.

Every forward primer used in this Example (also shown in FIG. 15A) was individually tested in a real time PCR assay in a reaction mixture with the FRET-probe #8 and the reverse primer #7. The results of the fluorescence monitoring in these reactions are provided in FIG. 15B. The curves are identified by a length of the specialty sequence fragment (underlined in primers #9-13) which participates in the duplex formation (folded amplicons). Combination of the primers #1 and 7 with the FRET-probe #8 (No 5'-tail) represents a conventional TaqMan assay design. Use of the oligonucleotide specialty primers #9-13 represents a method of the invention described in FIG. 7. Forward primers #9-13 incorporated 5'-specialty sequences of a variable length. The oligonucleotide primer #1 is a conventional PCR primer (no 5'-specialty tail). Use of the forward primers #9-13 in combination with the reverse primer #7 in PCR leads to formation of amplicons which fold into secondary structures as shown in FIG. 7. The 5'-specialty tail sequences of the primers #9-13 were design to provide respectively 6, 7, 8, 10 and 14-mer secondary structure duplexes which collectively with a FRET-probe #8 form optimal cleavage structures for 5'-nuclease. The 5'-terminal adenosine is not complementary to the target DNA providing a single nucleotide flap as shown in FIG. 7.

As it can be seen in FIG. 15B, the TaqMan assay employing the 15-mer FRET probe #8 showed almost no signal during the real time PCR at 64° C. of annealing/extension temperature. The probe is obviously forming a very unstable duplex with the target amplicon. However, appearance of secondary structures in PCR amplicons provided by the use of the specialty primers #9-13 greatly accelerates the cleavage of the same probe. The signal strength grows with the increase in length of the specialty sequence (and thus the stability of the secondary structures) in a row 6-mer<7-mer<8-mer<10-mer<14-mer. Such a result was totally unexpected by all accepted rules in oligonucleotide-based detection assays. The 15-mer FRET-probe has very weak hybridization properties having Tm value of ~57-58° C. This is 6-7° C. lower than the annealing/extension temperature (64° C.) used herein.

Without being bound to any particular theory, we speculate that the 5'-nuclease domain of Taq polymerase binds tightly to the optimal three-strand cleavage formed in particular in the reactions of the primer #12 and 13 "stabilizing" to a certain degree the duplexes of the cleavage structure. The inefficiency in the probe hybridization may be compensated or even overcompensated, as has been observed herein, by the very efficient cleavage process. The probe #8 was taken in a 4-fold excess (400 nM) over the primers concentration (100 nM) providing a condition for the cleavage cycling mode when more than one probe can be cleaved in the assay per one target nucleic acid molecule. Unlike the TaqMan assay and the method of the invention described in Example 1, the detection reaction of this Example is not "directly bound" to the primer extension during PCR. The probe cleavage may continue even when PCR amplification slows dawn or stops due to consumption of all oligonucleotide primers. If any negative effect of the amplicon secondary structures on PCR takes place in this set of experiments, it may explain a slight delay in $C_t$ value of ~28-29 observed for the forward primer #13 (14-mer). The best performer in this study was primer #12 providing excellent signal and a threshold vale of 26.

Example 3

Figure 16:
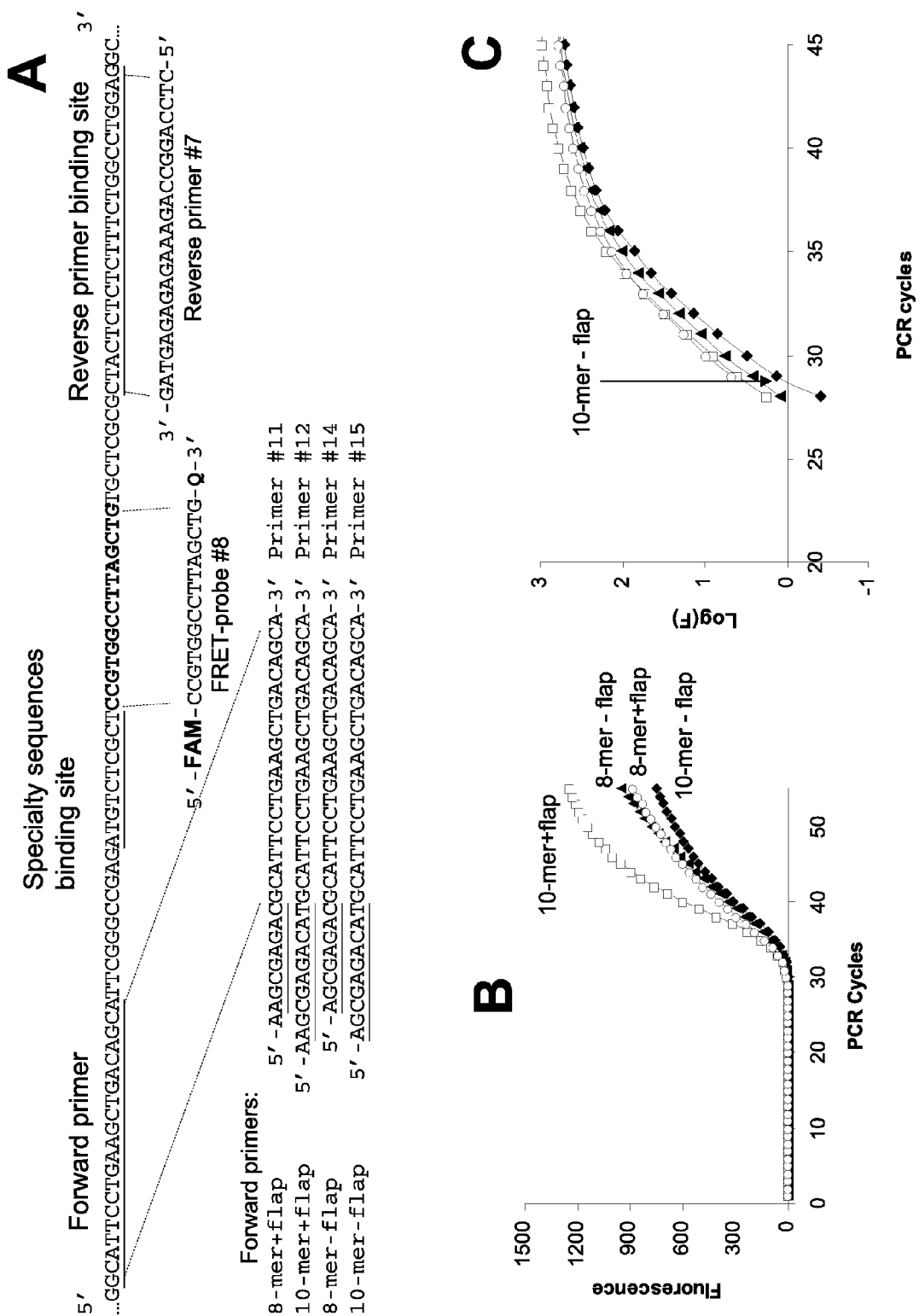
FIGS. 16A-C show results of real time assays, similar to those shown in FIG. 15 and performed to compare specialty oligonucleotide primers with and without a single nucleotide 5'-flap.

The design of oligonucleotide components including specialty primers and a FRET-probe and the results of these oligonucleotide components use in real time experiments are shown in FIG. 16.

FIG. 16A shows the design of oligonucleotide components used in these experiments. The specialty sequences which participate in the amplicon secondary structure formation are underlined in primers #11, 12, 14 and 15 (SEQ ID NOS:14-17). The forward primers #14 and 15 (SEQ ID NOS:16, 17) are different from the primers #11 and 12 (SEQ ID NOS:14, 15). respectively by absence of a 5'-terminal adenosine. Primers #11 and 12 were designed to provide amplicons folding into secondary structures with a 3'-single nucleotide flap as shown in FIG. 7. These amplicons hybridized to a FRET-probe #8 (SEQ ID NO:13) to form optimal three-strand structures for cleavage by 5'-nuclease. Use of the oligonucleotide primers #14 and 15 provides the amplicon secondary structures with no flaps as shown in FIG. 12. Formation of suboptimal structures, e.g. structure B in FIG. 1, was anticipated for these 5'-specialty primers #14, 15. The forward primers were individually studied in PCR in a reaction mixture with the FRET-probe #8 (SEQ ID NO:13) and the reverse primer #7 (SEQ ID NO:3).

FIG. 16B shows the results of the fluorescence monitoring in the reactions of 16A. The curves are identified by a length of the specialty sequence fragment (8-mer or 10-mer) which participates in the duplex formation of the folded amplicons (underlined) and presence (+flap) or absence (–flap) of a single base flap.

FIG. 16C is a logarithmic representation of the same data shown in FIG. 16B provided here to determine the threshold values (Ct) as described in the FIG. 14 legend. Appropriate stock solutions of the reaction components were mixed to provide the following concentrations in PCR (25 µl): a forward primer (#11, 12, 14 or 15) and the reverse primer #7—100 nM each; FRET-probe #8—200 nM; target oligonucleotide—10,000 copies per reaction; dNTPs—200 µM each; JumpStart DNA polymerase (Sigma)—0.04 U/µl in 50 mM KCl, 2 mM MgCl2, 20 mM Tris-HCl (pH 8.0). PCR was performed on SmartCycler (Cepheid Corporation) using a time/temperature profile (95°2')→(95°10"→60°45")₅₅. The reaction fluorescence was measured at the annealing/extension cycle stage (60°45") and plotted versus PCR cycles providing real time curves shown in FIG. 16B. Background fluorescence was subtracted using the instrument software.

Sequence of the target DNA 96-mer used in these experiments is shown in Example 1. The following oligonucleotide components were used in experiments of this Example.

```
Forward primers:
Primer #11 (8-mer + flap):
                                      (SEQ ID NO: 14)
5'-AAGCGAGACGCATTCCTGAAGCTGACAGCA-3'

Primer #12 (10-mer + flap):
                                      (SEQ ID NO: 15)
5'-AAGCGAGACATGCATTCCTGAAGCTGACAGCA-3'

Primer #14 (8-mer-flap):
                                      (SEQ ID NO: 16)
5'-AGCGAGACGCATTCCTGAAGCTGACAGCA-3'

Primer #15 (10-mer-flap):
                                      (SEQ ID NO: 17)
5'-AGCGAGACATGCATTCCTGAAGCTGACAGCA-3'

FRET probe #8:
                                      (SEQ ID NO: 13)
5'-FAM-CCGTGGCCTTAGCTG-Q-3'

Reverse Primer #7:
                                      (SEQ ID NO: 3)
5'-CTCCAGGCCAGAAAGAGAGAGTAG-3'
```

Synthesis, purification and quality control of the shown oligonucleotide components were performed in accordance with protocols described in Example 1. FAM is 6-carboxy fluorescein incorporated using 1-Dimethoxytrityloxy-2-(6-carboxy-(di-O-pivaloyl-fluorescein)-4-aminobutyl)-propyl-3-O-(2-cyanoethyl)-(N,N-diisopropyl)-phosphoramidite (Glen Research). Q is BHQ-1 quencher incorporated using a BHQ-1 conjugated CPG (controlled pore glass) from Biosearch Technologies.

Preparation of PCR Reactions. Appropriate Stock Solutions of the Reaction Components were mixed to provide the following concentrations in PCR (25 μl): a forward primer (#11, 12, 14 or 15) and the reverse primer #7—100 nM each; FRET-probe #8—200 nM; target oligonucleotide—10,000 copies per reaction; dNTPs—200 μM each; JumpStart DNA polymerase (Sigma)—0.04 U/μl in 50 mM KCl, 2 mM MgCl₂, 20 mM Tris-HCl (pH 8.0). PCR was performed on SmartCycler (Cepheid Corporation) using a time/temperature profile (95°2') →(95°10"→60°45")₅₅. The reaction fluorescence was measured at the annealing/extension cycle stage (60°45") and plotted versus PCR cycles providing real time curves shown in FIG. 16B. Background fluorescence was subtracted using the instrument software. FIG. 16C is a logarithmic representation of the same data shown in FIG. 16B provided here to determine the threshold values ($C_t$) as described in the FIG. 14 legend and Example 1.

This study was performed to compare specialty oligonucleotide primers with and without a single nucleotide 5'-flap in conducting a method of the invention shown in FIG. 7. FIG. 16A shows design of oligonucleotide components used in these experiments. The specialty sequences which participate in the amplicon secondary structure formation are underlined in primers #11, 12, 14 and 15. The forward primers #14 and 15 are different from the primers #11 and 12 respectively by absence of a 5'-terminal adenosine (flap). Primers #11 and 12 were designed to provide amplicons folding into secondary structures with a 3'-single nucleotide flap as shown in FIG. 7. These amplicons hybridizing to a FRET-probe #8 form optimal three-strand structures for cleavage by 5'-nuclease. Use of the oligonucleotide primers #14 and 15 provides the amplicon secondary structures with no flaps as shown in FIG. 12 and this was anticipated to result in an suboptimal three-strand cleavage structure B shown in FIG. 1. However, the results of the fluorescence monitoring in these reactions provided in FIG. 16B show little difference in the assay performance between the four studied specialty primers. The curves are identified by a length of the specialty sequence fragment (8-mer or 10-mer) which participates in the duplex formation of the folded amplicons (underlined in the primer sequences) and presence (+flap) or absence (-flap) of a single base flap. Presence or absence of the 3'-single nucleotide flap, formation of optimal or suboptimal cleavage structures in PCR does not appear to have any profound effect on the real time assays. A potential explanation to this unexpected result could be a special property of Taq polymerase. According to Ichihara Y. and Kurosawa Y. (1993) *Gene,* 130: 153-154, more than half of the products of PCR contain an extra A residue at the 3' end, which is the result of the template-independent activity of Taq polymerase. If this is correct, than the addition of the 3'-extra adenosine would "restore" the optimal cleavage structure in case of the primers #14 and 15 providing the 3'-flap, the compliment of which was "missing" in the original primer design. However, such an effect would lead to formation of suboptimal cleavage structures in case of the primers #11 and 12 wherein the three-strand cleavage structures would contain a two-nucleotide 3'-flap sequence. Without being bound to any particular theory, we may speculate that the reaction of the addition of one 3'-extra nucleotide by Taq polymerase is not quantitative providing a pool of amplicons forming both optimal and suboptimal cleavage structures in all cases studied in this Example. We may also speculate that the suboptimal cleavage structures are reasonably effective in "catalyzing" the FRET-probe cleavage. In any case, this experiment underscores the effective designs of specialty oligonucleotide primers to be used in this method of the invention.

Example 4

The real time PCR assays in this Example were performed according to a method of the invention described in FIG. 8. The results are shown in FIG. 17.

In these assays, forward and reverse oligonucleotide primers incorporated 5'-specialty sequences to provide PCR amplicons which fold into three-strand cleavage structures. Sequence of the target DNA 96-mer used in these experiments is shown in Example 1. Structures of the reverse FRET-labeled primers #2-6 used in these experiments are shown below and also in FIG. 14 and Example 1.

The following oligonucleotide components were used in experiments of this Example.

```
Forward specialty oligonucleotide primers:
Primer #16:
                                      (SEQ ID NO: 18)
5'-CTCTCGGCCCGCATTCCTGAAGCTGACAGCA-3'

Primer #17:
                                      (SEQ ID NO: 19)
5'-CCATCTCGGCGCATTCCTGAAGCTGACAGCA-3'
```

-continued

Primer #18:
(SEQ ID NO: 20)
5'-CACATCTCGGCGCATTCCTGAAGCTGACAGCA-3'

Primer #19:
(SEQ ID NO: 21)
5'-CGACATCTCGGGCATTCCTGAAGCTGACAGCA-3'

Primer #20:
(SEQ ID NO: 22)
5'-CAGACATCTCGGGCATTCCTGAAGCTGACAGCA-3'

Reverse FRET-labeled specialty oligodeoxynucleo-
tide primers:
Primer #2 (19-mer):
(SEQ ID NO: 3)
5'-(FAM)TGTCTCGCTCCGTGGCCTT(Q)(C18)CTCCAGGCCAGAAAG
AGAGAGTAG-3'

Primer #3 (15-mer):
(SEQ ID NO: 4)
5'(FAM)tctcgctCcgtggcc(Q)(C18)ctccaggccagaaagagaga
gtag-3'

Primer #4 (13-mer):
(SEQ ID NO: 5)
5'-(FAM)CTCGCTCCGTGGC(Q)(C18)CTCCAGGCCAGAAAGAGAGAG
TAG-3'

Primer #5 (11-mer):
(SEQ ID NO: 6)
5'-(FAM)TCGCTCCGTGG(Q)(C18)CTCCAGGCCAGAAAGAGAGAGTA
G-3'

Primer #6 (9-mer):
(SEQ ID NO: 7)
5'-(FAM)CGCTCCGTG(Q)(C18)CTCCAGGCCAGAAAGAGAGAGTA
G-3'

Synthesis, purification and quality control of the shown oligonucleotide components were performed in accordance with protocols described in Example 1.

Preparation of PCR Reactions. Appropriate Stock Solutions of the Reaction Components were mixed to provide the following concentrations in PCR (25 µl): a forward primer (one of primers #16-20) and a reverse primer (one of primers #2-6)—200 nM each; target oligonucleotide—10,000 copies per reaction; dNTPs—200 µM each; JumpStart DNA polymerase (Sigma)—0.04 U/µl in 50 mM KCl, 2 mM $MgCl_2$, 20 mM Tris-HCl (pH 8.0). PCR was performed on SmartCycler (Cepheid Corporation) using a time/temperature profile (95°2') →(95°10"→60°45")$_{55}$.

The reaction fluorescence was measured at the annealing/extension cycle stage (60°45") and plotted versus PCR cycles providing real time curves shown in FIG. 17A. Background fluorescence was subtracted using the instrument software. FIG. 17B is a logarithmic representation of the same data shown in FIG. 17A provided here to determine the threshold values ($C_t$) as described in the FIG. 14 legend and Example 1. The underlined sequences in primers #16-20 are specialty sequences that participate in amplicon secondary structure formation. 5'-Terminal cytosine is not complementary to the target DNA. The fluorescent curves shown in FIG. 17A correspond to the following combinations of primers:

| | |
|---|---|
| 19-mer: | Primers #2 + 16 |
| 15-mer: | Primers #3 + 17 |
| 13-mer: | Primers #4 + 18 |
| 11-mer: | Primers #5 + 19 |
| 9-mer: | Primers #6 + 20 |

All these primer combination were designed to synthesize PCR amplicons which fold into secondary structures as shown in FIG. 8 providing an optimal three-strand cleavage structure for 5'-nuclease (Structure D, FIG. 1).

For the instant Example, the 13-mer combination (Primers #4+18) showed the best performance in the real time assays, similar to the results discussed in Example 1. However, the performance difference in the studied herein combinations is not as profound as this was observed in the method of Example 1. The most remarkable is the comparative increase in signal performance for the shortest FRET-labeled specialty sequences, 9-mer and 11-mer combinations. Analysis of the results of these two Examples 1 and 4 also indicates the increase in $C_t$ values of ~4 cycles for all primer combinations studied. This effect is most likely attributable to the structural complexity of the PCR amplicons in the method of FIG. 8 which form not one but two steam-loop secondary structures.

Example 5

A study conducted in this Example was aiming to investigate a preference in specialty oligonucleotide primer design according to the method of the invention described in FIG. 8.

FIG. 8 shows yet another method embodiment, wherein formation of a three-strand cleavage structure does not require use of an oligonucleotide cleavage component (e.g., cleavage enhancer) and wherein all three strands of the cleavage structure are provided by a PCR amplicon. The method is based on use of two oligonucleotide primers, both of which incorporate 5'-specialty sequences. Hybridization of these primers with the respective strands of target nucleic acids and their extension by DNA polymerase in consequent stages A-D leads to an amplicon (sense strand) which folds into a secondary structure shown in stage E. This secondary structure represents an optimal cleavage structure for a 5'-nuclease which provides the cleavage of the 5'-strand disrupting the FRET. This method is a combination of the approaches shown in FIGS. 6 and 7. In this particular case, the FRET primer does not incorporate a non-extendable linker and its 5'-specialty sequence is designed to provide a single nucleotide 5'-flap (stage E). Such a design is preferred because of the potential problem described in the context of FIG. 12.

FIG. 17 shown results of real time fluorescence assays that were performed according to a method of the invention described in the context of FIG. 8. In these assays, forward and reverse oligonucleotide primers incorporated 5'-specialty sequences to provide PCR amplicons which fold into three-strand cleavage structures. Structures of the reverse FRET-labeled primers #2-6 used in these experiments are shown in FIG. 14. Sequences of the forward oligonucleotide primers are shown below:

(SEQ ID NO: 18)
5'-CTCTCGGCCCGCATTCCTGAAGCTGACAGCA-3'   Primer #16

(SEQ ID NO: 19)
5'-CCATCTCGGCGCATTCCTGAAGCTGACAGCA-3'   Primer #17

(SEQ ID NO: 20)
5'-CACATCTCGGCGCATTCCTGAAGCTGACAGCA-3'   Primer #18

(SEQ ID NO: 21)
5'-CGACATCTCGGGCATTCCTGAAGCTGACAGCA-3'   Primer #19

(SEQ ID NO: 22)
5'-CAGACATCTCGGGCATTCCTGAAGCTGACAGCA-3'   Primer #20

The underlined sequences in primers #16-20 are specialty sequences that participate in amplicon secondary structure formation. 5'-Terminal cytosine is not complementary to the target DNA. The fluorescent curves shown in FIG. 17A correspond to the following combinations of primers:

| 19-mer: | Primers #2 + 16 |
|---|---|
| 15-mer: | Primers #3 + 17 |
| 13-mer: | Primers #4 + 18 |
| 11-mer: | Primers #5 + 19 |
| 9-mer: | Primers #6 + 20 |

Appropriate stock solutions of the reaction components were mixed to provide the following concentrations in PCR (25 µl): a forward primer (primers #16-20) and a reverse primer (primers #2-6)—200 nM each; target oligonucleotide—10,000 copies per reaction; dNTPs—200 µM each; JumpStart DNA polymerase (Sigma)—0.04 U/µl in 50 mM KCl, 2 mM MgCl2, 20 mM Tris-HCl (pH 8.0). PCR was performed on SmartCycler (Cepheid Corporation) using a time/temperature profile $(95°2')\rightarrow(95°10''\rightarrow60°45'')_{55}$. The reaction fluorescence was measured at the annealing/extension cycle stage (60°45") and plotted versus PCR cycles providing real time curves shown in FIG. 17A. Background fluorescence was subtracted using the instrument software.

FIG. 17B is a logarithmic representation of the same data shown in FIG. 17A provided here to determine the threshold values (Ct) as described in the FIG. 14 legend.

For the instant Example, A FRET-labeled reverse primer #6 (9-mer, structure is shown in FIG. 14) was tested in real time assays individually with forward primers #16-20 (sequences are shown in the figure legend, FIG. 17 and also in Example 4). Combining the primers #6 and #20 in PCR leads to an amplicon which folds into a three-strand structure (curve "Gap –0" in FIG. 18) which is an optimal cleavage structure for 5'-nuclease (structure D, FIG. 1) whereas the combinations with other primers #16, 17, 18 and 19 provide amplicons with suboptimal cleavage structures having respectively 5, 3, 2 and 1 nucleotide gap in the target strand between the secondary structure duplexes. The results are shown in FIG. 18 and the fluorescence curves for these combinations are identified accordingly in the figure as "Gap –5," "Gap –3," "Gap –2" and "Gap –1". The PCR conditions, oligonucleotide component and reagent concentrations and time/temperature profile used were the same as described in Example 4 and in FIG. 17.

FIG. 18 shows experimental results demonstrating a preference in oligonucleotide primer design according to the method of the invention described in the context of FIG. 8. A FRET-labeled reverse primer #6 (9-mer, structure is shown in FIG. 14) was tested in real time assays individually with forward primers #16-20 (sequences given in the context of FIG. 17). Combining the primers #6 and #20 in PCR leads to an amplicon which folds into a three-strand structure (curve "Gap –0" in this FIG. 18) that is an optimal cleavage structure for 5'-nuclease (structure D, FIG. 1) whereas the combinations with other primers #16, 17, 18 and 19 provide amplicons with suboptimal cleavage structures having respectively 5, 3, 2 and 1 nucleotide gap in the target strand between the secondary structure duplexes. The fluorescence curves for these combinations are identified accordingly in the figure as "Gap –5," "Gap –3," "Gap –2" and "Gap –1". The PCR conditions, oligonucleotide component and reagent concentrations and time/temperature profile used were the same as described in Example 4 and in the context of FIG. 17.

The results of this Example emphasize the importance of the specialty oligonucleotide primer designs in practicing the method of the invention shown in FIG. 8. The primer designs which lead to formation of suboptimal cleavage structures with the target nucleotide gap performed equally deficient when compared to the optimal cleavage structure (combination of primers #6 and #20). However, the signal strength in these assays matches that obtained for the 9-mer FRET-labeled specialty sequence in experiments of FIG. 14 pointing to the mechanism of the cleavage observed.

RELEVANT REFERENCES CITED

Afonina I., Zivarts M., Kutyavin I., Lukhtanov E., Gamper H. and Meyer R. B. (1997) Efficient Priming of PCR with Short Oligonucleotides Conjugated to a Minor Groove Binder. *Nucleic Acids Res.*, 25: 2657-2660.

Afonina I. A., Reed M. W., Lusby E., Shishkina I. G. and Belousov Y. S. (2002) Minor groove binder-conjugated DNA probes for Quantitative DNA detection by hybridization-triggered fluorescence. *BioTechniques*, 32: 940-949.

Aizenstein B. D., Rasmussen E. B., Hall J. G., Agarwal P., Arco D., Atiles M. W., Burris D. E., Indig M. A., Law S. M., Mast A. L., Marshall D. J., Miller C. W., Oldenberg M. C., Prudent J. R., Schneiders J. M., Brow M. A. D., Lyamichev V. (2005) Methods and compositions for detecting target sequences. U.S. Pat. No. 6,913,881.

An L., Tang W., Ranalli T. A., Kim H.-J., Wytiaz J., and Kong H. (2005) Characterization of a Thermostable UvrD Helicase and its Participation in Helicase Dependent Amplification, *JBC*, 280: 28952-28958.

Ausubel F. M, Brent R., Kingston R. E., Moore D. D., Seidman J. G., and Struhl K., eds., (1993) *Current Protocols in Molecular Biology*, Vol. 1, Chapter 2, Section I, John Wiley & Sons, New York.

Beaucage S. L., Caruthers M. H. (1981) Deoxynucleoside phosphoramidites—A new class of key intermediates for deoxypolynucleotide synthesis, *Tetrahedron Lett.*, 22: 1859-1862.

Becker-Andre M. and Hahlbrock K. (1989) Absolute mRNA quantification using the polymerase chain reaction (PCR). A novel approach by a PCR aided transcript titration assay (PATTY). *Nucleic Acids Res.*, 17: 9437-9446.

Bedinger P., Munn M. and Alberts B. M. (1989) Sequence-specific pausing during in vitro DNA replication on double-stranded DNA templates, *J. Biol. Chem.*, 264: 16880-16886.

Belyaysky A., Vinogradova T., Rajewsky K. (1989) PCR-based cDNA library construction: general cDNA libraries at the level of a few cells. *Nucleic Acids Res.*, 17: 2919-2932.

Bierne H. and Michel B. (1994) When replication forks stop, *Mol. Microbiol.*, 13: 17-23.

Bonnet G., Tyagi S., Libchaber A. and Kramer, F. R. (1999) Thermodynamic basis of the enhanced specificity of structured DNA probes. *Proc. Natl. Acad. Sci. USA*, 96: 6171-6176.

Boom W. R., Henriette M. A., Kievits T., Lens P. F. (1993) Process for isolating nucleic acid, U.S. Pat. No. 5,234,809.

Breslauer K. J., Frank R., Blocker H., Marky L. A. (1986) Predicting DNA duplex stability from the base sequence, *Proc. Natl. Acad. Sci. USA*, 83: 3746-3750.

Brow M. A. D., Hall J. S. G., Lyamichev V., Olive D. M., Prudent J. R. (1998) Detection of nucleic acid sequences by invader-directed cleavage. U.S. Pat. No. 5,846,717.

Brow M. A. D., Hall J. S. G., Lyamichev V., Olive D. M., Prudent J. R. (1999) Detection of nucleic acid sequences by invader-directed cleavage. U.S. Pat. No. 6,001,567.

Brown E. L., Belagaje R., Ryan M. J., Khorana H. G. (1979) Chemical synthesis and cloning of a tyrosine tRNA gene, *Methods Enzymol.*, 68: 109-151.

Brownie J., Shawcross S., Theaker J., Whitcombe D., Ferrie R., Newton C. and Little S. (1997) The elimination of primer-dimer accumulation in PCR, *Nucleic Acids Res.*, 25: 3235-3241.

Burgner D., D'Amato M., Kwiatkowski D. P., Loakes D. (2004) Improved allelic differentiation using sequence-specific oligonucleotide hybridization incorporating an additional base-analogue mismatch, *Nucleosides Nucleotides Nucleic Acids*, 23: 755-765.

Cardullo R. A., Agrawal S., Flores C., Zamecnik P. C. and Wolf D. E. (1988) Nucleic acid hybridization by nonradioactive fluorescence resonance energy transfer. *Proc. Natl. Acad. Sci. USA*, 85: 8790-8794.

Caruthers M. H., Matteucci M. D. (1984) Process for preparing polynucleotides, U.S. Pat. No. 4,458,066.

Clegg R. M. (1992) Fluorescence resonance energy transfer and nucleic acids. *Methods Enzymol.*, 211: 353-388.

Clegg R. M. (1995) Fluorescence energy transfer. *Curr. Opin. Biotech.*, 6: 103-110.

Clementi M., Menzo S., Bagnarelli P., Manzin A., Valenza A., Varaldo P. E. (1993) Quantitative PCR and RT-PCR in virology. *PCR Methods Appl.* 2:191-196.

Cleuziat P. and Mandrand B. (1998) Method for amplifying nucleic acid sequences by strand displacement using DNA/RNA chimeric primers, U.S. Pat. No. 5,824,517.

Dahlberg J. E., Lyamichev V. I., Brow M. A. D. (1995) Method of site specific nucleic acid cleavage. U.S. Pat. No. 5,422,253.

Dahlberg J. E., Lyamichev V. I., Brow M. A. D. (1997) Detection of target nucleic acid molecules using synthesis-deficient thermostable DNA polymerase. U.S. Pat. No. 5,691,142.

Dahlberg J. E., Lyamichev V. I., Brow M. A. D., Oldenburg M. C. (1998) Cleavase fragment length polymorphism. U.S. Pat. No. 5,719,028.

Dahlberg J. E., Lyamichev V. I., Brow M. A. D. (1998) Detection of target nucleic acid molecules using thermostable 5' nuclease. U.S. Pat. No. 5,837,450.

Dahlberg J. E., Lyamichev V. I., Brow M. A. D., Oldenburg M. C. (1999) Rapid detection and identification of nucleic acid variants. U.S. Pat. No. 5,888,780.

Dattagupta N., Stull P. D., Spingola M., and Kacian D. L. (2001) Isothermal strand displacement nucleic acid amplification, U.S. Pat. No. 6,214,587.

Davey C. and Malek L. T. (2000) Nucleic acid amplification process, U.S. Pat. No. 6,063,603.

Didenko V. V. (2001) DNA probes using fluorescence resonance energy transfer (FRET): design and application. *BioTechniques*, 31, 1106-1121.

Di Giusto D. A. and King G. C. (2004) Strong positional preference in the interaction of LNA oligonucleotides with DNA polymerase and proofreading exonuclease activities: implications for genotyping assays. *Nucleic Acids Res.*, 32: e32.

Diviacco S., Norio P., Zentilin L., Menzo S., Clementi M., Biamonti G., Riva S., Falaschi A., Giacca M. (1992) A novel procedure for quantitative polymerase chain reaction by coamplification of competitive templates, *Gene*, 122: 313-320.

Eckstein F., ed., (1991) *Oligonucleotides and Analogs: A Practical Approach*. Oxford University Press, New York.

Eftink M. R. (1991) Fluorescence quenching: theory and applications. In Lakowicz J. R. (ed.), *Topics in Fluorescence Spectroscopy*. Plenum Press, New York, V.2: 53-126.

Fedurco M., Romieu A., Williams S., Lawrence I., Turcatti G. (2006) BTA, a novel reagent for DNA attachment on glass and efficient generation of solid-phase amplified DNA colonies, *Nucleic Acids Res.*, 34: e22.

Fong W., Modrusan Z., McNevin J., Marostenmarki J., Zin B. and Bekkaoui F. (2000) Rapid solid-phase immunoassay for detection of methicillin-resistant *Staphylococcus aureus* using cycling probe technology. *J. Clin. Microbiol.*, 38: 2525-2529.

Förster T. (1965) Delocalized excitation and excitation transfer. In Sinanoglu, O. (ed.), *Modern Quantum Chemistry, Istanbul Lectures, part III*. Academic Press, New York: 93-137.

Freeman W. M., Walker S. J., Vrana K. E. (1999) Quantitative RT-PCR: pitfalls and potential, *Biotechniques*, 26: 112-122, 124-125.

Gait M. J., ed., (1984) *Oligonucleotide Synthesis: A Practical Approach*, IRL Practical Approach Series, IRL Press, Oxford.

Gelfand D. H., Holland P. M., Saiki R. K., Watson R. M. (1993) Homogeneous assay system using the nuclease activity of a nucleic acid polymerase, U.S. Pat. No. 5,210,015.

Gelfand D. H., Kwok S. Y., Sninsky J. J. (1995) Reduction of non-specific amplification glycosylase using DUTP and DNA uracil. U.S. Pat. No. 5,418,149.

Gu Z., Belzer S. W., Gibson C. S., Bankowski M. J., Hayden R. T. (2003) Multiplexed real-time PCR for quantitative detection of human adenovirus. *J. Clin. Microbiol.*, 41: 4636-4641.

Haas B. J., Sandigursky M., Tainer J. A., Franklin W. A. and Cunningham R. P. (1999) Purification and characterization of *Thermotoga maritima* endonuclease IV, a thermostable apurinic/apyrimidinic endonuclease and 3'-repair diesterase. *J. Bacteriol.*, 181: 2834-2839.

Hacia J. G., Woski S. A., Fidanza J., Edgemon K., Hunt N., McGall G., Fodor S. P. A. and Collins F. S. (1998) Enhanced high density oligonucleotide array-based sequence analysis using modified nucleoside triphosphates. *Nucleic Acids Res.*, 26: 4975-4982.

Hafner G. J., Yang I. C., Wolter L. C., Stafford M. R., and Giffard P. M. (2001) Isothermal amplification and multimerization of DNA by Bst DNA polymerase. *BioTechniques*, 30, 852-867.

Hall J. G., Lyamichev V. I., Mast A. L., Brow M. A. D. (1999) Detection of nucleic acids by multiple invasive cleavages. U.S. Pat. No. 5,994,069.

Harvey J. J., Lee S. P., Chan K., Kim J H, Hwang E.-S., Cha C.-Y., Knutson J. R. and Han M. K. (2004) Characterization and application of CataCleave probe in real-time detection assays, *Anal. Biochem.*, 333: 246-255.

Heller M. J. and Morrison L. E. (1985) Chemiluminescent and fluorescent probes for DNA hybridization. In Kingsbury, D. T. and Falkow, S. (eds.), *Rapid Detection and Identification of Infectious Agents*. Academic Press, New York, 245-256.

Higuchi R., Dollinger G., Walsh P. S., and Griffith R. (1992) Simultaneous amplification and detection of specific DNA sequences. *Biotechnology*, 10: 413-417.

Higuchi R., Fockler C., Dollinger G., and Watson R. (1993) Kinetic PCR: Real time monitoring of DNA amplification reactions. *Biotechnology*, 11: 1026-1030.

Ichihara Y., Kurosawa Y. (1993) Construction of new T vectors for direct cloning of PCR products, *Gene*, 130: 153-154.

Ishiguro T., Saitoh J., Yawata H., Yamagishi H., Iwasaki S., Mitoma Y. (1995) Homogeneous quantitative assay of hepatitis C virus RNA by polymerase chain reaction in the presence of a fluorescent intercalater, *Anal. Biochem.*, 229: 207-213.

Johnson M. P., Haupt L. M., Griffiths L. R. (2004) Locked nucleic acid (LNA) single nucleotide polymorphism (SNP) genotype analysis and validation using real-time PCR. *Nucleic Acids Res.*, 32: e55.

Kaiser M. W., Lyamichev V. I., Lyamichev N. (1998) Cleavage of nucleic acid using thermostable methoanococcus jannaschii FEN-1 endonucleases. U.S. Pat. No. 5,843,669.

Kojima T., Takei Y., Ohtsuka M., Kawarasaki Y., Yamane T., Nakano H. (2005) PCR amplification from single DNA molecules on magnetic beads in emulsion: application for high-throughput screening of transcription factor targets, *Nucleic Acids Res.*, 33: e150.

Kornberg A., and Baker T. (1992) *DNA Replication*, Second Edition, W.H. Freeman and Company, New York.

Kurn N. (2001) Methods and compositions for linear isothermal amplification of polynucleotide sequences, using a RNA-DNA composite primer, U.S. Pat. No. 6,251,639.

Kutyavin I. V., Afonina I. A., Mills A., Gorn V. V., Lukhtanov E. A., Belousov E. S., Singer M. J., Walburger D. K., Lokhov S. G., Gall A. A., Dempcy R., Reed M. W., Meyer R. B. and Hedgpeth J. (2000) 3'-Minor groove binder-DNA probes increase sequence specificity at PCR extension temperatures. *Nucleic Acids Res.*, 28: 655-661.

Kutyavin I. V., Lukhtanov E. A., Gamper H. B. and Meyer R. B. (1997) Oligonucleotides with conjugated dihydropyrroloindole tripeptides: base composition and backbone effects on hybridization. *Nucleic Acids Res.*, 25: 3718-3723.

Kutyavin I. V., Milesi D., Hoekstra M. F. (2004) Abasic site endonuclease assay. US Patent Application #20040101893.

Kutyavin I. V., Milesi D., Belousov Y., Podyminogin M., Vorobiev A., Gorn V., Lukhtanov E. A., Vermeulen N. M. J., Mahoney W. (2006) A novel endonuclease IV post-PCR genotyping system. *Nucleic Acids Res.*, 34: e128.

LaDuca R. J., Fay P. J., Chuang C., McHenry C. S., Bambara R. A. (1983) Site-specific pausing of deoxyribonucleic acid synthesis catalyzed by four forms of *Escherichia coli* DNA polymerase III. *Biochemistry*, 22: 5177-5188.

Latorra D., Arar K., Hurley J. M. (2003) Design considerations and effects of LNA in PCR primers, *Mol. Cell. Probes*, 17: 253-259.

Latorra D., Campbell K., Wolter A., Hurley J. M. (2003) Enhanced allele-specific PCR discrimination in SNP genotyping using 3' locked nucleic acid (LNA) primers, *Hum. Mutat.*, 22: 79-85.

Lebedev Y., Akopyans N., Azhikina T., Shevchenko Y., Potapov V., Stecenko D., Berg D., Sverdlov E. (1996) Oligonucleotides containing 2-aminoadenine and 5-methylcytosine are more effective as primers for PCR amplification than their nonmodified counterparts, *Genet. Anal.*, 13, 15-21.

Lehninger A. L. (1975) *Biochemistry*, 2nd edition. New York, Worth Publishers, Inc.

Levin J. D., Johnson A. W. and Dempe B. (1988) Homogeneous *Escherichia coli* endonuclease IV. Characterization of an enzyme that recognizes oxidative damage in DNA. *J. Biol. Chem.*, 263, 8066-8071.

Lewin S. R., Vesanen M, Kostrikis L., Hurley A., Duran M., Zhang L., Ho D. D., Markowitz M. (1999) Use of real-time PCR and molecular beacons to detect virus replication in human immunodeficiency virus type 1-infected individuals on prolonged effective antiretroviral therapy. *J. Virol.*, 73: 6099-6103.

Lie Y. S. and Petropoulos C. J. (1998) Advances in quantitative PCR technology: 5' nuclease assays. *Curr. Opin. Biotech.*, 9: 43-48.

Livak K. J., Flood S. J. A, Marmaro J., Giusti W., Deetz K. (1995) Oligonucleotide with fluorescent dyes at opposite ends provide a quenched probe system useful for detecting PCR product and nucleic acid hybridization. *PCR Methods and Applications*, 4: 357-362.

Livak K. J., Flood S. J. A., Marmaro J. and Mullah K. B. (1998) Self-quenching fluorescent probe. U.S. Pat. No. 5,723,591.

Lizardi P. (1998) Rolling circle replication reporter systems, U.S. Pat. No. 5,854,033.

Ljungquist S. (1977) A new endonuclease from *Escherichia coli* acting at apurinic sites in DNA, *J. Biol. Chem.*, 252, 2808-2814.

Lutfalla G. and Uze G. (2006) Performing quantitative reverse-transcribed polymerase chain reaction experiments, *Methods Enzymol.*, 410: 386-400.

Lyamichev V., Brow M. A., Dahlberg J. E. (1993) Structure-specific endonucleolytic cleavage of nucleic acids by eubacterial DNA polymerases. *Science*, 260: 778-783.

Mackay I. M., Arden K. E., Nitsche A. (2002) Real-time PCR in virology, *Nucleic Acids Res.*, 30: 1292-1305.

Mackay J., Landt O. (2007) Real-time PCR fluorescent chemistries, *Methods Mol. Biol.*, 353: 237-262.

Marras S. A. E., Kramer F. R. and Tyagi S. (2002) Efficiencies of fluorescence resonance energy transfer and contact-mediated quenching in oligonucleotide probes. *Nucleic Acids Res.*, 30: e122.

McPherson M. J., Quirke P., Taylor G. R., eds (1991) *PCR: A Practical Approach*. IRL Press, Oxford.

McPherson M. J., Quirke P., Taylor G. R., eds (1995) *PCR2: A Practical Approach*. IRL Press, Oxford.

Mercier J. F., Slater G. W. (2005) Solid phase DNA amplification: a Brownian dynamics study of crowding effect, *Biophys. J.*, 89: 32-42.

Mercier J. F., Slater G. W., Mayer P. (2003) Solid phase DNA amplification: a sample Monte Carlo Lattice model. *Biophys. J.*, 85: 2075-2086.

Miller S. A., Dykes D. D. and Polesky H. F. (1988) A simple salting out procedure for extracting DNA from human nucleated cells. *Nucleic Acids Res.*, 16: 1215.

Mitterer G., Schmidt W. M. (2006) Microarray-based detection of bacteria by on-chip PCR, *Methods Mol. Biol.*, 345: 37-51.

Modruzan Z., Mariowe C., Wheeler D., Pirseyedi M. and Bryan R. (2000) CPT-EIA assays for the detection of vancomycin resistant vanA and vanB genes in enterococci. *Diagn. Microbiol. Infect. Dis.*, 37: 45-50.

Morrison T. B., Weis J. J., Wittwer C. T. (1998) Quantification of low-copy transcripts by continuous SYBR Green I monitoring during amplification, *Biotechniques*, 24: 954-958.

Mullis K. B. (1987) Process for amplifying nucleic acid sequences, U.S. Pat. No. 4,683,202.

Mullis K. B., Erlich H. A., Arnheim N., Horn G. T., Saiki R. K., and Scharf S. J. (1987) Process for amplifying, detecting, and/or -cloning nucleic acid sequences, U.S. Pat. No. 4,683,195.

Myers T. W. and Gelfand D. H. (1991) Reverse transcription and DNA amplification by a *Thermus thermophilus* DNA polymerase, *Biochemistry*, 30: 7661-7666.

Narang S. A., Hsiung H. M., Brousseau R. (1979) Improved phosphotriester method for the synthesis of gene fragments, *Methods Enzymol.*, 68: 90-98.

Nazarenko I., Lowe B., Darfler M., Ikonomi P., Schuster D., Rashtchian A. (2002) Multiplex quantitative PCR using self-quenched primers labeled with a single fluorophore. *Nucleic Acids Res.*, 30: e37.

Nazarenko I., Pires R., Lowe B., Obaidy M., Rashtchian A. (2002) Effect of primary and secondary structure of oligodeoxyribonucleotides on the fluorescent properties of conjugated dyes. *Nucleic Acids Res.*, 30: 2089-2195.

Nguyen A., Zhao C., Dorris D. and Mazumder A. (2002) Quantitative assessment of the use of modified nucleoside triphosphates in expression profiling: differential effects on signal intensities and impacts on expression ratios. *BMC Biotechnology*, 2: 14.

Niesters H. G. (2001) Quantitation of viral load using real-time amplification techniques, *Methods*, 25: 419-429.

Notomi T. and Hase T. (2002) Process for synthesizing nucleic acid, U.S. Pat. No. 6,410,278.

Notomi T., Okayama H., Masubuchi H., Yonekawa T., Watanabe K., Amino N., and Hase T. (2000) Loop-mediated isothermal amplification of DNA, *Nucleic Acids Res.*, 28, e63.

Oehlenschlager F., Schwille P. and Eigen M. (1996) Detection of HIV-1 RNA by nucleic acid sequence-based amplification combined with fluorescence correlation spectroscopy. *Proc. Natl. Acad. Sci. USA*, 93, 12811-12816.

Ortiz E., Estrada G. and Lizardi P. M. (1998) PNA molecular beacons for rapid detection of PCR amplicons. *Mol. Cell. Probes*, 12, 219-226.

Puglisi J. D. and Tinoco I., Jr. (1989) Absorbance melting curves of RNA. *Methods Enzymol.*, 180: 304-325.

Piatek A. S., Tyagi S., Pol A. C., Telenti A., Miller L. P., Kramer F. R., Alland D. (1998) Molecular beacon sequence analysis for detecting drug resistance in *Mycobacterium tuberculosis*. *Nat. Biotechnol.*, 16: 359-363.

Prudent J. R., Hall J. G., Lyamichev V. I., Brow M. A. D., Dahlberg J. E. (1999) Invasive cleavage of nucleic acids. U.S. Pat. No. 5,985,557.

Prudent J. R., Hall J. G., Lyamichev V. I., Brow M. A. D. (2000) Cleavage of nucleic acids. U.S. Pat. No. 6,090,543.

Prudent J. R., Hall J. G., Lyamichev V. I., Brow M. A. D., Dahlberg J. E. (2002) Invasive cleavage of nucleic acids. U.S. Pat. No. 6,348,314.

Prudent J. R., Hall J. G., Lyamichev V. I., Brow M. A. D., Dahlberg J. E. (2005) Nucleic acid detection assays. U.S. Pat. No. 6,875,572.

Robelek R., Niu L., Schmid E. L., Knoll W. (2004) Multiplexed hybridization detection of quantum dot-conjugated DNA sequences using surface plasmon enhanced fluorescence microscopy and spectrometry, *Anal. Chem.*, 76: 6160-6165.

Sambrook J., Fritsch E. F. and Maniatis T. (1989) *Molecular Cloning: A Laboratory Manual*, 2nd Edition. Cold Spring Harbor Lab. Cold Spring Harbor, N.Y.

SantaLucia J. Jr. (1998) A unified view of polymer, dumbbell, and oligonucleotide DNA nearest-neighbor thermodynamics. *Proc. Natl. Acad. Sci. USA*, 95: 1460-1465.

Schneeberger C., Speiser P., Kury F., Zeillinger R. (1995) Quantitative detection of reverse transcriptase-PCR products by means of a novel and sensitive DNA stain. *PCR Methods Appl.*, 4: 234-238.

Schweitzer B. and Kingsmore S. (2001) Combining nucleic acid amplification and detection. *Curr. Opin. Biotech.*, 12: 21-27.

Selvin P. R. (1995) Fluorescence resonance energy transfer. *Methods Enzymol.*, 246: 300-334.

Simeonov A. and Nikiforov T. T. (2002) Single nucleotide polymorphism genotyping using short, fluorescently labeled locked nucleic acid (LNA) probes and fluorescence polarization detection, *Nucleic Acids Res.*, 30: e91.

Simpson D., Crosby R. M., and Skopek T. R. (1988) A method for specific cloning and sequencing of human hprt cDNA for mutation analysis. *Biochem. Biophys. Res. Commun.*, 151: 487-492.

Sorge J. A. (2001) Methods for detection of a target nucleic acid using a probe comprising secondary structure, U.S. Pat. No. 6,350,580.

Sorge J. A. (2003) Methods for detection of a target nucleic acid sequence, U.S. Pat. No. 6,528,254.

Sorge J. A. (2003) Methods for detection of a target nucleic acid sequence, U.S. Pat. No. 6,548,250.

Sorge J. A. (2003) Methods for detection of a target nucleic acid using a probe comprising secondary structure, U.S. Pat. No. 6,589,743.

Sorge J. A. (2005) Methods for detection of a nucleic acid by sequential amplification, U.S. Pat. No. 6,893,819.

Sorge J. A. (2006) Methods for detection of a target nucleic acid by capture, U.S. Pat. No. 7,118,860.

Sorge J. A. (2007) Methods for detection of a target nucleic acid using multi-subunit probes, U.S. Pat. No. 7,183,052.

Strauss P. R., Beard W. A., Patterson T. A. and Wilson S. H. (1997) Substrate binding by human apurinic/apyrimidinic endonuclease indicates a Briggs-Haldane mechanism. *J. Biol. Chem.*, 272: 1302-1307.

Strauss P. R. and O'Regan N. E. (2001) Abasic site repair in higher eukaryotes. In Nickoloff J. A. and Hoekstra M. F. (eds.), *DNA damage and repair*. Humana Press, Totowa, Vol. III, pp. 43-86.

Stryer L. and Haugland R. P. (1967) Energy transfer: a spectroscopic ruler. *Proc. Natl. Acad. Sci. USA*, 58: 719-726.

Sugimoto N., Nakano S., Yoneyama M. and Honda K. (1996) Improved thermodynamic parameters and helix initiation factor to predict stability of DNA duplexes. *Nucleic Acids Res.*, 24: 4501-4505.

Tecott L., Barchas J. D., Eberwine J. (1992) In situ transcription in cells and tissues, U.S. Pat. No. 5,168,038.

Thelwell N., Millington S., Solinas A., Booth J. and Brown T. (2000) Mode of action and application of Scorpion primers to mutation detection. *Nucleic Acids Res.*, 28: 3752-3761.

Tseng S. Y., Macool D., Elliott V., Tice G., Jackson R., Barbour M., Amorese D. (1997) An homogeneous fluorescence polymerase chain reaction assay to identify *Salmonella*, *Anal. Biochem.*, 245: 207-212.

Tyagi S, and Kramer F. R. (1996) Molecular beacons-probes that fluoresce upon hybridization. *Nat. Biotechnol.*, 14: 303-308.

Tyagi S., Kramer F. R., Lizardi P. M. (1999) Detectably labeled dual conformation oligonucleotide probes, assays and kits, U.S. Pat. No. 5,925,517.

Tyagi S., Marras S. A. E. and Kramer F. R. (2000) Wavelength-shifting molecular beacons. *Nat. Biotechnol.*, 18: 1191-1196.

Van Ness J., Kalbfleisch S., Petrie C. R., Reed M. W., Tabone J. C., and Vermeulen N. J. (1991) A versatile solid support system for oligodeoxynucleotide probe-based hybridization assays. *Nucleic Acids Res.*, 19: 3345-3350.

Vermeulen N., Adams D., Afonina I., Ahmadian M., Belousov Y., Dempcy R., Gorn V., Kutyavin I., Metcalf, M., Milesi D., Mills A., Reed M. W., Sanders S., Scarr N., Shishkina I., Vorobiev A., Walburger D., Wald A., Yau E. (2002) Single nucleotide polymorphism detection with MGB Eclipse™ assays. *J. Clin. Ligand Assay*, 25: 268-275.

Vincent M., Xu Y. and Kong H. (2004) Helicase Dependent Isothermal DNA Amplification, *EMBO reports*, 5: 795-800.

Walker G. T., Linn C. P. and Nadeau J. G. (1996) DNA detection by strand displacement amplification and fluorescence polarization with signal enhancement using DNA binding protein. *Nucleic Acids Res.*, 24, 384-353.

Walker G. T., Little M. C., and Nadeau J. G. (1993) Nucleic acid target generation. U.S. Pat. No. 5,270,184.

Walsh P. S., Metzger D. A., and Higuchi R. (1991) Chelex 100 as a medium for simple extraction of DNA for PCR-based typing from forensic material. *Biotechniques,* 10: 506-513.

Walter A. E., Turner D. H., Kim J., Lyttle M. H., Muller P., Mathews D. H., Zuker M. (1994) Coaxial stacking of helixes enhances binding of oligoribonucleotides and improves predictions of RNA folding, *Proc. Natl. Acad. Sci. USA,* 91: 9218-9222.

Weiss B. (1998) Regulation of endonuclease IV as part of an oxidative stress response in *Escherichia coli*. In Nickoloff J. A. and Hoekstra M. F. (eds.), *DNA damage and repair.* Humana Press, Totowa, Vol. I, pp. 85-96.

Whitcombe D., Theaker J., Guy S. P., Brown T., Little S. (1999) Detection of PCR products using self-probing amplicons and fluorescence. *Nature Biotech.,* 17: 804-807.

Yi J., Zhang W., Zhang D. Y. (2006) Molecular Zipper: a fluorescent probe for real-time isothermal DNA amplification, *Nucleic Acids Res.,* 34: e81.

Zuker M. and Jacobsen A. B. (1995) Well-Determined Regions in RNA Secondary Structure Prediction Analysis of small Subunit Ribosomal RNA, *Nucleic Acids Res.,* 23: 2791-2797.

The invention claimed is:

1. A method for the detection of a target nucleic acid in a sample, comprising:
amplifying, in a reaction mixture, a target nucleic acid using PCR in the presence of a pair of oligonucleotide primers wherein at least one of the oligonucleotide primers is designed to incorporate a 5'-specialty sequence to provide an amplification product that intramolecularly folds into a secondary structure;
and detecting the amplification product that folds into a secondary structure by a method comprising: providing an oligonucleotide cleavage component that has no or reduced priming ability, hybridizing said oligonucleotide cleavage component with the amplification product to form a three-strand cleavage structure wherein two strands of the three-strand cleavage structure are provided by the secondary structure of the amplification product, cleaving 3'- or 5'-strands of the three-strand cleavage structure using a duplex-specific nuclease activity resulting in a cleavage product, and detecting the cleavage product, wherein the presence of the cleavage product is indicative of the presence of the target nucleic acid in said sample.

2. The method of claim 1, wherein each of the oligonucleotides in the primer pair has a 5'-specialty sequence, such that the amplification reaction generates amplification products that intramolecularly fold into the three-strand cleavage structure, and wherein at least one of the oligonucleotide primers is fully extendable during amplification such that the complement of its 5'-specialty sequence provides the 3'-strand of the three-strand cleavage structure, and which has no or reduced priming ability in said three-strand cleavage structure.

3. The method of any one of claim 1 or 2, wherein the target nucleic acid is DNA.

4. The method of any one of claim 1 or 2, wherein the target nucleic acid is RNA and amplifying of the target nucleic acid includes a stage wherein at least one DNA copy of the RNA is synthesized using a reverse transcriptase activity.

5. The method of claim 4, wherein the reverse transcriptase activity is provided by a DNA polymerase used in the PCR.

6. The method of claim 1 or 2, wherein the amplifying of the target nucleic acid is completed, followed by the step of detecting the amplification product.

7. The method of claim 1 or 2, wherein amplifying the target nucleic acid and detecting the amplification product are performed in real time.

8. The method of claim 1, wherein the oligonucleotide cleavage component provides the 3'-strand of the three-strand cleavage structure, and the amplification product which folds into a secondary structure provides the 5'-strand of the three-strand cleavage structure.

9. The method of claim 1, wherein the oligonucleotide cleavage component provides the 5'-strand of the three-strand cleavage structure, wherein the at least one oligonucleotide primer having the 5'-specialty sequence is fully extendable during amplification such that the complement of its 5'-specialty sequence provides the 3'-strand of the three-strand cleavage structure, and which has no or reduced priming ability in said three-strand cleavage structure.

10. The method of claim 8, wherein the oligonucleotide cleavage component is cleaved.

11. The method of claim 8, wherein the amplification product is cleaved.

12. The method of claim 9, wherein the oligonucleotide cleavage component is cleaved.

13. The method of claim 2, wherein the 5'-strand of the three-strand cleavage structure is cleaved.

14. The method of claim 1, comprising amplification of more than one target nucleic acid in the same reaction mixture using, for each target nucleic acid sequence, a pair of oligonucleotide primers wherein at least one of the oligonucleotide primers is designed to incorporate a 5'-specialty sequence to provide an amplification product that intramolecularly folds into a secondary structure, wherein the target nucleic acids are amplified and detected.

15. The method of any one of claims 1 and 2, wherein amplifying and detecting of the target nucleic acid is performed to measure the amount of the target nucleic acid in the sample.

16. The method of any one of claims 1 and 2, wherein amplifying and detecting of the target nucleic acid is performed to determine polymorphic variations of the target nucleic acid in the sample.

17. The method of any one of claims 11, 12 and 13, wherein the duplex-specific cleavage is provided by 5'-nuclease activity.

18. The method of any one of claims 1 and 2, wherein the three-strand cleavage structure is a cleavage structure for 5'-nuclease activity.

19. The method of claim 17, wherein the 5'-nuclease activity is provided by a DNA polymerase used in amplifying said target nucleic acid.

20. The method of claim 19, wherein the DNA polymerase activity is provided by Taq polymerase.

21. The method of claim 17, wherein the 5'-nuclease activity is provided by an enzyme that does not express a DNA polymerase activity.

22. The method of claim 21, wherein the enzyme activity that does not express a DNA polymerase activity is provided by FEN.

23. The method of claim 10, wherein the duplex-specific cleavage is provided by a 3'-nuclease activity.

24. The method of claim 23, wherein the 3'-nuclease activity is provided by an Endonuclease IV or equivalent 3'-nuclease activity.

25. The method of claim 8, wherein the three-strand cleavage structure is a cleavage structure for Endonuclease IV.

26. The method of any one of claims 10 and 12, wherein the cleavage is performed in a cycling mode.

27. The method of any one of claims 1 and 2, wherein oligonucleotide primers that are designed to incorporate a 5'-specialty sequence are fully extendable in PCR.

28. The method of any one of claims 1 and 2, wherein one of the oligonucleotide primers that is designed to incorporate a 5'-specialty sequence is partially extendable in PCR wherein said 5'-specialty sequence is coupled to the 5'-end of the primer through a non-extendable linker.

29. The method of any one of claims 1 and 2, wherein at least one of the oligonucleotide components is immobilized on a solid support during the amplification and/or detection stages.

30. The method of claim 17, wherein the cleavage product comprises or is a flap oligonucleotide.

31. The method of claim 30, wherein the flap oligonucleotide serves as a component of the oligonucleotide cleavage component in a different cleavage reaction in the reaction mixture providing a 3'-strand to a different three-strand cleavage structure that is cleaved by a 5'-nuclease resulting in a different cleavage product, wherein the different cleavage product is detected, and wherein the presence of the different cleavage product is indicative of the presence of the flap oligonucleotide and the target nucleic acid in the sample.

32. The method of claim 31, wherein the different cleavage product contains a label and the label is used in detecting of the different cleavage products.

33. The method of claim 32, wherein the label comprises a fluorescent label.

34. The method of claim 14, wherein amplifying and detecting of the target nucleic acids are performed to measure the amount of the target nucleic acids in the sample.

35. The method of claim 14, wherein amplifying and detecting of the target nucleic acids are performed to determine polymorphic variations of the target nucleic acids in the sample.

36. The method of claim 2, wherein at least the 5' nucleotide of the 5'-specialty sequence of the at least one fully extendable oligonucleotide primer is selected such that the 3'-end of its amplification complement does not hybridize to the target nucleic acid sequence in the three-strand cleavage structure.

37. The method of claim 9, wherein at least the 5' nucleotide of the 5'-specialty sequence of the at least one fully extendable oligonucleotide primer is selected such that the 3'-end of its amplification complement does not hybridize to the target nucleic acid sequence in the three-strand cleavage structure.

* * * * *

SEQUENCE LISTING

```
<160> NUMBER OF SEQ ID NOS: 22

<210> SEQ ID NO 1
<211> LENGTH: 96
<212> TYPE: DNA
<213> ORGANISM: Artificial Sequence
<220> FEATURE:
<223> OTHER INFORMATION: Oligonucleotide

<400> SEQUENCE: 1
cgggcattcc tgaagctgac agcattcggg ccgagatgtc tcgctccgtg gccttagctg      60
tgctcgggct actctctctt tctggcctgg aggcta                               96

<210> SEQ ID NO 2
<211> LENGTH: 21
<212> TYPE: DNA
<213> ORGANISM: Artificial Sequence
<220> FEATURE:
<223> OTHER INFORMATION: Oligonucleotide

<400> SEQUENCE: 2
gcattcctga agctgacagc a                                               21

<210> SEQ ID NO 3
<211> LENGTH: 43
<212> TYPE: DNA
<213> ORGANISM: Artificial Sequence
<220> FEATURE:
<223> OTHER INFORMATION: Oligonucleotide
<220> FEATURE:
<223> OTHER INFORMATION: Linker between positions 19-20

<400> SEQUENCE: 3
tgtctcgctc cgtggccttc tccaggccag aaagagagag tag                       43

<210> SEQ ID NO 4
<211> LENGTH: 39
<212> TYPE: DNA
<213> ORGANISM: Artificial Sequence
<220> FEATURE:
<223> OTHER INFORMATION: Oligonucleotide
<220> FEATURE:
<223> OTHER INFORMATION: Linker between positions 15-16

<400> SEQUENCE: 4
tctcgctccg tggccctcca ggccagaaag agagagtag                            39

<210> SEQ ID NO 5
<211> LENGTH: 37
<212> TYPE: DNA
<213> ORGANISM: Artificial Sequence
<220> FEATURE:
<223> OTHER INFORMATION: Oligonucleotide
```

```
<220> FEATURE:
<223> OTHER INFORMATION: Linker between positions 13-14

<400> SEQUENCE: 5
ctcgctccgt ggcctccagg ccagaaagag agagtag                              37

<210> SEQ ID NO 6
<211> LENGTH: 35
<212> TYPE: DNA
<213> ORGANISM: Artificial Sequence
<220> FEATURE:
<223> OTHER INFORMATION: Oligonucleotide
<220> FEATURE:
<223> OTHER INFORMATION: Linker between positions 11-12

<400> SEQUENCE: 6
tcgctccgtg gctccaggcc agaaagagag agtag                                35

<210> SEQ ID NO 7
<211> LENGTH: 33
<212> TYPE: DNA
<213> ORGANISM: Artificial Sequence
<220> FEATURE:
<223> OTHER INFORMATION: Oligonucleotide
<220> FEATURE:
<223> OTHER INFORMATION: Linker between positions 9-10

<400> SEQUENCE: 7
cgctccgtgc tccaggccag aaagagagag tag                                  33

<210> SEQ ID NO 8
<211> LENGTH: 28
<212> TYPE: DNA
<213> ORGANISM: Artificial Sequence
<220> FEATURE:
<223> OTHER INFORMATION: Oligonucleotide

<400> SEQUENCE: 8
aagcgaggca ttcctgaagc tgacagca                                        28

<210> SEQ ID NO 9
<211> LENGTH: 29
<212> TYPE: DNA
<213> ORGANISM: Artificial Sequence
<220> FEATURE:
<223> OTHER INFORMATION: Oligonucleotide

<400> SEQUENCE: 9
aagcgagagc attcctgaag ctgacagca                                       29

<210> SEQ ID NO 10
<211> LENGTH: 30
<212> TYPE: DNA
<213> ORGANISM: Artificial Sequence
<220> FEATURE:
<223> OTHER INFORMATION: Oligonucleotide

<400> SEQUENCE: 10
aagcgagacg cattcctgaa gctgacagca                                      30

<210> SEQ ID NO 11
<211> LENGTH: 32
<212> TYPE: DNA
<213> ORGANISM: Artificial Sequence
<220> FEATURE:
<223> OTHER INFORMATION: Oligonucleotide
```

```
<400> SEQUENCE: 11
aagcgagaca tgcattcctg aagctgacag ca                                    32

<210> SEQ ID NO 12
<211> LENGTH: 35
<212> TYPE: DNA
<213> ORGANISM: Artificial Sequence
<220> FEATURE:
<223> OTHER INFORMATION: Oligonucleotide

<400> SEQUENCE: 12
aagcgagaca tctcgcattc ctgaagctga cagca                                 35

<210> SEQ ID NO 13
<211> LENGTH: 15
<212> TYPE: DNA
<213> ORGANISM: Artificial Sequence
<220> FEATURE:
<223> OTHER INFORMATION: Oligonucleotide

<400> SEQUENCE: 13
ccgtggcctt agctg                                                       15

<210> SEQ ID NO 14
<211> LENGTH: 30
<212> TYPE: DNA
<213> ORGANISM: Artificial Sequence
<220> FEATURE:
<223> OTHER INFORMATION: Oligonucleotide

<400> SEQUENCE: 14
aagcgagacg cattcctgaa gctgacagca                                       30

<210> SEQ ID NO 15
<211> LENGTH: 32
<212> TYPE: DNA
<213> ORGANISM: Artificial Sequence
<220> FEATURE:
<223> OTHER INFORMATION: Oligonucleotide

<400> SEQUENCE: 15
aagcgagaca tgcattcctg aagctgacag ca                                    32

<210> SEQ ID NO 16
<211> LENGTH: 29
<212> TYPE: DNA
<213> ORGANISM: Artificial Sequence
<220> FEATURE:
<223> OTHER INFORMATION: Oligonucleotide

<400> SEQUENCE: 16
agcgagacgc attcctgaag ctgacagca                                        29

<210> SEQ ID NO 17
<211> LENGTH: 31
<212> TYPE: DNA
<213> ORGANISM: Artificial Sequence
<220> FEATURE:
<223> OTHER INFORMATION: Oligonucleotide

<400> SEQUENCE: 17
agcgagacat gcattcctga agctgacagc a                                     31

<210> SEQ ID NO 18
<211> LENGTH: 31
```

```
<212> TYPE: DNA
<213> ORGANISM: Artificial Sequence
<220> FEATURE:
<223> OTHER INFORMATION: Oligonucleotide

<400> SEQUENCE: 18
ctctcggccc gcattcctga agctgacagc a                              31

<210> SEQ ID NO 19
<211> LENGTH: 31
<212> TYPE: DNA
<213> ORGANISM: Artificial Sequence
<220> FEATURE:
<223> OTHER INFORMATION: Oligonucleotide

<400> SEQUENCE: 19
ccatctcggc gcattcctga agctgacagc a                              31

<210> SEQ ID NO 20
<211> LENGTH: 32
<212> TYPE: DNA
<213> ORGANISM: Artificial Sequence
<220> FEATURE:
<223> OTHER INFORMATION: Oligonucleotide

<400> SEQUENCE: 20
cacatctcgg cgcattcctg aagctgacag ca                             32

<210> SEQ ID NO 21
<211> LENGTH: 32
<212> TYPE: DNA
<213> ORGANISM: Artificial Sequence
<220> FEATURE:
<223> OTHER INFORMATION: Oligonucleotide

<400> SEQUENCE: 21
cgacatctcg gcgcattcctg aagctgacag ca                            32

<210> SEQ ID NO 22
<211> LENGTH: 33
<212> TYPE: DNA
<213> ORGANISM: Artificial Sequence
<220> FEATURE:
<223> OTHER INFORMATION: Oligonucleotide

<400> SEQUENCE: 22
cagacatctc gggcattcct gaagctgaca gca                            33
```